(12) United States Patent
Harris et al.

(10) Patent No.: US 9,439,964 B2
(45) Date of Patent: *Sep. 13, 2016

(54) THERMAL TREATMENT OF THE SKIN SURFACE WITH COATED METAL NANOPARTICLES

(71) Applicant: Sienna Biopharmaceuticals, Inc., Carlsbad, CA (US)

(72) Inventors: Todd James Harris, San Clemente, CA (US); Alice Ann Chen Kim, San Francisco, CA (US)

(73) Assignee: Sienna Biopharmaceuticals, Inc., Carlsbad, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/471,402

(22) Filed: Aug. 28, 2014

(65) Prior Publication Data

US 2014/0371661 A1 Dec. 18, 2014

Related U.S. Application Data

(63) Continuation of application No. 14/020,387, filed on Sep. 6, 2013, now Pat. No. 8,821,940, which is a continuation of application No. 13/219,514, filed on Aug. 26, 2011, now Pat. No. 9,061,056.

(60) Provisional application No. 61/402,305, filed on Aug. 27, 2010, provisional application No. 61/422,612, filed on Dec. 13, 2010, provisional application No. 61/516,308, filed on Apr. 1, 2011.

(51) Int. Cl.

| | | |
|---|---|---|
| *A61B 18/06* | (2006.01) |
| *A61K 41/00* | (2006.01) |
| *A61K 8/02* | (2006.01) |
| *A61K 8/29* | (2006.01) |
| *A61Q 9/04* | (2006.01) |
| *A61K 9/51* | (2006.01) |
| *A61B 17/50* | (2006.01) |
| *A61B 18/20* | (2006.01) |
| *A61N 5/06* | (2006.01) |
| *A61B 18/18* | (2006.01) |
| *A61K 8/11* | (2006.01) |
| *A61Q 9/00* | (2006.01) |
| *A61Q 19/00* | (2006.01) |
| *A61K 8/19* | (2006.01) |
| *A61Q 19/06* | (2006.01) |
| *A61Q 19/08* | (2006.01) |
| *A61K 9/00* | (2006.01) |
| *B82Y 5/00* | (2011.01) |
| *A61B 18/00* | (2006.01) |
| *A61N 5/067* | (2006.01) |

(52) U.S. Cl.
CPC ........... *A61K 41/0052* (2013.01); *A61B 17/50* (2013.01); *A61B 18/06* (2013.01); *A61B 18/18* (2013.01); *A61B 18/203* (2013.01); *A61K 8/0245* (2013.01); *A61K 8/0283* (2013.01); *A61K 8/11* (2013.01); *A61K 8/19* (2013.01); *A61K 8/29* (2013.01); *A61K 9/5115* (2013.01); *A61K 9/5123* (2013.01); *A61K 9/5146* (2013.01); *A61K 9/5153* (2013.01); *A61K 41/0057* (2013.01); *A61N 5/062* (2013.01); *A61N 5/0616* (2013.01); *A61N 5/0617* (2013.01); *A61Q 9/00* (2013.01); *A61Q 9/04* (2013.01); *A61Q 19/00* (2013.01); *A61B 2018/0047* (2013.01); *A61B 2018/00452* (2013.01); *A61B 2018/00476* (2013.01); *A61B 2018/00577* (2013.01); *A61B 2018/068* (2013.01); *A61K 9/009* (2013.01); *A61K 9/0009* (2013.01); *A61K 9/0014* (2013.01); *A61K 2800/413* (2013.01); *A61K 2800/621* (2013.01); *A61K 2800/622* (2013.01); *A61K 2800/624* (2013.01); *A61K 2800/81* (2013.01); *A61N 2005/067* (2013.01); *A61Q 19/06* (2013.01); *A61Q 19/08* (2013.01); *B82Y 5/00* (2013.01)

(58) Field of Classification Search
None
See application file for complete search history.

(56) References Cited

U.S. PATENT DOCUMENTS

| | | |
|---|---|---|
| 4,526,698 A | 7/1985 | Kuroda et al. |
| 5,226,907 A | 7/1993 | Tankovich |
| 5,385,729 A | 1/1995 | Prencipe et al. |
| 5,409,797 A | 4/1995 | Hosoi et al. |
| 5,423,337 A | 6/1995 | Ahlert et al. |
| 5,423,803 A | 6/1995 | Tankovich et al. |

(Continued)

FOREIGN PATENT DOCUMENTS

| | | |
|---|---|---|
| AU | 2011293132 | 8/2011 |
| BR | 102013004902-6 | 2/2013 |

(Continued)

OTHER PUBLICATIONS

Bukasov et al. "Nano Letters—Highly tunable infrared extinction properties of gold nanocrescents." *American Chemical Society*, vol. 7, No. 5 May 2007, published on web Apr. 14, 2007.

(Continued)

*Primary Examiner* — Mina Haghighatian
*Assistant Examiner* — Luke Karpinski
(74) *Attorney, Agent, or Firm* — Knobbe, Martens, Olson & Bear, LLP

(57) ABSTRACT

Treatment of skin tissue with photoactive materials and light, such as nanoparticles and formulations which are useful for cosmetic, diagnostic and therapeutic applications to mammals such as humans. In particular, embodiments of thermal treatment of the skin surface with coated metal nanoparticles are disclosed.

20 Claims, 14 Drawing Sheets

(56) References Cited

U.S. PATENT DOCUMENTS

| | | | |
|---|---|---|---|
| 5,425,728 A | 6/1995 | Tankovich | |
| 5,553,630 A | 9/1996 | Dupuis et al. | |
| 5,593,680 A | 1/1997 | Bara et al. | |
| 5,647,866 A | 7/1997 | Zaias et al. | |
| 5,695,747 A | 12/1997 | Forestier et al. | |
| 5,713,845 A | 2/1998 | Tankovich | |
| 5,750,120 A | 5/1998 | Miguel-Colombel | |
| 5,752,949 A | 5/1998 | Tankovich et al. | |
| 5,756,110 A | 5/1998 | Allard et al. | |
| 5,776,440 A | 7/1998 | Forestier et al. | |
| 5,814,311 A | 9/1998 | Le Bras-Roulier et al. | |
| 5,817,089 A | 10/1998 | Tankovich et al. | |
| 5,830,177 A | 11/1998 | Li et al. | |
| 5,858,381 A | 1/1999 | Le Bras et al. | |
| 5,863,522 A | 1/1999 | Forestier et al. | |
| 5,925,035 A | 7/1999 | Tankovich | |
| 5,955,091 A | 9/1999 | Hansenne | |
| 5,958,389 A | 9/1999 | Le Bras-Roulier et al. | |
| 5,985,300 A | 11/1999 | Crotty et al. | |
| 6,004,567 A | 12/1999 | Marchi-Lemann et al. | |
| 6,036,684 A | 3/2000 | Tankovich et al. | |
| 6,050,990 A | 4/2000 | Tankovich et al. | |
| 6,060,041 A | 5/2000 | Candau et al. | |
| 6,063,074 A | 5/2000 | Tankovich | |
| 6,080,127 A | 6/2000 | Li et al. | |
| 6,132,392 A | 10/2000 | Stone | |
| 6,132,745 A | 10/2000 | Marchi-Lemann et al. | |
| 6,147,982 A | 11/2000 | Sourour et al. | |
| 6,152,917 A | 11/2000 | Tankovich | |
| 6,168,590 B1 | 1/2001 | Neev | |
| 6,183,728 B1 | 2/2001 | Forestier et al. | |
| 6,183,773 B1 | 2/2001 | Anderson | |
| 6,235,270 B1 | 5/2001 | Ishii et al. | |
| 6,238,650 B1 | 5/2001 | Lapidot et al. | |
| 6,267,771 B1 | 7/2001 | Tankovich | |
| 6,283,956 B1 | 9/2001 | McDaniel | |
| 6,287,549 B1 | 9/2001 | Sumian et al. | |
| 6,333,026 B1 | 12/2001 | Lemann | |
| 6,344,050 B1 | 2/2002 | Chen | |
| 6,344,272 B1 | 2/2002 | Oldenburg et al. | |
| 6,365,145 B1 | 4/2002 | Ben-Hur et al. | |
| 6,403,653 B1 | 6/2002 | Hobson et al. | |
| 6,410,603 B1 | 6/2002 | Hobson et al. | |
| 6,428,811 B1 | 8/2002 | West et al. | |
| 6,461,595 B1 | 10/2002 | Leo et al. | |
| 6,491,929 B1 | 12/2002 | Anderson | |
| 6,517,820 B1 | 2/2003 | Robert | |
| 6,521,241 B1 | 2/2003 | Minerath, III et al. | |
| 6,530,944 B2 | 3/2003 | West et al. | |
| 6,534,044 B1 | 3/2003 | Wada et al. | |
| 6,541,017 B1 | 4/2003 | Lemann et al. | |
| 6,589,538 B1 | 7/2003 | Lemann et al. | |
| 6,600,951 B1 | 7/2003 | Anderson | |
| 6,620,407 B1 | 9/2003 | Gers-Barlag et al. | |
| 6,645,517 B2 | 11/2003 | West et al. | |
| 6,660,381 B2 | 12/2003 | Halas et al. | |
| 6,663,658 B1 | 12/2003 | Kollias et al. | |
| 6,676,655 B2 | 1/2004 | McDaniel | |
| 6,685,730 B2 | 2/2004 | West et al. | |
| 6,685,927 B2 * | 2/2004 | Sumian | A61K 8/0241 424/73 |
| 6,685,986 B2 | 2/2004 | Oldenburg et al. | |
| 6,692,755 B2 | 2/2004 | Gers-Barlag et al. | |
| 6,699,724 B1 | 3/2004 | West et al. | |
| 6,706,032 B2 | 3/2004 | Weaver et al. | |
| 6,720,006 B2 | 4/2004 | Hanke et al. | |
| 6,767,547 B2 | 7/2004 | Gers-Barlag et al. | |
| 6,793,913 B2 | 9/2004 | Tournilhac et al. | |
| 6,800,122 B2 | 10/2004 | Anderson et al. | |
| 6,803,049 B2 | 10/2004 | Gers-Barlag et al. | |
| 6,811,770 B2 | 11/2004 | Ferrari et al. | |
| 6,814,760 B2 | 11/2004 | Anderson et al. | |
| 6,821,509 B2 | 11/2004 | Soane et al. | |
| 6,838,088 B2 | 1/2005 | Gers-Barlag et al. | |
| 6,852,252 B2 | 2/2005 | Halas et al. | |
| 6,881,249 B2 | 4/2005 | Anderson et al. | |
| 6,887,260 B1 | 5/2005 | McDaniel | |
| 6,897,238 B2 | 5/2005 | Anderson | |
| 6,942,878 B2 | 9/2005 | Ishii et al. | |
| 6,955,639 B2 | 10/2005 | Hainfeld et al. | |
| 6,989,151 B2 | 1/2006 | Gers-Barlag et al. | |
| 7,018,396 B2 | 3/2006 | Sierra et al. | |
| 7,037,513 B1 | 5/2006 | Traynor et al. | |
| 7,131,446 B2 | 11/2006 | Tang et al. | |
| 7,144,627 B2 | 12/2006 | Halas et al. | |
| 7,201,765 B2 | 4/2007 | McDaniel | |
| 7,270,721 B2 | 9/2007 | Hilfenhaus et al. | |
| 7,367,934 B2 | 5/2008 | Hainfeld et al. | |
| 7,371,457 B2 | 5/2008 | Oldenburg et al. | |
| 7,435,524 B2 | 10/2008 | Anderson et al. | |
| 7,462,496 B2 | 12/2008 | Malak | |
| 7,494,503 B2 | 2/2009 | McDaniel | |
| 7,530,940 B2 | 5/2009 | Hainfeld et al. | |
| 7,648,595 B2 | 1/2010 | Jin et al. | |
| 7,659,301 B2 | 2/2010 | Anderson | |
| 7,704,754 B2 | 4/2010 | Malak | |
| 7,758,561 B2 | 7/2010 | Eppstein | |
| 7,758,888 B2 | 7/2010 | Lapidot et al. | |
| 7,776,130 B2 | 8/2010 | Mirkin et al. | |
| 7,780,955 B2 | 8/2010 | Cassin | |
| 7,785,623 B2 | 8/2010 | Keller | |
| 7,790,066 B2 | 9/2010 | Wang et al. | |
| 7,829,073 B2 | 11/2010 | Martin et al. | |
| 7,959,624 B2 | 6/2011 | Riesinger | |
| 8,033,977 B2 | 10/2011 | Hainfeld et al. | |
| 8,057,418 B2 | 11/2011 | Korbling et al. | |
| 8,062,701 B2 | 11/2011 | McClure et al. | |
| 8,178,202 B2 | 5/2012 | Halas et al. | |
| 8,182,786 B2 | 5/2012 | O'Brien et al. | |
| 8,197,471 B1 | 6/2012 | Tersigni | |
| 8,268,332 B2 | 9/2012 | Manstein | |
| 8,268,638 B2 | 9/2012 | Stein et al. | |
| 8,377,427 B2 | 2/2013 | Giroud et al. | |
| 8,420,062 B2 | 4/2013 | Josso | |
| 8,518,445 B2 | 8/2013 | Alfano et al. | |
| 8,591,924 B2 | 11/2013 | Zheng | |
| 8,613,913 B2 | 12/2013 | Chang et al. | |
| 8,617,580 B2 | 12/2013 | Toledano et al. | |
| 8,652,495 B2 | 2/2014 | Porter et al. | |
| 8,802,154 B2 | 8/2014 | Harris et al. | |
| 8,821,940 B2 | 9/2014 | Harris et al. | |
| 8,821,941 B2 | 9/2014 | Harris et al. | |
| 8,834,447 B2 | 9/2014 | Chen et al. | |
| 8,834,933 B2 | 9/2014 | Harris et al. | |
| 8,871,711 B2 | 10/2014 | Cotsarelis et al. | |
| 8,895,071 B1 | 11/2014 | Harris et al. | |
| 8,906,418 B1 | 12/2014 | Harris et al. | |
| 9,061,056 B2 | 6/2015 | Harris et al. | |
| 9,212,294 B2 | 12/2015 | Oldenburg et al. | |
| 9,249,334 B2 | 2/2016 | Oldenburg et al. | |
| 2001/0002275 A1 | 5/2001 | Oldenburg et al. | |
| 2002/0009488 A1 | 1/2002 | Francis et al. | |
| 2002/0034480 A1 | 3/2002 | Grimm et al. | |
| 2002/0041854 A1 | 4/2002 | Hadasch et al. | |
| 2002/0061363 A1 | 5/2002 | Halas et al. | |
| 2002/0103517 A1 | 8/2002 | West et al. | |
| 2002/0132045 A1 | 9/2002 | Halas et al. | |
| 2002/0187172 A1 | 12/2002 | Reb et al. | |
| 2002/0192298 A1 | 12/2002 | Burrell et al. | |
| 2003/0060811 A1 | 3/2003 | McDaniel | |
| 2003/0072728 A1 | 4/2003 | Soane et al. | |
| 2003/0095941 A1 | 5/2003 | Anderson | |
| 2003/0099718 A1 | 5/2003 | Burrell et al. | |
| 2003/0118657 A1 | 6/2003 | West et al. | |
| 2003/0156991 A1 | 8/2003 | Halas et al. | |
| 2003/0170189 A1 | 9/2003 | Victor | |
| 2003/0215638 A1 | 11/2003 | Charnay et al. | |
| 2004/0006328 A1 * | 1/2004 | Anderson | A61K 41/0028 604/501 |
| 2004/0151673 A1 | 8/2004 | Josso | |
| 2004/0166508 A1 | 8/2004 | Pawlak et al. | |
| 2004/0170579 A1 | 9/2004 | Mobius | |
| 2004/0197286 A1 | 10/2004 | Robert et al. | |
| 2004/0219179 A1 | 11/2004 | McDaniel | |

(56) References Cited

U.S. PATENT DOCUMENTS

| | | |
|---|---|---|
| 2004/0253138 A1 | 12/2004 | Malak |
| 2004/0253757 A1 | 12/2004 | Gourlaouen et al. |
| 2005/0031655 A1 | 2/2005 | Karpov |
| 2005/0031658 A1 | 2/2005 | Girier Dufournier et al. |
| 2005/0044642 A1 | 3/2005 | Butcher |
| 2005/0048546 A1 | 3/2005 | Penn et al. |
| 2005/0053629 A1 | 3/2005 | Ueda et al. |
| 2005/0058672 A1 | 3/2005 | Gupta |
| 2005/0058678 A1 | 3/2005 | Ricard et al. |
| 2005/0059030 A1 | 3/2005 | Bao et al. |
| 2005/0130324 A1 | 6/2005 | West et al. |
| 2005/0169866 A1 | 8/2005 | Hannich et al. |
| 2005/0175649 A1 | 8/2005 | Disalvo et al. |
| 2005/0186235 A1 | 8/2005 | Martin et al. |
| 2005/0187128 A1 | 8/2005 | Martin et al. |
| 2005/0203495 A1 | 9/2005 | Malak |
| 2005/0220741 A1 | 10/2005 | Dumousseaux |
| 2005/0229334 A1 | 10/2005 | Huang et al. |
| 2006/0078578 A1 | 4/2006 | Sandewicz et al. |
| 2006/0083762 A1 | 4/2006 | Brun et al. |
| 2006/0257336 A1 | 11/2006 | Ferrari et al. |
| 2007/0032781 A1 | 2/2007 | Henry et al. |
| 2007/0065387 A1 | 3/2007 | Beck et al. |
| 2007/0078290 A1 | 4/2007 | Esenaliev |
| 2007/0092471 A1 | 4/2007 | Cassier et al. |
| 2007/0104605 A1 | 5/2007 | Hampden-Smith et al. |
| 2007/0125383 A1 | 6/2007 | Ko |
| 2007/0154903 A1 | 7/2007 | Marla et al. |
| 2007/0158611 A1 | 7/2007 | Oldenburg |
| 2007/0160636 A1 | 7/2007 | Kasai |
| 2007/0166248 A1 | 7/2007 | L'Alloret et al. |
| 2007/0183992 A1 | 8/2007 | Dumousseaux et al. |
| 2007/0196305 A1 | 8/2007 | Wang et al. |
| 2007/0208400 A1 | 9/2007 | Nadkarni et al. |
| 2007/0217996 A1 | 9/2007 | Levy et al. |
| 2007/0231940 A1 | 10/2007 | Gourlaouen et al. |
| 2008/0045865 A1 | 2/2008 | Kislev |
| 2008/0050448 A1 | 2/2008 | Wilson et al. |
| 2008/0204742 A1 | 8/2008 | Halas et al. |
| 2008/0233060 A1 | 9/2008 | Grune |
| 2008/0241262 A1* | 10/2008 | Lee .................... A61K 9/0009 424/490 |
| 2008/0305337 A1 | 12/2008 | Berning et al. |
| 2009/0022765 A1 | 1/2009 | Chung et al. |
| 2009/0022766 A1 | 1/2009 | Geddes |
| 2009/0053268 A1 | 2/2009 | DePablo et al. |
| 2009/0123509 A1 | 5/2009 | Berkland et al. |
| 2009/0175915 A1 | 7/2009 | Maitra et al. |
| 2009/0177122 A1 | 7/2009 | Peterson |
| 2009/0217465 A1 | 9/2009 | Cremer et al. |
| 2009/0226521 A1 | 9/2009 | Smyth et al. |
| 2009/0246142 A1 | 10/2009 | Bhatia et al. |
| 2009/0291107 A1 | 11/2009 | Schehlmann et al. |
| 2009/0326614 A1 | 12/2009 | El-Sayed et al. |
| 2010/0002282 A1 | 1/2010 | Agrawal et al. |
| 2010/0016783 A1 | 1/2010 | Bourke, Jr. |
| 2010/0040549 A1 | 2/2010 | Halas et al. |
| 2010/0049178 A1 | 2/2010 | Deem et al. |
| 2010/0055138 A1 | 3/2010 | Margulies et al. |
| 2010/0056485 A1 | 3/2010 | Park |
| 2010/0057068 A1 | 3/2010 | Lee |
| 2010/0104652 A1 | 4/2010 | Biris et al. |
| 2010/0119610 A1 | 5/2010 | Schoen et al. |
| 2010/0143431 A1 | 6/2010 | Landau et al. |
| 2010/0172994 A1 | 7/2010 | Sigmund et al. |
| 2010/0174223 A1 | 7/2010 | Sakamoto et al. |
| 2010/0204686 A1 | 8/2010 | Yaroslavksy et al. |
| 2010/0224026 A1 | 9/2010 | Brennan Fournet et al. |
| 2010/0233222 A1 | 9/2010 | Girier Dufournier et al. |
| 2010/0254920 A1 | 10/2010 | L'Alloret et al. |
| 2010/0260700 A1 | 10/2010 | Dop |
| 2010/0266647 A1 | 10/2010 | Dingley et al. |
| 2010/0266649 A1 | 10/2010 | Maitra et al. |
| 2010/0272789 A1 | 10/2010 | Satoh et al. |
| 2010/0284924 A1 | 11/2010 | Zink et al. |
| 2010/0291166 A1 | 11/2010 | Guyot-Ferreol et al. |
| 2010/0291224 A1 | 11/2010 | Tong et al. |
| 2010/0298758 A1 | 11/2010 | Christiansen et al. |
| 2010/0303716 A1 | 12/2010 | Jin et al. |
| 2010/0305495 A1 | 12/2010 | Anderson et al. |
| 2010/0323996 A1 | 12/2010 | Ute et al. |
| 2011/0021970 A1 | 1/2011 | Vo-Dinh et al. |
| 2011/0034855 A1 | 2/2011 | Esenaliev |
| 2011/0052672 A1 | 3/2011 | Krishnan et al. |
| 2011/0091572 A1 | 4/2011 | Davidson |
| 2011/0111002 A1 | 5/2011 | Pop |
| 2011/0117202 A1 | 5/2011 | Bourke, Jr. et al. |
| 2011/0144030 A1 | 6/2011 | Ramis Castelltort et al. |
| 2011/0159291 A1 | 6/2011 | Sun et al. |
| 2011/0168200 A1 | 7/2011 | Bourdin et al. |
| 2011/0223255 A1 | 9/2011 | Thiesen et al. |
| 2011/0229559 A1 | 9/2011 | Prestidge et al. |
| 2011/0240556 A1 | 10/2011 | Hoek et al. |
| 2011/0288234 A1 | 11/2011 | Pandey |
| 2012/0021030 A1 | 1/2012 | Matsufuji et al. |
| 2012/0059307 A1 | 3/2012 | Harris et al. |
| 2012/0101007 A1 | 4/2012 | Ahern et al. |
| 2012/0141380 A1 | 6/2012 | Margel et al. |
| 2012/0289955 A1 | 11/2012 | Marc |
| 2013/0017238 A1 | 1/2013 | Porter et al. |
| 2013/0022655 A1 | 1/2013 | Sachweh et al. |
| 2013/0023714 A1 | 1/2013 | Johnston et al. |
| 2013/0183244 A1 | 7/2013 | Hanes et al. |
| 2013/0195979 A1 | 8/2013 | Tersigni |
| 2013/0216596 A1 | 8/2013 | Viladot Petit et al. |
| 2013/0225901 A1 | 8/2013 | Krishnan et al. |
| 2013/0251825 A1 | 9/2013 | Berry |
| 2013/0315650 A1 | 11/2013 | Cassin et al. |
| 2013/0315999 A1 | 11/2013 | Paithankar et al. |
| 2013/0323305 A1 | 12/2013 | Paithankar et al. |
| 2013/0338545 A1 | 12/2013 | Azhari et al. |
| 2014/0005593 A1 | 1/2014 | Harris et al. |
| 2014/0012162 A1 | 1/2014 | Harris et al. |
| 2014/0012163 A1 | 1/2014 | Harris et al. |
| 2014/0012183 A1 | 1/2014 | Harris et al. |
| 2014/0030300 A1 | 1/2014 | Maitra et al. |
| 2014/0105982 A1 | 4/2014 | Oldenburg et al. |
| 2014/0120041 A1 | 5/2014 | Prencipe et al. |
| 2014/0120167 A1 | 5/2014 | Lapotko et al. |
| 2014/0120168 A1 | 5/2014 | Oldenburg et al. |
| 2014/0194900 A1 | 7/2014 | Sedic |
| 2014/0205546 A1 | 7/2014 | Macoviak |
| 2014/0243934 A1 | 8/2014 | Vo-Dinh et al. |
| 2014/0271889 A1 | 9/2014 | Messersmith et al. |
| 2014/0303525 A1 | 10/2014 | Sitharaman |
| 2014/0316387 A1 | 10/2014 | Harris et al. |
| 2014/0316394 A1 | 10/2014 | Quidant et al. |
| 2014/0371654 A1 | 12/2014 | Harris et al. |
| 2014/0371655 A1 | 12/2014 | Harris et al. |
| 2014/0371656 A1 | 12/2014 | Harris et al. |
| 2014/0371658 A1 | 12/2014 | Harris et al. |
| 2014/0371659 A1 | 12/2014 | Harris et al. |
| 2014/0371661 A1 | 12/2014 | Harris et al. |
| 2014/0371662 A1 | 12/2014 | Harris et al. |
| 2014/0371663 A1 | 12/2014 | Harris et al. |
| 2014/0371664 A1 | 12/2014 | Harris et al. |
| 2015/0005691 A1 | 1/2015 | Harris et al. |
| 2015/0045723 A1 | 2/2015 | Paithankar et al. |
| 2015/0165180 A1 | 6/2015 | Anderson et al. |
| 2015/0190341 A1 | 7/2015 | Paithankar et al. |
| 2015/0196359 A1 | 7/2015 | Paithankar et al. |
| 2015/0196452 A1 | 7/2015 | Meyer et al. |
| 2015/0196639 A1 | 7/2015 | Lando et al. |
| 2015/0225599 A1 | 8/2015 | Oldenburg et al. |

FOREIGN PATENT DOCUMENTS

| | | |
|---|---|---|
| CA | 2806592 | 8/2011 |
| CN | 201180041302.8 | 8/2011 |
| DE | 3905167 | 8/1989 |
| DE | 4344141 | 7/1995 |
| DE | 10342258 | 4/2005 |
| DE | 10351611 | 8/2005 |
| DE | 102004002990 | 8/2005 |

(56) References Cited

FOREIGN PATENT DOCUMENTS

| | | |
|---|---|---|
| DE | 102005007482 | 9/2006 |
| DE | 102007020554 | 10/2008 |
| DE | 102008052187 | 4/2010 |
| EP | 409690 | 9/1993 |
| EP | 518772 | 11/1994 |
| EP | 518773 | 2/1995 |
| EP | 555460 | 5/1995 |
| EP | 614656 | 10/1996 |
| EP | 586484 | 1/1998 |
| EP | 0601130 | 8/1998 |
| EP | 0712322 | 4/1999 |
| EP | 0925807 | 6/1999 |
| EP | 0860123 | 1/2002 |
| EP | 966954 | 2/2002 |
| EP | 1112325 | 5/2003 |
| EP | 1185242 | 8/2005 |
| EP | 1201219 | 12/2005 |
| EP | 1325730 | 10/2006 |
| EP | 1506764 | 4/2007 |
| EP | 1506763 | 7/2007 |
| EP | 1506765 | 7/2007 |
| EP | 1506766 | 7/2007 |
| EP | 1529513 | 3/2008 |
| EP | 1317245 | 5/2008 |
| EP | 1677843 | 8/2008 |
| EP | 1744789 | 8/2008 |
| EP | 1768749 | 10/2008 |
| EP | 1267801 | 12/2008 |
| EP | 1559393 | 5/2009 |
| EP | 1559394 | 3/2010 |
| EP | 1208005 | 4/2010 |
| EP | 1861465 | 10/2010 |
| EP | 1502574 | 11/2010 |
| EP | 1167462 | 12/2010 |
| EP | 11820765.3 | 8/2011 |
| EP | 2231283 | 9/2012 |
| EP | 988853 | 10/2012 |
| EP | 1263447 | 6/2013 |
| EP | 2396010 | 8/2013 |
| EP | 2416752 | 9/2013 |
| EP | 1267747 | 1/2014 |
| EP | 1959914 | 5/2014 |
| IL | 224390 | 8/2011 |
| IN | 1651/DELNP/2013 | 8/2011 |
| JP | 513047246 | 8/2011 |
| WO | WO 91/06894 | 5/1991 |
| WO | WO95/033518 | 12/1995 |
| WO | WO96/20698 | 7/1996 |
| WO | WO96/041579 | 12/1996 |
| WO | WO97/00098 | 1/1997 |
| WO | WO99/46351 | 9/1999 |
| WO | WO00/02590 | 1/2000 |
| WO | WO00/40266 | 7/2000 |
| WO | WO01/05586 | 1/2001 |
| WO | WO01/06257 | 1/2001 |
| WO | WO01/58458 | 8/2001 |
| WO | WO02/085385 | 10/2002 |
| WO | WO03/026481 | 4/2003 |
| WO | WO2004058352 | 7/2004 |
| WO | WO2004/086044 | 10/2004 |
| WO | WO2005/092286 | 10/2005 |
| WO | WO 2006/122222 | 11/2006 |
| WO | WO 2008/079758 | 7/2008 |
| WO | WO 2008/079760 | 7/2008 |
| WO | WO 2005/077329 | 8/2008 |
| WO | WO2008/106966 | 9/2008 |
| WO | WO2009/117124 | 9/2009 |
| WO | WO2010/073260 | 7/2010 |
| WO | WO 2010/109545 | 9/2010 |
| WO | WO2010/116345 | 10/2010 |
| WO | WO 2010/116346 | 10/2010 |
| WO | WO 2010/137580 | 12/2010 |
| WO | WO 2011/013101 | 2/2011 |
| WO | WO2011/031871 | 3/2011 |
| WO | WO2011/095970 | 8/2011 |
| WO | WO2011/116963 | 9/2011 |
| WO | WO2012/027728 | 3/2012 |
| WO | WO 2012/035029 | 3/2012 |
| WO | WO2012/059944 | 5/2012 |
| WO | WO 2013/106998 | 7/2013 |
| WO | WO 2013/106999 | 7/2013 |
| WO | WO 2013/107000 | 7/2013 |
| WO | WO 2013/107001 | 7/2013 |
| WO | WO 2013/107002 | 7/2013 |
| WO | WO 2013/107349 | 7/2013 |
| WO | WO 2013/107350 | 7/2013 |
| WO | WO 2013/107351 | 7/2013 |
| WO | WO 2013/107352 | 7/2013 |
| WO | WO 2013/107353 | 7/2013 |
| WO | WO 2013/107354 | 7/2013 |
| WO | WO2013/158278 | 10/2013 |
| WO | WO 2013/160362 | 10/2013 |
| WO | WO 2013/169955 | 11/2013 |
| WO | WO 2014/026142 | 2/2014 |
| WO | WO 2014/052973 | 4/2014 |
| WO | WO 2014/145784 | 9/2014 |

OTHER PUBLICATIONS

Ghaffarpour, Azizjalali M. et al., "CO2 Laser therapy versus cryotherapy in treatment of genital warts; a Randomized Controlled Trial (RCT)", *Iranian Journal of Microbiology*, vol. 4, No. 4, Dec. 2012, 187-190.

Lazare, M. What are Cold Sores (Herpetic Lesions)?, http://www.drmarclazare.com/laser-treatments-for-cold-soresherpetic-lesions/, dated Jul. 8, 2014.

Lewicka et al. "Nanorings and nanocrescents formed via shaped nanosphere lithography: a route toward large areas of infrared metamaterials." *IOP Publishihg*, Nanotechnology 24: Feb. 28, 2013.

Maltzahn, Geoffrey von, et al., "Computationally Guided Photothermal Tumor Therapy Using Long-Circulating Gold Nanorod Antennas" Cancer Res 2009; 69: (9) Published online Apr. 14, 2009 as 10.11158/008-5472.CAN-08-4242.

Rallis, Tena M., "Low-Intensity Laser Therapy for Recurrent Herpes Labialis" *The Journal of Investigative Dermatology*, vol. 115, No. 1 Jul. 2000.

Amirthalingam et al. "Use of Silica-Gold Core Shell Structure Nanoparticles for Targeted Drug Delivery System" J. Nanomedic Nanotechnol 2:119, (2011) vol. 2, Issue 6.

Lewicka et al. "Nanorings and nanocrescents formed via shaped nanosphere lithography: a route toward large areas of infrared metamaterials." *IOP Publishing*, Nanotechnology 24: Feb. 28, 2013.

Prosecution history (excluding references of record) of U.S. Appl. No. 13/789,575, including a 37 CFR 1.131 declaration over US Publication 2014/0005593 with U.S. Appl. No. 14/020,481, now U.S. Pat. No. 8,821,941, which shares common priority and/or an inventor with the present application. The 131 declaration is dated Dec. 31, 2014 (submission date to USPTO).

Kulkarni et al., "Effect of Experimental Temperature on the Permeation of Model Diffusants Across Porcine Buccal Mucosa" AAPS PharmSciTech. Jun. 2011; 12(2)579.

Prosecution history (excluding references of record) of U.S. Appl. No. 13/789,575, namely an Amendment and a Suggestion for Declaration of Interference (with Appendices) over US Publication 2014/0005593 with U.S. Appl. No. 14/020,481, now U.S. Pat. No. 8,821,941, which shares common priority and/or an inventor with the present application. The Amendment and Suggestion for Declaration of Interference (with Appendices) and related documentation is dated Jul. 28, 2015 (submission date to USPTO) (Part 1 of 5).

Prosecution history (excluding references of record) of U.S. Appl. No. 13/789,575, namely Exhibits from a Suggestion for Declaration of Interference over US Publication 2014/0005593 with U.S. Appl. No. 14/020,481, now U.S. Pat. No. 8,821,941, which shares common priority and/or an inventor with the present application. The Exhibits from a Suggestion for Declaration of Interference and related documentation is dated Jul. 28, 2015 (submission date to USPTO) (Part 2 of 5).

(56) References Cited

OTHER PUBLICATIONS

Prosecution history (excluding references of record) of U.S. Appl. No. 13/789,575, namely Exhibits from a Suggestion for Declaration of Interference over US Publication 2014/0005593 with U.S. Appl. No. 14/020,481, now U.S. Pat. No. 8,821,941, which shares common priority and/or an inventor with the present application. The Exhibits from a Suggestion for Declaration of Interference and related documentation is dated Jul. 28, 2015 (submission date to USPTO) (Part 3 of 5).
Prosecution history (excluding references of record) of U.S. Appl. No. 13/789,575, namely Exhibits from a Suggestion for Declaration of Interference over US Publication 2014/0005593 with U.S. Appl. No. 14/020,481, now U.S. Pat. No. 8,821,941, which shares common priority and/or an inventor with the present application. The Exhibits from a Suggestion for Declaration of Interference and related documentation is dated Jul. 28, 2015 (submission date to USPTO) (Part 4 of 5).
Prosecution history (excluding references of record) of U.S. Appl. No. 13/789,575, namely Exhibits from a Suggestion for Declaration of Interference over US Publication 2014/0005593 with U.S. Appl. No. 14/020,481, now U.S. Pat. No. 8,821,941, which shares common priority and/or an inventor with the present application. The Exhibits from a Suggestion for Declaration of Interference and related documentation is dated Jul. 28, 2015 (submission date to USPTO) (Part 5 of 5).
Prosecution history (excluding references of record) of U.S. Appl. No. 13/789,575, namely an amendment in view of a Suggestion for Declaration of Interference over US Publication 2014/0005593 with U.S. Appl. No. 14/020,481, now U.S. Pat. No. 8,821,941, which shares common priority and/or an inventor with the present application. The amendment and related documentation is dated Aug. 19, 2015 (submission date to USPTO).
Prosecution history (excluding references of record) of U.S. Appl. No. 13/789,575, namely an Advisory Action further to a Suggestion for Declaration of Interference over US Publication 2014/0005593 with U.S. Appl. No. 14/020,481, now U.S. Pat. No. 8,821,941, which shares common priority and/or an inventor with the present application. The Advisory Action and related documentation is dated Aug. 21, 2015 (mailing date from USPTO).
Patent Interference document—Declaration of Interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 1, dated Oct. 8, 2015).
Patent Interference document—Sienna notice of Real Party-In-Interest in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 5, dated Oct. 22, 2015).
Patent Interference document—Sienna notice of Related Proceedings in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 6, dated Oct. 22, 2015).
Patent Interference document—Sienna Clean Claims in interference between Senior Party U.S. Pat. No. 8,821,941 which shares common priority, assignee, and inventorship with the present application, and Junior Party U.S. Appl. No. 13/789,575 (U.S. Patent and Trademark Office, Patent Interference No. 106,037 (DK) Paper 7, dated Oct. 22, 2015).
Patent Interference document—General Hospital Notice of Real Party-In-Interest in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 13, dated Oct. 22, 2015).
Patent Interference document—General Hospital Clean Claims in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 14, dated Oct. 22, 2015).
Patent Interference document—General Hospital Notice of Related Proceedings in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 15, dated Oct. 22, 2015).
Patent Interference document—Sienna Annotated Claims in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 19, dated Nov. 5, 2015).
Patent Interference document—General Hospital Annotated Claims in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 20, dated Nov. 5, 2015).
Patent Interference document—Sienna Proposed Motions in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 21, dated Nov. 12, 2015).
Patent Interference document—General Hospital Proposed Motions in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 22, dated Nov. 12, 2015).
Patent Interference document—Order Expunging General Hospital papers in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 42, dated Nov. 13, 2015).
Patent Interference document—Order Authorizing Motions and Setting Times in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 46, dated Nov. 23, 2015).
Patent Interference document—Sienna Substantive Motion 1 for judgment that GHC's claims are unpatentable under 35 U.S.C. § 112, first paragraph in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 84, dated Feb. 10, 2016).
Patent Interference document—Sienna Substantive Motion 2 to be accorded benefit of the filing dates of Sienna U.S. Appl. Nos. 61/402,305; 61/422,612; and 61/516,308 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 85, dated Feb. 10, 2016).
Patent Interference document—First Declaration of Andrea Tao, Ph.D., in Support of Sienna Motions 1 and 2 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1002, filed on Feb. 10, 2016).
Patent Interference document—General Hospital Motion 1 for Benefit of the Filing Date of Provisional U.S. Appl. No. 61/636,381 in interference between Senior Party U.S. Pat. No. 8,821,941, which

(56) References Cited

OTHER PUBLICATIONS shares common priority, assignee, and inventorship with the present application, and Junior Party U.S. Appl. No. 13/789,575 (U.S. Patent and Trademark Office, Patent Interference No. 106,037 (DK) Paper 151, dated Feb. 10, 2016).
Patent Interference document—General Hospital Motion 2 for Finding of Lack of: (1) Written Description and (2) Enablement Under 35 U.S.C. § 112, First Paragraph in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 152, dated Feb. 10, 2016).
Patent Interference document—General Hospital Motion 3 to Vacate Accorded Benefit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 153, dated Feb. 10, 2016).
Patent Interference document—Second Declaration of Ivan J. Dmochowski in interference between Senior Party U.S. Pat. No. 8,821,941, which shares common priority, and inventorship with the present application, and Junior Party U.S. Appl. No. 13/789,575 (U.S. Patent and Trademark Office, Patent Interference No. 106,037 (DK) Exhibit 2025, dated Feb. 10, 2016).
Patent Interference document—Order under 37 C.F.R. § 41.104(a) in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 159, dated Feb. 25, 2016).
Patent Interference document—Sienna Updated Real Party in Interest in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 160, dated Feb. 26, 2016).
Selections of prosecution history (excluding copies of references of record) of U.S. Appl. No. 13/789,575, namely a Suggestion for Declaration of Interference (with Exhibits) over US Publication 2014/0005593 with U.S. Appl. No. 14/020,481, now U.S. Pat. No. 8,821,941, which shares common priority and/or an inventor with the present application. The Suggestion for Declaration of Interference (with related documentation) is dated Jul. 28, 2015 (submission date to USPTO).
Aherne, et al. "Optical Properties and Growth Aspects of Silver Nanoprisms Produced by Highly Reproducible and Rapid Synthesis at Room Temperature." Advanced Materials, Adv. Funct. Mater. Jul. 9, 2008, v18, 2005-2016.
Ammad et al. "An assessment of the efficacy of blue light phototherapy in the treatment of acne vulgaris." *J. Cosmet Dermatol*, 2008, 7: 180-188.
Charles et al. "Versatile Solution Phase Triangular Silver Nanoplats for Highly Sensitive Plasmon Resonance Sensing" American Chemical Society NANO, v4, No. 1 p. 55-64, Dec. 23, 2009.
Chen et al. "Controlling 2-dimensional growth of silver nanoplates." Self-Assembled Nanostructured Materials Symposium. Mat. Res. Soc. Symp. Proc. vol. 775, 343-348lxiii+394. (2003).
Chen et al. "Silver nanodisks: Synthesis, characterization, and self-assembly." J. Phys. Chem. B, vol. 106, No. 42, 2002 10777-10781. (Published Sep. 21, 2002).
Chen, et al. "Silver nanoplates: Size control in two dimensions and formation mechanisms." J. Phys. Chem. B 2004, 108, 5500-5506 Journal of Physical Chemistry B, 108, 5500-5506. (Published Apr. 14, 2004).
Chen, et al. "Synthesis and characterization of truncated triangular silver nanoplates." Nano Letters, 2002, 2 (9), 1003-1007. (Published Jul. 26, 2002).

Choudhary and Elsaie, M.L. "Photodynamic therapy in dermatology: a review." *Lasers Med Sci.*, 2009, 24:971-980.
Dierickx, et al. "Photodynamic Therapy for Nevus Sebaceus With Topical d-Aminolevulinic Acid", Arch Dermatol, vol. 135, Jun. 1993, pp. 637-640.
Divaris, et al. "Phototoxic Damage to Sebaceous Glands and Hair Follicles of Mice After Systemic Administration of 5-Aminolevulinic Acid Correlates with Localized Protoporphyrin IX Florescence", American Journal of Pathology, vol. 136, No. 4, Apr. 1990, pp. 891-897.
Donnelly et al. "Photosensitiser delivery for photodynamic therapy. Part 1: Topical carrier platforms." *Expert Opin Drug Deliv.* 2008, 5:757-766.
Gollnick et al. "Can we define acne as a chronic disease? If so, how and when?" *Am J Clin Dermatol*, 2008, 9:279-284.
Grachtchouk et al. "Basal cell carcinomas in mice arise from hair follicle stem cells and multiple epithelial progenitor populations." *J Clin Invest*, 2011, 121: 1768-1781.
Grams et al. "Permeant lipophilicity and vehicle composition influence accumulation of dyes in hair follicles of human skin," *Eur J Pharm Sci*, 2003, 18:329-336.
Hao E. K., et al. "Synthesis of Silver Nanodisks using Polystyrene Mesospheres as Templates." J Am Chem Soc, 124, 15182-15183. (Published Nov. 22, 2002).
Hao E., et al. "Synthesis and optical properties of anisotropic metal nanoparticles." Journal of Fluorescence, vol. 14, No. 4, Jul. 2004, 331-341. (Published Jul. 2004).
He et al. "Surface Plasmon Resonances of Silver Triange Nanoplates: Graphic Assignments of Resonance Modes and Linear Fittings of Resonance Peaks" J. Phys. Chem. B 2005, 109, 17503-17511 (Published Aug. 20, 2005).
He, et al. "The evidence for synthesis of truncated silver nanoplates in the presence of CTAB." Materials Characterization, 59, 380-384. (Publshed 2008).
Hongcharu et al. "Topical ALA-photodynamic therapy for the treatment of acne vulgaris." *J Invest Dermatol*, 2000, 115:183-192.
Hongcharu, et al. "Topical ALA-Photodynamic Therapy for the Treatment of Acne Vulgaris", Journal of Invest. Dermatology, vol. 115, No. 2, Aug. 2000, pp. 1-10.
Huang et al. Microemulsification of triglyceride sebum and the role of interfacial structure on bicontinuousphase behavior.: *Langmuir*, 2004, 20:3559-3563.
Jiang et al. "A self-seeding coreduction method for shape control of silver nanoplates" Nanotechnology 17 (2006) 4929-4935 (Published Sep. 11, 2006).
Jin et al. "Photoinduced Conversion of Silver Nanospheres to Nanoprisms." Science, v 294, 1901-1903. (Published Nov. 30, 2001).
Jin, et al "Controlling anisotropic nanoparticle growth through plasmon excitation." Nature, v. 425, 487-490 (Published Oct. 2, 2003).
Kjeldstad, et al. "Changes in Polyphosphate Composition and Localization in Propionibacterium Acnes After Near-Ultraviolet Irradiation", Canadian Journal of Microbiology, vol. 37, No. 7, Jul. 1991, 562-567 (Abstract, 1 Page).
Knorr et al. "Follicular transport route-research progress and future perspectives." *Eur J Pharm Biopharm*, 2009, 71:173-180.
Koenig, et al. "Photodynamic-Induced Inactivation of Propionibacterium Acnes", SPIE Proceedings, SPIE-Int. Soc. Opt. Eng., 106-110, vol. 3247, Jan. 1998 (Abstract, 3 Pages).
Konig, et al. "Photodynamic Activity of Methylene Blue", Aktuelle Dermatol, vol. 19, 1993, pp. 195-198.
Konig, et al. "Photodynamically Induced Inactivation of Propionibacterium Acnes Using the Photosensitizer Methylene Blue and Red Light", Dermatologische Monatsschrift (Dematol Monatsschr), vol. 178, Apr. 1992, pp. 297-300.
Lademann et al. "Nanoparticles-an efficient carrier for drug delivery into the hair follicles." *Eur J Pharm Biopharm*, 2007, 66:159-164.
Le Guevel, et al "Synthesis, Stabilization, and Functionalization of Silver Nanoplates for Biosensor Applications." J Phys Chem C, 113, 16380-16386. (Published Aug. 21, 2009).

(56) References Cited

OTHER PUBLICATIONS

Lloyd, et al. "Selective Photothermolysis of the Sebaceous Glands for Acne Treatment", Lasers in Surgery and Medicine, vol. 31, 2002, pp. 115-120.

Mallon et al. "The quality of life in acne: a comparison with general medical conditions using generic questionnaires." *Br J Dermatol*, 1999, 140:672-676.

Meidan, V.M. "Methods for quantifying intrafollicular drug delivery: a critical appraisal." *Expert Opin Drug Deliv*, 2010, 7:1095-1108.

Metraux, G. S. M. et al "Rapid Thermal Synthesis of Silver Nanoprisms with Chemically Tailorable Thickness." Advanced Materials, 2005, 17, No. 4, 412-415. (Published Feb. 23, 2005).

Mills, et al. "Ultraviolet Phototherapy and Photochemotherapy of Acne Vulgaris", Arch Dematol, vol. 114, No. 2, Feb. 1978 (Abstract, 2 pages).

Mitragotri et al. "Synergistic effect of low-frequency ultrasound and sodium lauryl sulfate on transdermal transport." *J Pharm Sci*, 2000, 89:892-900.

Mortensen et al. "In vivo skin penetration of quantum dot nanoparticles in the murine model: the effect of UVR." *Nano Lett*, 2008, 8:2779-2787.

Mutzhas, et al. "A New Apparatus with High Radiation Energy Between 320-460 nm: Physical Description and Dermatological Applications", The Journal of Investigative Dermatology, vol. 76, No. 1, Jan. 1981, pp. 42-47.

Nanni, C.A. and Alster, T.S. (1997). "Optimizing treatment parameters for hair removal using a topical carbon-based solution and 1064-nm Q-switched neodymium: YAG laser energy." *Arch Dermatol*, 1997, 133:1546-1549.

PCT/US2011/049464 International Search Report mailed Apr. 24, 2012.

Pento, et al. "Delta-Aminolevulinic Acid", Drugs of the Future, vol. 22, No. 1, 1997, pp. 11-17.

Phillips, al. et al "Medical Progress: Recent Advances in Dermatology", New England Journal of Medicine, vol. 326, No. 3, Jan. 1992, pp. 1-9 (167-176).

Polat et al. "Ultrasound-mediated transdermal drug delivery: Mechanisms, scope, and emerging trends." *J Control Release*, 2011, 152:330-348.

Rogers et al. "Hair removal using topical suspension-assisted Q-switched Nd: YAG and long-pulsed alexandrite lasers: A comparative study." *Dermatol Surg*, 1999, 25:844-844; discussion 848-850.

Sakamoto et al. "Photodynamic therapy for acne vulgaris: A critical review from basics to clinical practice: Part 1, Acne Vulgaris: When and why consider photodynamic therapy?" *Journal of the American Academy of Dermatology*, 2010, 63:183-193.

Sakamoto et al. "Photodynamic therapy for acne vulgaris: A critical review from basics to clinical practice: Part II. Understanding parameters for acne treatment with photodynamic therapy." *Journal of the Academy of Dermatology*, 2010, 63:195-211.

Schultz, et al. "The Chemorheology of Poly(vinyl alcohol)-Borate Gels." Macromolecules, vol. 2, No. 3, 281-285. (Published May-Jun. 1969).

Sellheyer, K. "Basal cell carcinoma: cell of origin, cancer stem cell hypothesis and stem cell markers." *Br J Dermatol*, 2011, 164:696-711.

Sellheyer, K. (2007). "Mechanisms of laser hair removal: could persistent photoepilation induce vitiligo or defects in wound repair?" *Dermatol Surg*, 2007, 33:055-1065.

Shershen et al. "Temperature-Sensitive Polymer—Nanoshell Composites for Photothermally Modulated Drug Delivery" *Journal of Biomedical Materials Research*; vol. 51, Issue 3, pp. 293-298 (Jun. 28, 2000).

Wainwright, Mark "Non-Porphyrin Photosensitizers in Biomedicine", Chemical Society Reviews, 1996, pp. 351-359.

West et al. "Applications of Nanotechnology to Biotechnology" *Current Opinion in Biotechnology 2000*, 11:215-217; Published Apr. 1, 2000.

Wong, S.Y., and Reiter, J.F. "Wounding mobilizes hair follicle stem cells to form tumors." *Proc Natl Aced Sci USA*, 2011, 108:4093-4098.

Xiong, et al. "Synthesis of silver nanoplates at high yields by slowing down the polyol reduction of silver nitrate with polyacrylamide." Journal of Materials Chemistry, 17, 2600-2602. (Published May 17, 2007).

Xue, et al. "pH-Switchable Silver Nanoprism Growth Pathways." Angew. Chem. Int. Ed., 46, 2036- 2038. (Published Feb. 13, 2007).

Zhao, W., and Karp, J.M. "Tumour targeting: Nanoantennas heat up." *Nat Mater*, 2009, 8:453-454.

U.S. Appl. No. 13/219,514, Compositions And Methods For Targeted Thermomodulation, filed Aug. 26, 2011.

U.S. Appl. No. 14/471,330, Thermal Treatment of a Pilosebaceous Unit With Metal Nanoparticles in Surfactant Containing Solutions, filed Aug. 28, 2014.

U.S. Appl. No. 14/471,319, Thermal Treatment of Acne With Coated Metal Nanoparticles, filed Aug. 28, 2014.

U.S. Appl. No. 14/471,434, Thermal Treatment of Acne With Nanoparticles With Coatings That Facilitate Selective Removal From the Skin Surface, filed Aug. 28, 2014.

U.S. Appl. No. 14/471,350, Thermal Treatment of Acne With Metal Nanoparticles in Surfactant Containing Solutions, filed Aug. 28, 2014.

U.S. Appl. No. 14/471,331, Hair Removal With Coated Metal Nanoparticles, filed Aug. 28, 2014.

U.S. Appl. No. 14/471,268, Hair Removal With Nanoparticles With Coatings That Facilitate Selective Removal From the Skin Surface, filed Aug. 28, 2014.

U.S. Appl. No. 14/471,367, Hair Removal With Metal Nanoparticles in Surfactant Containing Solutions, filed Aug. 28, 2014.

U.S. Appl. No. 14/471,402, Thermal Treatment of the Skin Surface With Coated Metal Nanoparticles, filed Aug. 28, 2014.

U.S. Appl. No. 14/471,437, Thermal Treatment of the Skin Surface With Nanoparticles With Coatings That Facilitate Selective Removal From the Skin Surface, filed Aug. 28, 2014.

U.S. Appl. No. 14/471,429, Thermal Treatment of the Skin Surface With Metal Nanoparticles in Surfactant Containing Solutions, filed Aug. 28, 2014.

U.S. Appl. No. 14/321,509, Ultrasound Delivery of Nanoparticles, filed Jul. 1, 2014.

U.S. Appl. No. 14/048,996, Silver Nanoplate Compositions And Methods, filed Oct. 8, 2013.

U.S. Appl. No. 14/603,904, Metastable Silver Nanoparticle Coomposites, filed Oct. 25, 2013.

Patent Interference document—General Hospital Responsive Motion 4 to Add a Claim in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 162, dated Mar. 4, 2016).

Patent Interference document—General Hospital List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 163, dated Mar. 4, 2016).

Patent Interference document—Sienna List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 83, dated Feb. 10, 2016).

Curriculum Vitae of Andrea Tao, Ph.D. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1003, filed on Feb. 10, 2016).

U.S. Appl. No. 61/402,305 and Provisional Cover Sheet. Listed as exhibits in interference between Senior Party U.S. Pat. No. 8,821,941, which shares common priority, assignee, and inventor-

(56) References Cited

OTHER PUBLICATIONS ship with the present application, and Junior Party U.S. Appl. No. 13/789,575 (U.S. Patent and Trademark Office, Patent Interference No. 106,037 (DK) Exhibit 1005 and 1029, filed on Feb. 10, 2016).
U.S. Appl. No. 61/422,612 and Provisional Cover Sheet. Listed as exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1006 and 1030, filed on Feb. 10, 2016).
U.S. Appl. No. 61/516,308 and Provisional Cover Sheet. Listed as exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1007 and 1031, filed on Feb. 10, 2016).
Appendix D of Jul. 28, 2015 General Hospital Corp. Section 202 Statement. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1011, filed on Feb. 10, 2016).
Jain, Prashant K. et al., J. Phys. Chem. B., 110:7238-7248 (2006). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1012, filed on Feb. 10, 2016).
Min, Younjin et al., Nature Materials, 7:527-538 (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1013, filed on Feb. 10, 2016).
Mastroianni, Alexander J. et al., J. Am. Chem. Soc. 131:8455-8459 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1014, filed on Feb. 10, 2016).
Zheng, Jiwen et al., Nano Letters, 6:105-1504 (2006). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1015, filed on Feb. 10, 2016).
Yan, Bo et al., Acs Nano, 3:1190-1202 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1016, filed on Feb. 10, 2016).
Shevchenko, Elena V. et al., Nature 439:55-59 (2006). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1017, filed on Feb. 10, 2016).
Kuzyk, Anton et al., Nature 483:311-314 (2012). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1018, filed on Feb. 10, 2016).
Pal, Suchetan et al., Angewandte Chemie Int'l Ed. 49:2700-2704 (2010). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1019, filed on Feb. 10, 2016).
Maye, Mathew M. et al., Nature Materials 8:388-391 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1020, filed on Feb. 10, 2016).
Feb. 24, 2014 Final Office Action in Sienna involved U.S. Appl. No. 14/020,481. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1021, filed on Feb. 10, 2016).
Mar. 27, 2014 Amendment in Sienna U.S. Appl. No. 14/020,599. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1022, filed on Feb. 10, 2016).
Jun. 24, 2014 Amendment in Sienna U.S. Appl. No. 14/020,481. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1023, filed on Feb. 10, 2016).
Sebacia Jun. 9, 2010 email and purchase order for NanoShells, from prosecution history (excluding references of record) of U.S. Appl. No. 13/789,575, namely an exhibit from a Suggestion for Declaration of Interference over US Publication 2014/0005593 with U.S. Appl. No. 14/020,481, now U.S. Pat. No. 8,821,941. This Exhibit MGH 1054 is from a Suggestion for Declaration of Interference and related documentation dated Jul. 28, 2015 (submission date to USPTO). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1025, filed on Feb. 10, 2016).
Dmochowski Declaration—submitted by the General Hospital in Section 202 Statement from prosecution history (excluding references of record) of U.S. Appl. No. 13/789,575, namely an exhibit from a Suggestion for Declaration of Interference over US Publication 2014/0005593 with U.S. Appl. No. 14/020,481, now U.S. Pat. No. 8,821,941. This Exhibit MGH 1001 is from a Suggestion for Declaration of Interference and related documentation dated Jul. 28, 2015 (submission date to USPTO). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1026, filed on Feb. 10, 2016).
GHC Supplemental Amendment and Response to Non-final Office Action submitted by the General Hospital from prosecution history (excluding references of record) of U.S. Appl. No. 13/789,575 dated Jan. 1, 2015 (submission date to USPTO). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1027, filed on Feb. 10, 2016.
Detail of concentration calculation performed by Dr. Andrea Tao. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1028, filed on Feb. 10, 2016).
Jan. 2016 CV of Professor Ivan Dmochowski. Listed as Junior Party exhibit in interference between Senior Party U.S. Pat. No. 8,821,941, which shares common priority, assignee, and inventorship with the present application, and Junior Party U.S. Appl. No.

(56) References Cited

OTHER PUBLICATIONS

13/789,575 (U.S. Patent and Trademark Office, Patent Interference No. 106,037 (DK) Exhibit 2027, filed on Feb. 10, 2016).
U.S. Appl. No. 61/636,381. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2031, filed on Feb. 10, 2016).
Sep. 9, 2013 Preliminary Amendment from the '481 Application. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2032, filed on Feb. 10, 2016).
Feb. 12, 2014 Interview Summary and Supplemental Amendment from the '481 Application. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2033, filed on Feb. 10, 2016).
Feb. 24, 2014 Final Office Action from the '481 Application. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2034, filed on Feb. 10, 2016).
Jun. 24, 2014 Request for Continued Examination with Amendment and Interview Summary from the '481 Application. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2035, filed on Feb. 10, 2016).
M. A. Garcia, Surface Plasmons in Metallic Nanoparticles: Fundamentals and Applications, 2011 J. Phys. D: Appl. Phys. 44 283001. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2036, filed on Feb. 10, 2016).
S. J. Oldenburg, J. B. Jackson, S. L. Westcott, and N. J. Halas, Infrared Extinction Properties of Gold Nanoshells, 75 Appl. Phys. Lett. 2897-2899 (1999). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2037, filed on Feb. 10, 2016).
X. Huang, I. El-Sayed, W. Qian, and M. Ei-Sayed, Cancer Cell Imaging and Photothermal Therapy in the Near-Infrared Region by Using Gold Nanorods, 128 J. Am. Chem. Soc., 2115-2120, 2006. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2038, filed on Feb. 10, 2016).
Todd James Harris Linkedin.com webpage. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2039, filed on Feb. 10, 2016).
Alice Ann Chen Kim Linkedin.com webpage. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2040, filed on Feb. 10, 2016).
X. Liu, M. Atwater, J. Wang, and Q. Huo, Extinction coefficient of gold nanoparticles with different sizes and different capping ligands, Colloids and Surfaces B: Biointerfaces 58 (2007) 3-7. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2041, filed on Feb. 10, 2016).
David Paramelle, Anton Sadovoy, Sergey Gorelik, Paul Free, Jonathan Hobley, David G. Fernig, A Rapid Method to Estimate the Concentration of Citrate Capped Silver Nanoparticles from UV-Visible Light Spectra, 139, Analyst, 4855-4861 (2014). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2042, filed on Feb. 10, 2016).
David Paramelle, Anton Sadovoy, Sergey Gorelik, Paul Free, Jonathan Hobley, David G. Fernig, *Supplementary Information* A Rapid Method to Estimate the Concentration of Citrate Capped Silver Nanoparticles from UV-Visible Light Spectra, Electronic Supplementary Material (ESI) for Analyst. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2043, filed on Feb. 10, 2016).
Heng Deng, Yanqi Zhong, Meihong Du, Qinjun Liu, Zhanming Fan, Fengying Dai, and Xin Zhang, Theranostic Self-Assembly Structure of Gold Nanoparticles for NIR Photothermal Therapy and X-Ray Computed Tomography Imaging, 4 Theranostics 904-918 (2014). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2044, filed on Feb. 10, 2016).
Silicon, From Wikipedia, the free encyclopedia, https://en.wikipedia.org/wiki/Silicon viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2045, filed on Feb. 10, 2016).
What Is the Most Conductive Element? Maximum Electrical Conductivity, http://chemistry.about.com/od/elements/f/What-Is-The-Most-Conductive-Element.htm viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2046, filed on Feb. 10, 2016).
Prashant K. Jain, Kyeong Seok Lee, Ivan H. El-Sayed, and Mostafa A. El-Sayed. Calculated absorption and scattering properties of gold nanoparticles of different size, shape, and composition: applications in biological imaging and biomedicine. 110 J. Phys. Chem. B, 7238-7248 (2006). Listed as Junior Party exhibit in interference between Senior Party U.S. Pat. No. 8,821,941, which shares common priority assignee, and inventorship with the present application, and Junior Party U.S. Appl. No. 13/789,575 (U.S. Patent and Trademark Office, Patent Interference No. 106,037 (DK) Exhibit 2047, filed on Feb. 10, 2016).
Gold Nanoparticles: Properties and Applications, http://www.sigmaaldrich.com/materials-science/nanomaterials/goldnanoparticles.html viewed Jan. 27, 2016. Listed as Junior Party exhibit in interference between Senior Party U.S. Pat. No.

(56) References Cited

OTHER PUBLICATIONS 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2048, filed on Feb. 10, 2016).
A. Smith, M. Mancini & S. Nie, Bioimaging: Second Window for In Vivo Imaging, 4 Nature Nanotechnology, 710-711 (2009). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2049, filed on Feb. 10, 2016).
Roger Grant and Clair Grant, Grant & Hackh'S Chemical Dictionary, 374 (1987 5th ed.). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2050, filed on Feb. 10, 2016).
Hair follicle, From Wikipedia, the free encyclopedia, https://en.wikipedia.org/wiki/Hair_follicle viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (Dk) Exhibit 2051, filed on Feb. 10, 2016).
Lumenis LightSheer ET brochure, http://partnerzone.lumenis.com/DesktopModules/Bring2mind/DMX/Download.aspx?Command=Core_Download&EntryId=3598&language=en-US&PortalId=0&TabId=386, viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2052, filed on Feb. 10, 2016).
Lumenis LightSheer ET webpage, http://www.lumenis.com/Solutions/Aesthetic/Products/LightSheer-ET, viewed Jan. 27, 2017 [sic] (2016). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2053, filed on Feb. 10, 2016).
nanoComposix Plasmonics and Nanophotonics, http://nanocomposix.com/pages/plasmonics-and-nanophotonics viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2054, filed on Feb. 10, 2016).
Conjugated Nanopartz™ Gold Nanoparticles, http://www.nanopartz.com/invitro_gold_nanoparticles.asp viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2055, filed on Feb. 10, 2016).
660 nm Resonant Gold Nanorods, http://nanocomposix.com/collections/goldnanorods/products/660-nm-resonant-gold-nanorods#example-coa viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2056, filed on Feb. 10, 2016).
Jian Hua Sun, Ming Yun Guan, Tong Ming Shang, Cui Ling Gao & Zheng Xu, Synthesis and Optical Properties of Triangular Gold Nanoplates with Controllable Edge Length, 53 Sci China Chem 9 2033-2038 (2010). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2057, filed on Feb. 10, 2016).
660 nm Resonant Gold Nanoshells, http://50.87.149.212/_Specification%20Sheets/Gold%20Nanoshells/660nm_Au_Nanoshells_PEG_NX_High_KJW2013_CoA.pdf?0311116 viewed Jan. 31, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2058, filed on Feb. 10, 2016).
Yugang Sun, Brian Mayers, and Younan Xia, Metal Nanostructures with Hollow Interiors, 15 Adv. Mater. 2003, 7±8, 641-646. Listed as Junior Party exhibit in interference between Senior Party U.S. Pat. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2059, filed on Feb. 10, 2016).
Ling Tong, Qingshan Wei, Alexander Wei, and Ji-Xin Cheng, Gold Nanorods as Contrast Agents for Biological Imaging: Optical Properties, Surface Conjugation, and Photothermal Effects, 85 Photochem Photobiol. 21-32 (2009). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2035, filed on Feb. 10, 2016).
Strem Gold Nanorods, 96-1530 Gold Nanorods Kit, http://www.strem.com/uploads/resources/documents/gold_nanorods_kit.pdf viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2061, filed on Feb. 10, 2016).
Hui Wang, Daniel W. Brandi, Fei Le, Peter Nordlander, and Naomi J. Halas, Nanorice: A Hybrid Plasmonic Nanostructure, 6 Nano Lett., 4, 827-832 (2006). Listed as Junior Party exhibit in interference between Senior Party U.S. Pat. No. 8,821,941, which shares common priority, assignee, and inventorship with the present application, and Junior Party U.S. Patent and Tradmark Office, Patent Interference No. 106,037 (DK) Exhibit 2062, filed on Feb. 10, 2016).
Nanopartz™ Gold Nanowires, http://www.nanopartz.com/bare_gold_nanowires.asp viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2063, filed on Feb. 10, 2016).
Priya Vasanthakumar, Optics and spectroscopy of gold nanowires, (Apr. 18, 2014) (unpublished Doctoral Thesis, Universite Paris-Sud, and Università di Pisa) https://tel.archives-ouvertes.fr/tel-00922344/document viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2064, filed on Feb. 10, 2016).
Gold Nanobipyramids, http://www.nanoseedz.com/Gold_Nanobipyramids_en.html viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2065, filed on Feb. 10, 2016).
Zhirui Guo, Xu Fan, Lianke Liva, Zhiping Bian, Chunrong Gu, Yu Zhang, Ning Gub, Di Yang, and Jinan Zhang, Achieving

(56) References Cited

OTHER PUBLICATIONS

High-Purity Colloidal Gold Nanoprisms and Their Application as Biosensing Platforms, 348(1): J Colloid Interface Sci. 29-36, (2010). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2066, filed on Feb. 10, 2016).
Gold Nanostars, http://www.nanoseedz.com/Au_nanostar.html viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2067, filed on Feb. 10, 2016).
nanoComposix Silver Nanoplates, http://nanocomposix.com/collections/silvernanoplates viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2068, filed on Feb. 10, 2016).
J. B. Jackson and N. J. Halas, Silver Nanoshells: Variations in Morphologies and Optical Properties, 105, J. Phys. Chem. B, 2743-2746 (2001). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2069, filed on Feb. 10, 2016).
Satarupa Pattanayak, Amiya Priyam, and Pradip Paik, Facile Tuning of Plasmon Bands in Hollow Silver Nanoshells Using Mild Reductant and Mild Stabilizer, 42, Dalton Trans., 10597-10607 (2013). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2070, filed on Feb. 10, 2016).
Nikhil R. Jana, Latha Gearheart and Catherine J. Murphy, Wet Chemical Synthesis of Silver Nanorods and Nanowires of Controllable Aspect Ratio, Chem. Commun., 617-618 (2001). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2071, filed on Feb. 10, 2016).
Benjamin J. Wiley, Yeechi Chen, Joseph M. McLellan, Yujie Xiong, Zhi-Yuan Li, David Ginger, and Younan Xia, Synthesis and Optical Properties of Silver Nanobars and Nanorice, 7, Nano Lett., 4, 1032-1036 (2007). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2072, filed on Feb. 10, 2016).
nanoComposix, Silver Nanoparticles: Optical Properties, http://nanocomposix.com/pages/silver-nanoparticles-optical-properties viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2073, filed on Feb. 10, 2016).
Nasser A. M. Barakat, Kee-Do Woo, Muzafar A. Kanjwal, Kyung Eun Choi, Myung Seob Khil, and Hak Yong Kim, Surface Plasmon Resonances, Optical Properties, and Electrical Conductivity Thermal Hystersis of Silver Nanofibers Produced by the Electrospinning Technique, 24 Langmuir 11982-11987 (2008). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2074, filed on Feb. 10, 2016).
Xiaoming Sun and Yadong Li, Cylindrical Silver Nanowires: Preparation, Structure, and Optical Properties, 17, Adv. Mater., 2626-2630 (2005). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2075, filed on Feb. 10, 2016).
Benjamin J. Wiley, Yujie Xiong, Zhi-Yuan Li, Yadong Yin, and Younan Xia, Right Bipyramids of Silver: A New Shape Derived from Single Twinned Seeds, 6, Nano Lett., 4, 765-768 (2006). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2076, filed on Feb. 10, 2016).
Gabriella S. Métraux and Chad A. Mirkin, Rapid Thermal Synthesis of Silver Nanoprisms with Chemically Tailorable Thickness, 17, Adv. Mater., 412-415 (2005). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2077, filed on Feb. 10, 2016).
Adianez Garcia-Leis, Jose Vicente Garcia-Ramos, and Santiago Sanchez-Cortes, Silver Nanostars with High SERS Performance, 117, J. Phys. Chem. C, 7791-7795 (2013). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2078, filed on Feb. 10, 2016).
Perry's Chemical Engineers' Handbook, (Robert H. Perry, Don Green, & James O. Maloney eds. 6th ed. 1984). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2079, filed on Feb. 10, 2016).
nanoComposix, 550 nm Resonant Silver Nanoplates, http://nanocomposix.com/collections/silver-nanoplates/products/550-nmresonant-silver-nanoplates viewed Jan. 27, 2016. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Tradmark Office, Patent Interference No. 106,037 (DK) Exhibit 2080, filed on Feb. 10, 2016).
nanoComposix, Certificate of Analysis Examples of Silica Shelled 70 nm Silver Nanospheres, http://50.87.149.212/_Specification%20Sheets/Silica-Coated%20Silver%20Spec%20Sheets/AG70-Si20-KJW1618A.pdf?0271031 viewed Jan. 27, 2017 [sic] (2016). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2081, filed on Feb. 10, 2016).
CRC Handbook of Chemistry and Physics, 88th Edition (David R. Lide, ed. 2007). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2083, filed on Feb. 10, 2016).

(56) References Cited

OTHER PUBLICATIONS

Cytodiagnostics webpage; http://www.cytodiagnostics.com/store/pc/Gold-Nanoparticle-Properties-d2.htm. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2085, filed on Feb. 10, 2016).
Jon A. Schwartz, Anil M. Shetty, Roger E. Price, R. Jason Stafford, James C. Wang, Rajesh K. Uthamanthil, Kevin Pham, Roger J. McNichols, Chris L. Coleman, and J. Donald Payne, Feasibility Study of Particle-Assisted Laser Ablation of Brain Tumors in Orthotopic Canine Model, 69 Cancer Res., 1659-1667 (2009). Listed as Junior Party exhibit in interference between Senior Party U.S. Pat. No. 8,821,941, which shares Party U.S. Appl. No. 13/789,575 (U.S. Patent and Trademark Office, Patent Interference No. 106,037 (DK) Exhibit 2087, file don Feb. 10, 2016.
Third Declaration of Ivan J. Dmochowski. Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (Dk) Exhibit 2089, filed on Mar. 4, 2016).
Todd J. Harris, Geoffrey von Maltzahn, Austin M. Derfus, Erkki Ruoslahti, and Sangeeta N. Bhatia, Proteolytic Actuation of Nanoparticle, 45 Angew. Chem. Int. Ed., 3161-3165 (2006). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2090, filed on Mar. 4, 2016).
Chung Hang J. Choi, Christopher A. Alabi, Paul Webster, and Mark E. Davis, Mechanism of active targeting in solid tumors with transferrin-containing gold nanoparticles, 107 PNAS, 1235-1240 (2010). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2091, filed on Mar. 4, 2016).
Liang Gao, Tegy J. Vadakkan, and Vengadesan Nammalvar, Nanoshells for In Vivo Imaging Using Two-photon Excitation Microscopy, 22 Nanotechnology, (2011). Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2092, filed on Mar. 4, 2016).
Patent Interference document—Sienna Priority Statement in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 86, dated Feb. 10, 2016) (Material Not Open to Public, Do Not Scan).
Patent Interference document—General Hospital Priority Statement in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 155, dated Feb. 10, 2016) (Material Not Open to Public, Do Not Scan).
Patent Interference document—Sienna Opposition 1 against Junior Party Motion 1 on Benefit of the Filing Date of U.S. Appl. No. 61/636,381 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 200, dated Apr. 8, 2016).
Patent Interference document—Sienna Opposition 2 against Junior Party Motion 2 on Written Description and Enablement Under 35 U.S.C. § 112, First Paragraph in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 220, dated Apr. 8, 2016).
Patent Interference document—Sienna Opposition 3 against Junior Party Motion 3 on Accorded Benefit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 201, dated Apr. 8, 2016).
Patent Interference document—Sienna Opposition 4 against Junior Party Motion 4 on Adding a Claim in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 221, dated Apr. 8, 2016).
Patent Interference document—Sienna List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 171, dated Apr. 8, 2016).
Patent Interference document—Second Declaration of Andrea Tao, Ph.D., in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1032, filed on Apr. 8, 2016).
Patent Interference document—First Declaration of Chad Mirkin, Ph.D. in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1034, filed on Apr. 8, 2016).
Patent Interference document—Curriculum Vitae of Chad Mirkin, Ph.D. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1035, filed on Feb. 10, 2016).
Patent Interference document—Summary report showing results of the computer simulation of the composition of 10 × 30 nm gold nanorods [895.1 nm]. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1046, filed on Apr. 8, 2016).
Patent Interference document—Summary report showing results of the computer simulation of the composition of 300 nm gold nanoshells [885.8 nm and 1281 nm]. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1047, filed on Apr. 8, 2016).
Patent Interference document—Summary report showing results of the computer simulation of the composition of 30 × 200 nm silver nanoplates [1059 nm]. Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1048, filed on Apr. 8, 2016).
Patent Interference document—Summary report showing results of the computer simulation of the composition of 15 × 30 nm gold nanorods [901 nm]. Listed as exhibit in interference .between Senior Party U.S. Pat. No. 8,821,941, which shares common priority, assignee, and inventorship with the present application, and

(56) References Cited

OTHER PUBLICATIONS

Junior Party U.S. Appl. No. 13/789,575 (U.S. Patent and Trademark Office, Patent Interference No. 106,037 (DK) Exhibit 1049, filed on Apr. 8, 2016).
Gault, D.T. et al., "The Removal of Unwanted Hair Using a Ruby Laser," British J Plastic Surgery, 52:173-177 (1999). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1036, filed on Apr. 8, 2016).
Yoo, H. et al., NIH Public Access Author Manuscript, published in final edited form in Nano Letters, 9:3038-3041 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1038, filed on Apr. 8, 2016).
Skrabalak, S.E. et al., Nature Protocols, 2:2182-2190 (2007). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1039, filed on Apr. 8, 2016).
Millstone, J.E. et al., J Amer. Chem. Society, 127:5312-5313 (2005). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1040, filed on Apr. 8, 2016).
Kim, F. et al., J Amer. Chem. Society, 124:14316-14317 (2002). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1041, filed on Apr. 8, 2016).
Rodriguez-Lorenzo, L., J Physical Chem., 114:7336-7340 (2010). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1042, filed on Apr. 8, 2016).
Von Maltzahn, G. et al., Cancer Research, 69:3892-3900 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1043, filed on Apr. 8, 2016).
Bost, W. et al., IFMBE Proc., 25/II, 529-532 (2009). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1044, filed on Apr. 8, 2016).
Chang, W. et al., PNAS, 107:2781-2786 (2010). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1045, filed on Apr. 8, 2016).
Jin, Rongchao et al., Science, 294:1901-1903 (2001). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1050, filed on Apr. 8, 2016).
Nikoobakht, B. et al., Chem. Mater., 15:1957-1962 (2003). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1051, filed on Apr. 8, 2016).
Nanopartz Application Note—Nsol Gold Nanorods for use in organic solvents (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1052, filed on Apr. 8, 2016).
Nanopartz Product Profile—Nsol gold nanorods (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1053, filed on Apr. 8, 2016).
Nanopartz Product Profile—Gold Nanorodz (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1054, filed on Apr. 8, 2016).
Nanopartz Product Profile—Ntracker (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1055, filed on Apr. 8, 2016).
Nanopartz Technical Note—Photothermal Characteristics of Gold Nanorods—TN802 (2008). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1056, filed on Apr. 8, 2016).
Jin, Rongchao et al., Nature, 425:487-490 (Oct. 2, 2003). Listed as exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1059, filed on Apr. 8, 2016).
Patent Interference document—Junior Party Opposition 1 against Sienna Motion 1 for judgment that GHC's claims are unpatentable under 35 U.S.C. § 112, first paragraph in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 222, dated Feb. 10, 2016).
Patent Interference document—Junior Party Opposition 2 against Sienna Substantive Motion 2 to be accorded benefit of the filing dates of Sienna U.S. Appl. Nos. 61/402,305; 61/422,612; and 61/516,308 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 223, dated Feb. 10, 2016).
Patent Interference document—Junior Party List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 224, dated Apr. 8, 2016).
Patent Interference document—Fourth Declaration of Ivan J. Dmochowski, Ph. D.—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2093, filed on Apr. 8, 2016).
Patent Interference document—Ms. Pulsipher's Notebook Pages (dated Mar. 22, 2016 to Apr. 1, 2016)—Listed as Junior Party exhibit in interference between Senior Party U.S. Pat. No. 8,821,941, which shares common priority, assignee, and inventor-

(56) References Cited

OTHER PUBLICATIONS ship with the present application, and Junior Party U.S. Appl. No. 13/789,575 (U.S. Patent and Trademark Office, Patent Interference No. 106,037 (DK) Exhibit 2095, filed on Apr. 8, 2016).
Patent Interference document—Transcript from the Mar. 23, 2016 Cross-Examination of Dr. Andrea Tao—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2114, filed on Apr. 8, 2016).
Certificates of Analysis from Nanospectra from Dec. 2010 and 2016—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2094, filed on Apr. 8, 2016).
Leon R. Hirsch, R. Jason Stafford, J. A. Bankson, Scott R. Sershen, B. Rivera, R. E. Price, John D. Hazle, Naomi J. Halas, and Jennifer L. West, Nanoshellmediated near-infrared thermal therapy of tumors under magnetic resonance guidance, PNAS 2003 100 (23) 13549-13554 (2003)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2098, filed on Apr. 8, 2016).
Sienna Labs, "Management", http://www.siennalabs.com/management/ (viewed on Apr. 7, 2015)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2111, filed on Apr. 8, 2016).
Todd J. Harris, Geoffrey von Maltzahn, and Sangeeta N. Bhatia, Multifunctional Nanoparticles for Cancer Therapy, in Nanotechnology for Cancer Therapy, 59-75 (Mansoor M. Amiji ed., 2006)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2113, filed on Apr. 8, 2016).
Takumi Hawa, Brian Henz and Michael Zachariah (2007). Computer Simulation of Nanoparticle Aggregate Fracture. MRS Proceedings, 1056, 1056-HH08-45 doi:10.1557/PROC-1056-HH08-45.—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2117, filed on Apr. 8, 2016).
Geoffrey von Maltzahn, Todd J Harris, Ji-Ho Park, Dal-Hee Min, Alexander J Schmidt, Michael J. Sailor, and Sangeeta N. Bhatia, Nanoparticle Self-Assembly Gated by Logical Proteolytic Triggers, 129(19), J Am Chem Soc., 6064-6065, 6065 (2007)—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2118, filed on Apr. 8, 2016).
Piotr Grodzinski, nanoUtah slides, Oct. 2007—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2120, filed on Apr. 8, 2016).
Nikhil R. Jana, Shape Effect in Nanoparticle Self-Assembly, Angew. Chem. Int. Ed. 43, 1536-1540 (2004).—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2122, filed on Apr. 8, 2016).
Patent Interference document—Sienna Reply 1 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 230, dated May 20, 2016).
Patent Interference document—Sienna Reply 2 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 231, dated May 20, 2016).
Patent Interference document—Sienna List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 232, dated May 20, 2016).
Patent Interference document—Transcript from the May 2nd, 2016 Cross-Examination of Dr. Chad Mirkin—Listed as Senior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 1061, filed on May 20, 2016).
Patent Interference document—Junior Party Reply 1 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 247, dated May 20, 2016).
Patent Interference document—Junior Party Reply 2 in interference between Senior Party U.S. Pat. 8,821,941, which shares common priority, assignee, and inventorship with the present application, and Junior Party U.S. Appl. No. 13/789,575 (U.S. Patent and Trademark Office, Patent Interference No. 106,037 (DK) Paper 248, dated May 20, 2016).
Patent Interference document—Junior Party Reply 3 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 249, dated May 20, 2016).
Patent Interference document—Junior Party Reply 4 in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 246, dated May 20, 2016).
Patent Interference document—Junior Party List of Exhibits in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Paper 245, dated May 20, 2016).
Kelly Y. Kim, MA, Nanotechnology platforms and physiological challenges for cancer therapeutics, Nanomedicine: Nanotechnology, Biology, and Medicine 3 (2007) 103-110—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2124 filed on May 20, 2016).
Sandani Samarajeewa, et al., Programmed hydrolysis of nanoassemblies by electrostatic interaction-mediated enzymatic-degradation, Chem Commun (Camb). Jan. 28, 2014 ; 50(8): 968-970—Listed as Junior Party exhibit in interference between Senior Party U.S. Pat. No. 8,821,941, which shares common priority, assignee, and inventorship with the present application, and Junior Party U.S.

(56) References Cited

OTHER PUBLICATIONS

Appl. No. 13/789,575 (U.S. Patent and Trademark Office, Patent Interference No. 106,037 (DK) Exhibit 2125 filed on May 20, 2016).
Jeffery G. Sheldon, Patent Applications for the Chemical Invention, in How to Write a Patent Application, PLI, 2014—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2130 filed on May 20, 2016).
Comsol AB, Finite Element Mesh Refinement, www.comsol.com/multiphysics/mesh-refinement, viewed May 18, 2016—Listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK) Exhibit 2131 filed on May 20, 2016).
Comsol Multiphysics User's Guide version 4.3, (2012) (Excerpts of the 1,292 page document, including title, table of contents, and sections cited by Junior Party in Reply 2 and Reply 3)—Full 1,292 page document listed as Junior Party exhibit in interference between Senior Party U.S. Pat. No. 8,821,941, which shares common priority, assignee, and inventorship with the present application, and Junior Party U.S. Appl. No. 13/789,575 (U.S. Patent and Trademark Office, Patent Interference No. 106,037 (DK), submitted by Junior Party as Exhibit 2132A and 2132B filed on May 20, 2016).
U.S. Appl. No. 13/219,514, Compositions and Methods for Targeted Thermomodulation, Aug. 26, 2011.
U.S. Appl. No. 14/020,423, Thermal Treatment of Acne With Nanoparticles, Sep. 6, 2013.
U.S. Appl. No. 14/020,387, Thermal Treatment of the Skin Surface With Nanoparticles, Sep. 6, 2013.
U.S. Appl. No. 14/020,481, Hair Removal With Nanoparticles, Sep. 6, 2013.
U.S. Appl. No. 14/020,599, Thermal Treatment of a Pilosebaceous Unit With Nanoparticles, Sep. 6, 2013.
U.S. Appl. No. 14/471,348, Thermal Treatment of a Pilosebaceous Unit With Coated Metal Nanoparticles, Aug. 28, 2014.
U.S. Appl. No. 14/471,377, Thermal Treatment of a Pilosebaceous Unit With Nanoparticles With Coatings That Facilitate Selective Removal From the Skin Surface, Aug. 28, 2014.
U.S. Appl. No. 14/471,330, Thermal Treatment of a Pilosebaceous Unit With Metal Nanoparticles in Surfactant Containing Solutions, Aug. 28, 2014.
U.S. Appl. No. 14/471,319, Thermal Treatment of Acne With Coated Metal Nanoparticles, Aug. 28, 2014.
U.S. Appl. No. 14/471,434, Thermal Treatment of Acne With Nanoparticles With Coatings That Facilitate Selective Removal From the Skin Surface, Aug. 28, 2014.
U.S. Appl. No. 14/471,350, Thermal Treatment of Acne With Metal Nanoparticles in Surfactant Containing Solutions, Aug. 28, 2014.
U.S. Appl. No. 14/471,331, Hair Removal With Coated Metal Nanoparticles, Aug. 28, 2014.
U.S. Appl. No. 14/471,268, Hair Removal With Nanoparticles With Coatings That Facilitate Selective Removal From the Skin Surface, Aug. 28, 2014.
U.S. Appl. No. 14/471,367, Hair Removal With Metal Nanoparticles in Surfactant Containing Solutions, Aug. 28, 2014.
U.S. Appl. No. 14/471,402, Thermal Treatment of the Skin Surface With Coated Metal Nanoparticles, Aug. 28, 2014.
U.S. Appl. No. 14/471,437, Thermal Treatment of the Skin Surface With Nanoparticles With Coatings That Facilitate Selective Removal From the Skin Surface, Aug. 28, 2014.
U.S. Appl. No. 14/471,429, Thermal Treatment of the Skin Surface With Metal Nanoparticles in Surfactant Containing Solutions, Aug. 28, 2014.
U.S. Appl. No. 14/321,509, Ultrasound Delivery of Nanoparticles, Jul. 1, 2014.
Australia 2011293132 Compositions and Methods for Targeted Thermomodulation, Aug. 26, 2011.
Australia 2016200848, Compositions and Methods for Targeted Thermomodulation, Aug. 26, 2011.
Brazil 102013004902-6, Compositions and Methods for Targeted Thermomodulation, Feb. 28, 2013.
Canada 2,806,592, Compositions and Methods for Targeted Thermomodulation, Aug. 26, 2011.
China 201180041302.8, Compositions and Methods for Targeted Thermomodulation, Aug. 26, 2011.
Europe 11820765.3, Compositions and Methods for Targeted Thermomodulation, Aug. 26, 2011.
Israel 224390, Compositions and Methods for Targeted Thermomodulation, Aug. 26, 2011.
India 1651/DELNP/2013, Compositions and Methods for Targeted Thermomodulation, Aug. 26, 2011.
Japan 513047246, Compositions and Methods for Targeted Thermomodulation, Aug. 26, 2011.

\* cited by examiner

Epidermal　　　Dermal (870 μm deep)

plane 1　　plane 2

THERMAL TREATMENT OF THE SKIN SURFACE WITH COATED METAL NANOPARTICLES

CROSS REFERENCE AND INCORPORATION BY REFERENCE TO ANY PRIORITY APPLICATIONS

This application is a continuation of U.S. patent application Ser. No. 14/020,387 filed Sep. 6, 2013, which is a continuation of U.S. patent application Ser. No. 13/219,514 filed Aug. 26, 2011, which claims the benefit of priority under 35 U.S.C. §119(e) of U.S. Provisional Application Nos. 61/402,305 filed Aug. 27, 2010; 61/422,612 filed Dec. 13, 2010, and 61/516,308 filed Apr. 1, 2011; each of which is hereby incorporated by reference in its entirety. Any and all applications for which a foreign or domestic priority claim is identified in the Application Data Sheet as filed with the present application are hereby incorporated by reference under 37 CFR 1.57.

PARTIES OF JOINT RESEARCH AGREEMENT

The invention described herein was created subject to a Joint Research Agreement between Sienna Labs, Inc. and Nanocomposix, Inc.

BACKGROUND

1. Field of the Invention

The field of the invention is nanoparticles and/or photoactive compounds for use in cosmetic, diagnostic and/or therapeutic procedures.

2. Description of the Related Art

Laser treatments of the skin are widely known and have been highly touted for therapeutic and cosmetic utility. Therapeutically, potential uses for laser skin therapy include laser ablation of cancerous cells in cancer patients and laser ablation of damaged tissue in burn victims. Cosmetic applications for laser skin therapy are much more numerous, and include hair removal/reduction, treatment of dyschromia, shrinking of the skin following operations such as liposuction, acne treatment, chemical or physical abrasion of unwanted markings on the skin, surgical treatments including nose reduction and face- and neck-lifts, and other aesthetic skin remodeling purposes.

SUMMARY

Despite the promise of laser therapy for skin therapeutics and cosmetics, current laser procedures have limited efficacy, requiring prohibitive numbers of repeated treatments and driving increased costs. Suboptimal laser treatments also have limited specificity, resulting in debilitating clinical side effects, such as non-specific skin damage, skin irritation and scarring.

Light-based hair removal systems suffer from particularly low rates of efficacy at removing light hair (vellus, blonde, gray, red hair). Multiple (even 6 or more) treatments are insufficient to achieve a therapeutic result in blonde-gray- or red-haired patients, even with the use of topically applied chromophores such as carbon. In addition to light hair removal, thermoablative technology has untapped potential in the fields of wound healing, tissue remodeling, vascular repair, and acne treatment.

Acne *vulgaris* results from obstruction of the pilosebaceous unit, consisting of the hair shaft, hair follicle, sebaceous gland and erector pili muscle, which leads to accumulation of sebum oil produced from the sebaceous gland and the subsequent colonization of bacteria within the follicle. Microcomedones formed as a result of accumulated sebum progress to non-inflamed skin blemishes (white/blackheads), or to skin blemishes which recruit inflammatory cells and lead to the formation of papules, nodules and pus-filled cysts. The sequelae of untreated acne *vulgaris* often include hyperpigmentation, scarring and disfiguration, as well as significant psychological distress. Therefore, acne treatments seek broadly to reduce the accumulation of sebum and microorganisms within follicles and the sebaceous gland.

Methods involving light and lasers are promising for the treatment skin disorders, but are still insufficiently effective. Ultraviolet (UV)/blue light is approved by the FDA for the treatment of mild to moderate acne only, due to its anti-inflammatory effects mediated on skin cells (keratinocytes), potentially through the action of endogenous porphyrin photosensitizers within follicles. Exogenous porphyrin precursors such as 5-aminolevulinic acid (5-ALA) have been formulated for topical or oral delivery and shown to accumulate within sebaceous follicles, absorb photons from red light exposure and form reactive oxygen species that directly damage cellular membranes and proteins. This procedure combining porphyrin application and high intensity red light, termed 'photodynamic therapy', has been demonstrated to reduce sebum production and acne by 50% for 20 weeks post-irradiation. However, high intensity energies (50-150 $J/cm^2$) are required to damage sebaceous gland skin structures, and transdermal porphyrin penetration leads to off-target side-effects which include sensitivity to light, pain, inflammation, hyper/hypo-pigmentation, and permanent scarring.

For laser therapy to achieve its full utility in the treatment of human skin disorders, methods to locally induce photo-destruction in skin structures without affecting surrounding tissues must be achieved.

Provided herein, in certain embodiments, are new compositions and methods useful in the targeted thermomodulation of target cell populations and target tissues, for the purposes of cosmetic treatments and the treatment and prevention of chronic and acute diseases and disorders.

In one aspect, described herein are compositions of matter. For example, in one embodiment, provided is a composition comprising a cosmetically acceptable carrier and a plurality of plasmonic nanoparticles in an amount effective to induce thermomodulation in a target tissue region with which the composition is topically contacted.

In some embodiments, the composition comprises plasmonic nanoparticles that are activated by exposure to energy delivered from a nonlinear excitation surface plasmon resonance source to the target tissue region. In further or additional embodiments, described herein are compositions comprising at least one plasmonic nanoparticle that comprises a metal, metallic composite, metal oxide, metallic salt, electric conductor, electric superconductor, electric semiconductor, dielectric, quantum dot or composite from a combination thereof. In further or additional embodiments, provided herein is a composition wherein a substantial amount of the plasmonic particles present in the composition comprise geometrically-tuned nanostructures. In certain embodiments, provided herein is a composition wherein plasmonic particles comprise any geometric shape currently known or to be created that absorb light and generate plasmon resonance at a desired wavelength, including nanoplates, solid nanoshells, hollow nanoshells, nanorods, nanorice, nanospheres, nanofibers, nanowires, nanopyramids, nanoprisms, nanostars or a combination thereof. In yet additional embodiments, described herein is a composition wherein the plasmonic particles comprise silver, gold, nickel, copper, titanium, silicon, galadium, palladium, platinum, or chromium.

In some embodiments, provided herein is a composition comprising a cosmetically acceptable carrier that comprises an additive, a colorant, an emulsifier, a fragrance, a humectant, a polymerizable monomer, a stabilizer, a solvent, or a surfactant. In one embodiment, provided herein is a composition wherein the surfactant is selected from the group consisting of: sodium laureth 2-sulfate, sodium dodecyl sulfate, ammonium lauryl sulfate, sodium octech-1/deceth-1 sulfate, lipids, proteins, peptides or derivatives thereof. In one embodiment, provided is a composition wherein a surfactant is present in an amount between about 0.1 and about 10.0% weight-to-weight of the carrier. In yet another embodiment, the solvent is selected from the group consisting of water, propylene glycol, alcohol, hydrocarbon, chloroform, acid, base, acetone, diethyl-ether, dimethyl sulfoxide, dimethylformamide, acetonitrile, tetrahydrofuran, dichloromethane, and ethylacetate. In one embodiment, the composition comprises plasmonic particles that have an optical density of at least about 1 O.D. at one or more peak resonance wavelengths.

In further or additional embodiments, described herein is a composition wherein plasmonic particles comprise a hydrophilic or aliphatic coating, wherein the coating does not substantially adsorb to skin of a mammalian subject, and wherein the coating comprises polyethylene glycol, silica, silica-oxide, polyvinylpyrrolidone, polystyrene, a protein or a peptide. In yet an additional embodiment, the thermomodulation comprises damage, ablation, thermoablation, lysis, denaturation, deactivation, activation, induction of inflammation, activation of heat shock proteins, perturbation of cell-signaling or disruption to the cell microenvironment in the target tissue region. Still further, in certain presentations the target tissue region comprises a sebaceous gland, a component of a sebaceous gland, a sebocyte, a component of a sebocyte, sebum, or hair follicle infundibulum. In further embodiments, the target tissue region comprises a bulge, a bulb, a stem cell, a stem cell niche, a dermal papilla, a cortex, a cuticle, a hair sheath, a medulla, a *pylori* muscle, a Huxley layer, or a Henle layer.

In another aspect, described herein are methods of performing targeted ablation of tissue. For example, in one embodiment, provided is a method for performing targeted ablation of a tissue to treat a mammalian subject in need thereof, comprising the steps of i) topically administering to a skin surface of the subject the composition of claim 1; ii) providing penetration means to redistribute the plasmonic particles from the skin surface to a component of dermal tissue; and iii) causing irradiation of the skin surface by light. In further or additional embodiments, provided is a method wherein the light source comprises excitation of mercury, xenon, deuterium, or a metal-halide, phosphorescence, incandescence, luminescence, light emitting diode, or sunlight. In still further or additional embodiments, provided is a method wherein the penetration means comprises high frequency ultrasound, low frequency ultrasound, massage, iontophoresis, high pressure air flow, high pressure liquid flow, vacuum, pre-treatment with fractionated photothermolysis or dermabrasion, or a combination thereof. In still further embodiments, provided is a method wherein the irradiation comprises light having a wavelength of light between about 200 nm and about 10,000 nm, a fluence of about 1 to about 100 joules/cm$^2$, a pulse width of about 1 femtosecond to about 1 second, and a repetition frequency of about 1 Hz to about 1 THz.

In a further aspect, provided herein is a composition comprising a cosmetically acceptable carrier, an effective amount of sodium dodecyl sulfate, and a plurality of plasmonic nanoparticles in an amount effective to induce thermal damage in a target tissue region with which the composition is topically contacted, wherein the nanoparticles have an optical density of at least about 1 O.D. at a resonance wavelength of about 810 nanometers or 1064 nanometers, wherein the plasmonic particles comprise a silica coating from about 5 to about 35 nanometers, wherein the acceptable carrier comprises water and propylene glycol.

In yet another aspect, provided is a system for laser ablation of hair or treatment of acne comprising a composition and a source of plasmonic energy suitable for application to the human skin.

DETAILED DESCRIPTION

Figure 1:
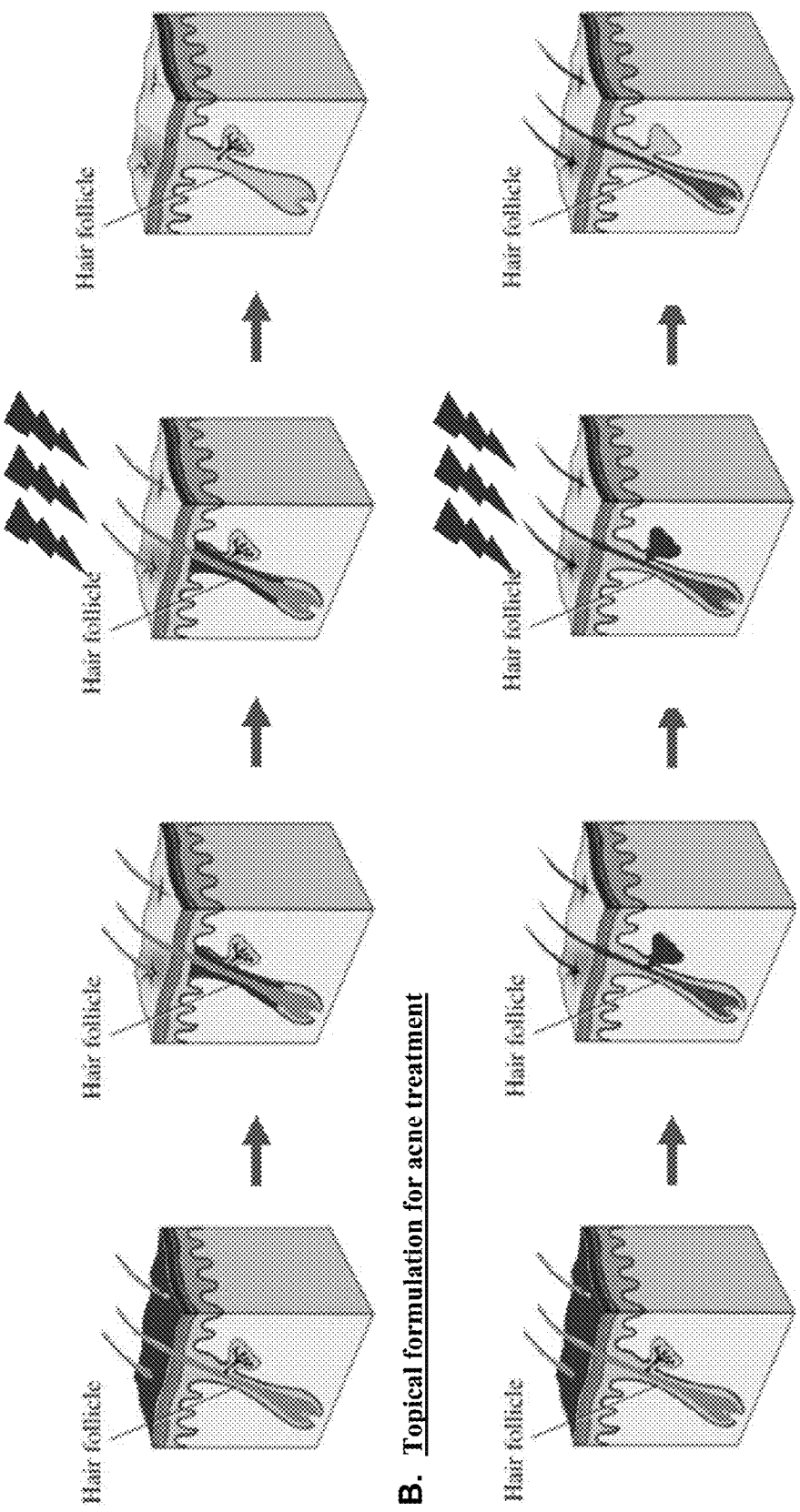
FIG. 1 is illustrative of schematics depicting certain embodiments of the use of formulations for hair removal and acne treatment. Depicted is (A) for hair removal, the plasmonic nanoparticle formulation (black) is 1. applied topically to human skin, 2. delivered deep into the follicle and washed from the skin surface, 3. irradiated with a clinical laser at a wavelength resonant to the peak absorption wavelength of the plasmonic particle, and 4. shed from the follicle along with the damaged hair follicle; and (B) for acne treatment, the plasmonic nanoparticle formulation (black) is 1. applied topically to human skin, 2. delivered specifically into the sebaceous gland and washed from the skin surface, 3. irradiated with a clinical laser at a wavelength resonant to the peak absorption wavelength of the plasmonic particle, and 4. shed from the target site where the accumulated sebum and sebum-producing capabilities of the sebaceous gland are destroyed.

The biology of physiological and pathophysiological tissue growth and remodeling, and alterations in cell morphology is more complex than generally appreciated, involving an interacting network of biological compounds, physical forces, and cell types.

An object of the subject matter described herein is to provide compositions, methods and systems for noninvasive and minimally-invasive treatment of skin and underlying tissues, or other accessible tissue spaces with the use of nanoparticles. The treatment includes, but is not limited to, hair removal, hair growth and regrowth, and skin rejuvenation or resurfacing, acne removal or reduction, wrinkle reduction, pore reduction, ablation of cellulite and other dermal lipid depositions, wart and fungus removal, thinning or removal of scars including hypertrophic scars and keloids, abnormal pigmentation (such as port wine stains), tattoo removal, and skin inconsistencies (e.g. in texture, color, tone, elasticity, hydration). Other therapeutic or preventative methods include but are not limited to treatment of hyperhidrosis, anhidrosis, Frey's Syndrome (gustatory sweating), Homer's Syndrome, and Ross Syndrome, actinic keratosis, keratosis follicularis, dermatitis, vitiligo, pityriasis, psoriasis, lichen planus, eczema, alopecia, psoriasis, malignant or non-malignant skin tumors.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described herein. The materials, methods, and examples are illustrative only and not intended to be limiting. Other features of the disclosure are apparent from the following detailed description and the claims.

"Administer" and "administration" as used herein, include providing or causing the provision of a material to a subject, such as by a topical, subdermal, subcutaneous, intradermal, enteral, parenteral, rectal, nasal, intravenous, intramuscularly, intraperitoneal, or other route.

A "carrier suitable for administration" to a subject is any material that is physiologically compatible with a topical or route of administration to a desired vertebrate subject. Carriers can include solid-based, dry materials for formulation; or the carrier can include liquid or gel-based materials for formulations into liquid or gel forms. The specific type of carrier, as well as the final formulation depends, in part, upon the selected route(s) of administration and the type of product.

A "comparable amount" is an amount that is measurably similar to a given reference or standard.

The "components" of a formulation include any products or compounds associated with or contained within it.

An "effective dose", "effective amount" or "therapeutic amount" is an amount sufficient to elicit the desired pharmacological, cosmetic or therapeutic effects, thus resulting in effective prevention or treatment of a disease or disorder, or providing a benefit in a vertebrate subject.

A "therapeutic effect" or "therapeutically desirable effect" refers to a change in a domain or region being treated such that it exhibits signs of being effected in the manner desired, e.g., cancer treatment causes the destruction of tumor cells or halts the growth of tumor cells, acne treatment causes a decrease in the number and/or severity of blemishes, hair removal treatment leads to evident hair loss, or wrinkle reduction treatment causes wrinkles to disappear.

An "isolated" biological component (such as a nucleic acid molecule, protein, or cell) has been substantially separated or purified away from other biological components in which the component was produced, including any other proteins, lipids, carbohydrates, and other components.

A "nanoparticle", as used herein, refers generally to a particle having at least one of its dimensions from about 0.1 nm to about 9000 nm.

A "subject" or "patient" as used herein is any vertebrate species.

As used herein, a "substantially pure" or "substantially isolated" compound is substantially free of one or more other compounds.

A "target tissue" includes a region of an organism to which a physical or chemical force or change is desired. As described herein, exemplary target tissues for acne treatment include a sebaceous gland, while exemplary target tissues for hair removal include a pilosebaceous unit, a hair infundibulum, a hair follicle, or a non-follicular epidermis. A "region" of a target tissue includes one or more components of the tissue. Exemplary target tissue regions include the stem cell niche, bulge, sebaceous gland, dermal papilla, cortex, cuticle, inner root sheath, outer root sheath, medulla, Huxley layer, Henle layer or *pylori* muscle. A "domain" of a target tissue region includes basement membrane, extracellular matrix, cell-surface proteins, unbound proteins/analytes, glycomatrices, glycoproteins, or lipid bilayer.

A compound that is "substantially free" of some additional contents is largely or wholly without said contents.

A "plasmonic nanoparticle" is a nanometer-sized metallic structure within which localized surface plasmons are excited by light. These surface plasmons are surface electromagnetic waves that propagate in a direction parallel to the metal/dielectric interface (e.g., metal/air or metal/water).

A "light-absorbing nanomaterial" includes a nanomaterial capable of demonstrating a quantum size effect.

As described herein, provided are compositions that contain plasmonic nanoparticles to induce selective thermomodulation in a target tissue.

Plasmonic Nanoparticles.

Such compositions contain from about 2 to about $1 \times 10^{18}$ nanoparticles (e.g., $10^9$ to about $10^{16}$ nanoparticles), such as $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or $10^{18}$ particles. Preferably, the compositions contain about $10^{11}$ to $10^{13}$ particles so that the amount of particles localized to an effective 1 ml treatment volumes is from $10^9$ to $10^{11}$. Generally, the compositions contain nanoparticles in a concentration of from about 1 O.D. to about 10,000 O.D. For embodiments wherein a greater concentration of nanoparticles to a target region is desired, compositions contain particle concentrations with optical densities of, for example, 10 O.D.-5000 O.D. more specifically 100 O.D.-1000 O.D., or optical densities greater than 1,000 O.D. In certain embodiments wherein increased concentration of nanoparticles to a target region is desired, compositions contain particle concentrations with optical densities (O.D.) of 10 O.D.-1000 O.D., or optical densities greater than 1,000 O.D. In some embodiments these correspond to concentrations of about 1-10% w/w or more of nanoparticles. Determination of O.D. units in a composition is determined using devices and analyses known in the art.

Nanoparticles may be homogenous or heterogeneous in size and other characteristics. The size of the nanoparticle is generally about 0.1 nm to about 50,000 nm (e.g., about 0.1 nm to about 5,000 nm) in at least one dimension. Some variation in the size of a population of nanoparticles is to be expected. For example, the variation might be less than 0.01%, 0.1%, 0.5%, 1%, 5%, 10%, 15%, 25%, 50%, 75%, 100%, 200% or greater than 200%. In certain embodiments where optimal plasmonic resonance is desired, a particle size in the range of from about 10 nm to about 100 nm is provided. Alternatively, in embodiments where enhanced penetration of the nanoparticles into a target tissue region such as a hair follicle is desired, a particle size in the range of from about 100 nm to about 1000 nm is provided. Modulation of particle size present in the composition is also a useful means of concentrating the composition in a target domain. Further, as described herein, nanoparticles having a size range of from about 10 nm to about 100 nm can be used as component of a larger molecular structure, generally in the range of from about 100 nm to about 1000 nm. For example, the plasmonic nanoparticle can be surface coated to increase its size, embedded into an acceptable carrier, or it can be cross-linked or aggregated to other particles, or to other materials, that generate a larger particle. In certain embodiments where at least one dimension of at least one nanoparticle within a solution of plasmonic nanoparticles is below 50-100 nm, the nanoparticle surface can be coated with a matrix (e.g. silica) of 10-100 nm thickness or more in order to increase that dimension or particle to 50-100 nm or more. This increased dimension size can increase the delivery of all nanoparticles to a target region (e.g., hair follicle) and limit delivery to non-target region (e.g. dermis). In one embodiment, the invention comprises a composition comprising at least about 1 O.D. (e.g., at least 10 O.D.) of coated plasmonic nanoparticles (e.g., comprising silica or polyethylene glycol (PEG)) having a mean length in at least one dimension greater than about 30 nanometers, wherein the coated nanoparticles are formulated in an acceptable carrier to be effective in induction of selective thermoablation in a target tissue region with which the composition is contacted, wherein the affinity of the coated nanoparticles for the target tissue region is substantially greater than the affinity of the coated nanoparticles for a non-target tissue region.

Important considerations when generating nanoparticles include: 1) the zeta potential (positive, negative, or neutral) and charge density of the particles and resulting compositions; 2) the hydrophilicity/hydrophobicity of the particles and resulting compositions; 3) the presence of an adsorption layer (e.g., a particle slippage plane); and 4) target cell adhesion properties. Nanoparticle surfaces can be functionalized with thiolated moieties having negative, positive, or neutral charges (e.g. carboxylic acid, amine, hydroxyls) at various ratios. Moreover, anion-mediated surface coating (e.g. acrylate, citrate, and others), surfactant coating (e.g., sodium dodecyl sulfate, sodium laureth 2-sulfate, ammonium lauryl sulfate, sodium octech-1/deceth-1 sulfate, lecithin and other surfactants including cetyl trimethylammonium bromide (CTAB), lipids, peptides), or protein/peptide coatings (e.g. albumin, ovalbumin, egg protein, milk protein, other food, plant, animal, bacteria, yeast, or recombinantly-derived protein) can be employed. Block-copolymers are also useful. Further, one will appreciate the utility of any other compound or material that adheres to the surface of light-absorbing particles to promote or deter specific molecular interactions and improve particle entry into pores or follicles. In some embodiments, the particle surface is unmodified. Modulation of hydrophilicity versus hydrophobicity is performed by modifying nanoparticle surfaces with chemistries known in the art, including silanes, isothiocyanates, short polymers (e.g., PEG), or functionalized hydrocarbons. Polymer chains (e.g., biopolymers such as proteins, polysaccharides, lipids, and hybrids thereof; synthetic polymers such as polyethyleneglycol, PLGA, and others; and biopolymer-synthetic hybrids) of different lengths and packing density are useful to vary the adsorption layer/slippage plane of particles.

Optical Absorption.

Preferred nanoparticles have optical absorption qualities of about 10 nm to about 10,000 nm, e.g., 100-500 nm, 500-750 nm, 600-900 nm, 700-1,000 nm, 800-1,200 nm, or 500-2,000 nm. In specific embodiments, the nanoparticles have optical absorption useful to excitation by standard laser devices or other light sources. For example, nanoparticles absorb at wavelengths of about 755 nm (alexandrite lasers), in the range of about 800-810 nm (diode lasers), or about 1064 nm (Nd: YAG lasers). Similarly, the nanoparticles absorb intense pulsed light (IPL), e.g., at a range of about 500 nm to about 1200 nm.

Assembly.

The nanoparticles provided herein can generally contain a collection of unassembled nanoparticles. By "unassembled" nanoparticles it is meant that nanoparticles in such a collection are not bound to each other through a physical force or chemical bond either directly (particle-particle) or indirectly through some intermediary (e.g. particle-cell-particle, particle-protein-particle, particle-analyte-particle). In other embodiments, the nanoparticle compositions are assembled into ordered arrays. In particular, such ordered arrays can include any three dimensional array. In some embodiments, only a portion of the nanoparticles are assembled, e.g., 5, 10, 15, 20, 25, 30, 35, 40, 45, 50, 55, 60, 65, 70, 75, 80, 86, 90, 95, 99% or greater than 99% of the nanoparticles are assembled in an ordered array. The nanoparticles are assembled by a van der Walls attraction, a London force, a hydrogen bond, a dipole-dipole interaction, or a covalent bond, or a combination thereof.

"Ordered array" "Ordered arrays" can take the form of a macrostructure from individual parts that may be patterned or unpatterned in the form of spheres, colloids, beads, ovals, squares, rectangles, fibers, wires, rods, shells, thin films, or planar surface. In contrast, a "disordered array" lacks substantial macrostructure.

Geometrically Tuned Nanostructures.

The nanoparticles provided herein are formable in all shapes currently known or to be created that absorb light and generate a plasmon resonance at a peak-wavelength or composition of wavelengths from 200 nm to 10,000 nm. In non-limiting examples, the nanoparticles are shaped as spheres, ovals, cylinders, squares, rectangles, rods, stars, tubes, pyramids, stars, prisms, triangles, branches, plates or comprised of a planar surface. In non-limiting examples, the plasmonic particles comprise nanoplates, solid nanoshells, hollow nanoshells nanorods, nanorice, nanospheres, nanofibers, nanowires, nanopyramids, nanoprisms, nanoplates or a combination thereof. Plasmonic particles present in the composition comprise a substantial amount of geometrically-tuned nanostructures defined as 5, 10, 15, 25, 50, 75, 80, 85, 90, 95, 98, 99, 99.9 or greater than 99.9% of particles.

Composition.

The nanoparticle is a metal (e.g., gold, silver), metallic composite (e.g., silver and silica, gold and silica), metal oxide (e.g. iron oxide, titanium oxide), metallic salt (e.g., potassium oxalate, strontium chloride), intermetallic (e.g., titanium aluminide, alnico), electric conductor (e.g., copper, aluminum), electric superconductor (e.g., yttrium barium copper oxide, bismuth strontium calcium copper oxide), electric semiconductor (e.g., silicon, germanium), dielectric (e.g., silica, plastic), or quantum dot (e.g., zinc sulfide, cadmium selenium). In non-limiting examples, the materials are gold, silver, nickel, platinum, titanium, palladium, silicon, galadium. Alternatively, the nanoparticle contains a composite including a metal and a dielectric, a metal and a semiconductor, or a metal, semiconductor and dielectric.

Coating.

Preferentially, the composition contains coated nanoparticles.

| Type of Material | Properties | Exemplary Materials |
|---|---|---|
| biorecognitive material | Moiety with affinity or avidity for a substrate or analyte | Antibody, peptide, phage, DNA, RNA |
| bioactive material | Moiety (e.g., protein, analyte) that interrogates or modulates the activity of biologic entity or cell | Growth factor (e.g. VEGF), cytokine, cell surface receptors, receptor ligands, G-protein, kinase/phosphatase |
| biological material | Material that is sourced from living matter | albumin, ovalbumin, egg protein, milk protein, other food, plant, animal, bacteria, yeast, or recombinantly- |

-continued

| Type of Material | Properties | Exemplary Materials |
|---|---|---|
| | | derived protein; peptides; enzymes, lipids, fatty acids, sugars |
| biocide material | Material that is active in killing, destroying, or disturbing biological matter | Synthetic or natural pesticides, synthetic or natural anti-microbials |
| dielectric materials | An insulator that may be polarized by an electric field | Silicon, doped semiconductors |
| chemorecognitive material | Material that is able to interact with a moiety for binding, biological or chemical reactions | Receptor, receptor ligand, chemical molecule |
| chemical active material | Material that causes the transformation of a substance | Aldehyde, halogens, metals |
| Polymer/ dendrimer | Long chain molecule (linear or branched, block or co-block) | PLGA, PEG, PEO, polystyrene, carboxylate styrene, rubbers, nylons, silicones, polysaccharides |
| environmentally sensitive polymer | Surface molecule that changes by its environment (e.g. acid) | Ph sensitive bond, light sensitive bond, heat sensitive bond, enzyme sensitive bond, hydrolytic bond |
| Hydrogel | Polymer with high hydrophilicity and water "ordering" capacity | Synthetic 2-hydroxyethyl methacrylate (HEMA)-based, polyethylene glycol (PEG)-based, PLGA, PEG-diacrylate; Natural ionic gels, alginate, gelatin, hyaluronic acids, fibrin |
| Metal | Thin metal coating to achieve improved resonance and/or functionalization capacity | Gold, silver, nickel, platinum, titanium, and palladium. |
| Semiconductors | Semiconductor layer or core that enhance Plasmon resonance | Silicon and galadium. |
| polymer containing a fluorescent marker | Fluorophore cross linked to a polymer coat or directly to the surface of the particle | Fluorescein, rhodamine, Cy5, Cy5.5, Cy7, Alexa dyes, Bodipy dyes |
| Matrix | Matrix coating that increases solubility of nanoparticles and/or reduces "stickiness" to biological structures | Silica, polyvinyl pyrrolidone, polysulfone, polyacrylamide, polyethylene glycol, polystyrene cellulose, carbopol. |

Biological Molecules.

The composition may contain a peptide, a nucleic acid, a protein, or an antibody. For example a protein, antibody, peptide, or nucleic acid that binds a protein of a follicular stem cell (e.g., keratin 15), a protein, glycomatrix, or lipid on the surface of a cell or stem cell, a protein, peptide, glycomatrix of the extracellular matrix or basement membrane.

Charged Moieties.

The coated nanoparticles may contain charged moieties whereby those charges mediate enhanced or diminished binding to components within or outside the hair follicle via electrostatic or chemical interactions.

| Class of Moiety | Properties | Exemplary Moieties |
|---|---|---|
| Polar moieties | Neutral charge but increases hydrophilicity in water | Hydroxyl groups, isothiocyanates |
| Non-polar moieties | Increases hydrophobicity and or improves solubility | Hydrocarbons, myristoylated compounds, silanes, isothiocyanates |
| Charged moieties | Functional surface modifications that change the zeta potential, isoelectric point, or pKa, and impact adsorption/binding to complementary charge compounds | Amines, carboxylic acids, hydroxyls |
| Ionic moieties | Surface groups that have a single ion | Ammonium salts, chloride salts |
| Basic moieties | Groups that donate a hydrogen ions | Amides, hydroxides, metal oxides, fluoride |
| Acidic moieties | Moieties that accept hydrogen ions | Carboxylic acids, sulfonic acids, mineral acids |
| Oxidative moieties | Moieties that oxidize | Manganese ions, reactive oxygen species |
| Hydrophobic moieties | Moieties that improve solubility in non-aqueous solution and/or improve adsorption on the skin within a hair follicle | Hydrocarbons, myristoylated compounds, silanes |
| Hydrophilic moieties | Moieties that are water-loving and prevent adsorption | PEG, PEO, PLGA |
| Agnostic moieties | Moieties that bind a target cell, structure, or protein of interest | Antibodies, peptides, proteins |
| Antagonistic moieties | Moieties that block the binding to a target of interest | Antibodies, peptides, proteins |
| Reactive moieties | Moieties that react with biological or non-biological components with a resulting change in structure on the target | Aldehydes |

Description of Target Tissues.

Topical and Dermatological Applications.

Target tissues for topical and dermatological applications include the surface of the skin, the epidermis and the dermis. Diseases or conditions suitable for treatment with topical and dermatological applications include acne, warts, fungal infections, psoriasis, scar removal, hair removal, hair growth, reduction of hypertrophic scars or keloids, skin inconsistencies (e.g. texture, color, tone, elasticity, hydration), and malignant or non-malignant skin tumors.

As used herein, the term "acne" includes acne *vulgaris* as well as other forms of acne and related cutaneous conditions, including acne *aestivalis*, acne conglobata, acne cosmetic, acne fulminans, acne keloidalisnuchae, acne mechanica, acne miliarisnecrotica, acne necrotica, chloracne, drug-induced acne, excoriated acne, halogen acne, lupus miliaris disseminates faciei, pomade acne, tar acne, and tropical acne.

Subdermal Applications.

Target tissues for subdermal applications include the adipose tissue and connective tissue below the integumentary system. Diseases or conditions suitable for treatment with subdermatological applications include wrinkles and tattoos. Other applications include skin rejuvenation and/or resurfacing, the removal or reduction of stretch marks and fat ablation.

Often, a specific region of the target tissue is a hair follicle, a sebaceous gland, a merocrine sweat gland, an apocrine sweat gland, or an arrector pili muscle, within which a specific domain is targeted. For example, the bulge region of the hair follicle is targeted. Because in one embodiment the nanoparticles are useful to thermally ablate hair follicle stem cells for hair removal, regions containing hair follicle stem cells are of particular interest for targeting. Thus, the target tissue region may include a stem cell niche, bulge, sebaceous gland, dermal papilla, cortex, cuticle, inner root sheath, outer root sheath, medulla, Huxley layer, Henle layer or *pylori* muscle. Each of these regions may contain cells, stem cells, basement membrane, extracellular matrix, growth factors, analytes, or other biologic components that mediate hair follicle rejuvenation. Disruption or destruction of these components would have a therapeutic effect, e.g. slow or stop the processes that mediate hair regrowth, prevent the secretion of sebum from the sebaceous gland, damage or deter tumor cells, reduce the appearance of wrinkles. Structures can also be targeted that are in close proximity to a desired target for ablation, especially when capable of conducting heat effectively.

Localization Domains.

Provided are compositions containing nanoparticles that preferentially localize to a domain of a target tissue region of a mammalian subject to whom the composition is administered.

Targeting Moieties.

The nanoparticles can be engineered to selectively bind to a domain of the target tissue. For example, the nanoparticles are operably linked to the domain via a biologic moiety, in order to effectively target the nanoparticles to the target tissue domain. Preferably, the moiety contains a component of a stem cell, a progenitor cell, an extracellular matrix component, a basement membrane component, a hair shaft component, a follicular epithelial component, or a non-follicular epidermal component. Biological moieties include proteins such as cell surface receptors, glycoproteins or extracellular matrix proteins, as well as carbohydrates, analytes, or nucleic acids (DNA, RNA) as well as membrane components (lipid bilayer components, microsomes).

Delocalization Domains.

Nanoparticles present in the composition preferentially delocalize away from a domain of a target tissue region. Delocalization domains include specific regions of a tissue into which nanoparticles do not substantially aggregate, or alternatively, are removed from the domain more effectively. In preferred embodiments, the delocalization domain is a non-follicular epidermis, dermis, a component of a hair follicle (e.g., a hair stem cell, a stem cell niche, a bulge, a sebaceous gland, a dermal papilla, a cortex, a cuticle, an inner root sheath, an outer root sheath, a medulla, a Huxley layer, a Henle layer, a *pylori* muscle), a hair follicle infundibulum, a sebaceous gland, a component of a sebaceous gland, a sebocyte, a component of a sebocyte, or sebum Energy Sources.

Provided herein are nonlinear excitation surface plasmon resonance sources, which include various light sources or optical sources. Exemplary light sources include a laser (ion laser, semiconductor laser, Q-switched laser, free-running laser, or fiber laser), light emitting diode, lamp, the sun, a fluorescent light source or an electroluminescent light source. Typically, the energy source is capable of emitting radiation at a wavelength from about 100, 200, 300, 400, 500, 1000, 2000, 5000 nm to about 10,000 nm or more. The nonlinear excitation surface plasmon resonance source is capable of emitting electromagnetic radiation, ultrasound, thermal energy, electrical energy, magnetic energy, or electrostatic energy. For example, the energy is radiation at an intensity from about 0.00005 mW/cm$^2$ to about 1000 TW/cm$^2$. The optimum intensity is chosen to induce high thermal gradients from plasmonic nanoparticles in regions from about 10 microns to hundreds of microns in the surrounding tissue, but has minimal residual effect on heating tissue in which particles do not reside within a radius of about 100 microns or more from the nanoparticle. In certain embodiments, a differential heat gradient between the target tissue region and other tissue regions (e.g., the skin) is greater than 2-fold, 3-fold, 5-fold, 10-fold, 15-fold, 20-fold, 50-fold, 100-fold, or greater than 100 fold.

The energy can be tuned by monitoring thermal heat gradients on the surface of the skin with a thermal/infrared camera. As demonstrated herein, the methods and systems of the present disclosure provide superior efficacy when a surface plasmon is generated on the nanoparticles by the action of the radiation. Typically, the plasmon is generated in a one-photon mode or, alternatively, a two-photon mode, a multi-photon mode, a step-wise mode, or an up-conversion mode.

Delivery of Radiation.

Physical means of delivery of the energy from the nonlinear excitation surface plasmon resonance source to the target tissue region include a fiber, waveguide, a contact tip or a combination thereof.

Optical sources include a CW optical source or a pulsed optical source, which may be a single wavelength polarized (or, alternatively, unpolarized) optical source capable of emitting radiation at a frequency from about 200 nm to about 10,000 nm. Alternatively, the optical source is a multiple wavelength polarized (or, alternatively, unpolarized) optical source capable of emitting radiation at a wavelength from about 200 nm to about 10,000 nm. The pulsed optical source is generally capable of emitting pulsed radiation at a frequency from about 1 Hz to about 1 THz. The pulsed optical source is capable of a pulse less than a millisecond, microsecond, nanosecond, picoseconds, or femtosecond in duration. For example, a source emitting radiation at a wavelength of 755 nm is operated in pulse mode such that the emitted radiation is pulsed at a duration of 0.25-300 milliseconds (ms) per pulse, with a pulse frequency of 1-10 Hz. In another example, radiation emitted at a wavelength of 810 nm is pulsed at 5-100 ms with a frequency of 1-10 Hz. In a further example, a source emitting radiation at a wavelength of 1064 nm is pulsed at 0.25-300 ms at a frequency of 1-10 Hz. In yet another example, a source emitting intense pulsed light at a wavelength of 530-1200 nm is pulsed at 0.5-300 ms at a frequency of 1-10 Hz. The optical source may be coupled to a skin surface cooling device to reduce heating of particles or structures on the skin surface and focus heating to components within follicles or tissue structures at deeper layers.

Nanoparticle-Containing Compositions.

In order to provide optimal dermal penetration into the target tissue, the plasmonic nanoparticles in certain embodiments are formulated in various compositions. Preferentially, the nanoparticles are formulated in compositions containing 1-10% v/v surfactants (e.g. sodium dodecyl sulfate, sodium laureth 2-sulfate, ammonium lauryl sulfate, sodium octech-1/deceth-1 sulfate). Surfactants disrupt and emulsify sebum or other hydrophobic fluids to enable improved targeting of hydrophilic nanoparticles to the hair follicle, infundibulum, sebaceous gland, or other regions of the skin. Surfactants also lower the free energy necessary to deliver hydrophilic nanoparticles into small hydrophobic crevices such as the space between the hair shaft and follicle or into the sebaceous gland. Nanoparticle-containing compositions may also include emulsions at various concentrations (1-20% w/v) in aqueous solutions, silicone/oil solvents, polypropylene gel, propylene glycol or creams (e.g. comprising alcohols, oils, paraffins, colloidal silicas). In other embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Alternatively, a matrix component such as silica, polystyrene or polyethylene glycol is provided in the formulation. Other formulations include components of surfactants, a lipid bilayer, a liposome, or a microsome. A nanoparticle may comprise a larger micron-sized particle.

Effective Doses.

As described herein, an effective dose of the nanoparticle-containing compositions includes an amount of particles required, in some aspects, to generate an effective heat gradient in a target tissue region, such that a portion of the target tissue region is acted upon by thermal energy from excited nanoparticles. A "minimal effective dose" is the smallest number or lowest concentration of nanoparticles in a composition that are effective to achieve the desired biological, physical and/or therapeutic effect(s). Preferentially, the plasmonic nanoparticles have an optical density of 10 O.D.-1,000 O.D. at one or a plurality of peak resonance wavelengths.

Cosmetically Acceptable Carriers.

Provided are cosmetic or pharmaceutical compositions with a plurality of plasmonic nanoparticles and a cosmetically or pharmaceutically acceptable carrier. Generally, the carrier and composition must be suitable for topical administration to the skin of a mammalian subject, such that the plasmonic nanoparticles are present in an effective amount for selective thermomodulation of a component of the skin. Preferentially, the nanoparticles are formulated with a carrier containing 1-10% v/v surfactants (e.g. sodium dodecyl sulfate, sodium laureth 2-sulfate, ammonium lauryl sulfate, sodium octech-1/deceth-1 sulfate) to enable disruption of the epidermal skin barrier, emulsify sebum, improve mixing of hydrophilic nanoparticles with hydrophobic solutions, and reduce entropic barriers to delivering hydrophilic particles to hydrophobic regions of the skin (e.g. between the hair shaft and surrounding sheath or follicle). In some embodiments, the carrier contains a polar or non-polar solvent. For example, suitable solvents include alcohols (e.g., n-Butanol, isopropanol, n-Propanol, Ethanol, Methanol), hydrocarbons (e.g., pentane, cyclopentane, hexane, cyclohexane, benzene, toluene, 1,4-Dioxane), chloroform, Diethyl-ether, water, water with propylene glycol, acids (e.g., acetic acid, formic acid), bases, acetone, isooctanes, dimethyl sulfoxide (DMSO), dimethylformamide (DMF), acetonitrile (MeCN), tetrahydrofuran (THF), dichloromethane (DCM), ethylacetate, tetramethylammonium hydroxide, isopropanol, and others. In other embodiments, a stabilizing agent such as antioxidants, preventing unwanted oxidation of materials, sequestrants, forming chelate complexes and inactivating traces of metal ions that would otherwise act as catalysts, emulsifiers, ionic or non-ionic surfactants, cholesterol or phospholipids, for stabilization of emulsions (e.g. egg yolk lecithin, Sodium stearoyllactylate, sodium bis(2-ethylhexyl-sulfosuccinate (AOT)), ultraviolet stabilizers, protecting materials, especially plastics, from harmful effects of ultraviolet radiation is provided. In further embodiments, a composition with a cosmetically acceptable carrier is generated such that the nanoparticles are substantially in a suspension.

Other components are also optionally included, including an emulsion, polymer, hydrogel, matrix, lipid bilayer, liposome, or microsome. Additionally, inclusion of a detectable colorant (e.g., a pigment), a fragrance, a moisturizer, and/or a skin protectant is optional. In some examples, the formulation has a viscosity of above, below or within 0.1-10,000 (e.g., $5e^{-4} \times 10^3$, 1,000), as measured in millipascal-seconds (mPa·s).

Nanoparticle quantities per milliliter in a composition are subject to modification for specific binding and can range from $10^9$ to $10^{18}$ particles but generally about $10^{11}$ to $10^{13}$ nanoparticles per milliliter. Nanoparticle quantities per milliliter in a formulation are subject to modification for specific binding but generally up to about $10^{23}$ nanoparticles per milliliter. In certain embodiments wherein increased concentration of nanoparticles to a target region is desired, compositions contain particle concentrations with optical densities of 10 O.D.-1000 O.D., or optical densities greater than 1,000 O.D. In some embodiments these correspond to concentrations of about 0.1-10% w/w or more of nanoparticles.

Prior to application of nanoparticle formulations, skin and hair follicles can be pre-treated to increase the delivery of nanoparticles to a target region. In some embodiments, hair shafts are cut or removed via shaving, waxing, cyanoacrylate surface peels, calcium thioglycolate treatment, or other techniques to remove the hair shaft and/or hair follicle plugs and create a void wherein nanoparticles can accumulate. Orifices of active or inactive follicles can be blocked by plugs formed of corneocytes and/or other material (e.g. cell debris, soot, hydrocarbons, cosmetics). In some embodiments pre-treatment with surface exfoliation including mechanical exfoliation (e.g., salt glow or microdermabrasion) and chemical exfoliation (e.g., enzymes, alphahydroxy acids, or betahydroxy acids) removes plugs from the orifice of follicles to increase the targeting of nanoparticle formulations to target regions within the hair follicle.

In some embodiments, the nanoparticle formulations are formulated for application by a sponge applicator, cloth applicator, direct contact via a hand or gloved hand, spray, aerosol, vacuum suction, high pressure air flow, or high pressure liquid flow, roller, brush, planar surface, semi-planar surface, wax, ultrasound and other sonic forces, mechanical vibrations, physical manipulation, hair shaft manipulation (including pulling, massaging), physical force, electrophoresis, iontophoresis, thermal manipulation, and other treatments. In some embodiments, nanoparticle formulation treatments are performed alone, in combination, sequentially or repeated 1-24 times. In other embodiments, the plasmonic nanoparticles are capable of selectively localizing to a first component of the skin, where physical massage or pressure, ultrasound, or heat increase the selective localization of the nanoparticles to this first component. Additionally, the nanoparticles are selectively removable from components of the skin other than the first component, such removal accomplished with acetone, alcohol, water, air, peeling of the skin, chemical peeling, waxing, or reduction of the plasmonic compound. Further, in some embodiments the nanoparticles have a coat layer to increase solubility of the nanoparticles in the carrier and/or reduce "stickiness" and accumulation in non-target areas. The subject matter described herein also provides embodiments in which at least a portion of an exterior surface of the nanoparticle is modified, such as to include a layer of a polymer, polar monomer, non-polar monomer, biologic compound, a metal (e.g., metallic thin film, metallic composite, metal oxide, or metallic salt), a dielectric, or a semiconductor. Alternatively, the exterior surface modification is polar, non-polar, charged, ionic, basic, acidic, reactive, hydrophobic, hydrophilic, agonistic, or antagonistic. In certain embodiments where at least one dimension of at least one nanoparticle within a solution of plasmonic nanoparticles is below 50-100 nm, the nanoparticle surface can be coated with a matrix (e.g. silica) of 10-100 nm thickness or more in order to increase that dimension or particle to 50-100 nm or more. This increased dimension size can increase the delivery of all nanoparticles to a target region (e.g., hair follicle) and limit delivery to non-target region (e.g. dermis).

Penetration Means.

Preferably, the compositions of the instant disclosure are topically administered. Provided herein area means to redistribute plasmonic particles from the skin surface to a component of dermal tissue including a hair follicle, a component of a hair follicle, a follicle infundibulum, a sebaceous gland, or a component of a sebaceous gland using high frequency ultrasound, low frequency ultrasound, massage, iontophoresis, high pressure air flow, high pressure liquid flow, vacuum, pre-treatment with Fractionated Photothermolysis laser or derm-abrasion, or a combination thereof. The nanoparticles described herein are formulated to penetrate much deeper—up to several centimeters, or into the panniculus adiposus (hypodermis) layer of subcutaneous tissue. For example, the compositions can be administered by use of a sponge applicator, cloth applicator, spray, aerosol, vacuum suction, high pressure air flow, high pressure liquid flow direct contact by hand ultrasound and other sonic forces, mechanical vibrations, physical manipulation, hair shaft manipulation (including pulling, massaging), physical force, thermal manipulation, or other treatments. Nanoparticle formulation treatments are performed alone, in combination, sequentially or repeated 1-24 times.

Cosmetic and Therapeutic Uses of Plasmonic Nanoparticles.

In general terms, Applicant(s) have created systems and methods for the cosmetic and therapeutic treatment of dermatological conditions, diseases and disorders using nanoparticle-based treatments methods.

Acne Treatment.

Acne is caused by a combination of diet, hormonal imbalance, bacterial infection (*Propionibacterium acnes*), genetic predisposition, and other factors. The nanoparticle-based methods and systems described herein for acne treatment are able to focally target causative regions of the dermis, the sebaceous gland and the hair follicle, and thus have advantages compared to the existing techniques known in the art, including chemical treatment (peroxides, hormones, antibiotics, retinoids, and anti-inflammatory compounds), dermabrasion, phototherapy (lasers, blue and red light treatment, or photodynamic treatment), or surgical procedures.

In particular, laser-based techniques are becoming an increasingly popular acne treatment, but a substantial limitation is the lack of selective absorptive properties among natural pigments (e.g. fat, sebum) for specific wavelengths of light such that selective heating of one cell, structure, or component of tissue, particularly in the sebaceous glands, infundibulum, and regions of the hair follicle, is not achieved without heating of adjacent off-target tissue. The nanoparticles described herein provide significantly higher photothermal conversion than natural pigments enabling laser energy to be focused to specific cells, structures, or components of tissue within the sebaceous gland, infundibulum, or regions of the hair follicle for selective photothermal damage.

Using the materials and techniques described herein may provide acne treatments of greater duration than existing methodologies. In certain embodiments, tuned selective ablation of the sebaceous gland or infundibulum is achieved as described herein. In particular, plasmonic nanoparticles are specifically localized to regions of hair follicles in or proximate to the sebaceous gland or infundibulum.

Plasmonic nanoparticles exhibit strong absorption at wavelengths emitted by standard laser hair removal devices (e.g., 755 nm, 810 nm, 1064 nm) relative to surrounding epidermal tissue. Thus, irradiation of targeted plasmonic nanoparticles with laser light induces heat radiation from the particles to the adjacent sebum, sebaceous gland, infundibulum, and other acne causing agents.

Hair Removal.

The nanoparticle-based methods and systems described herein for skin treatment have advantages compared to the existing techniques known in the art, including laser-based techniques, chemical techniques, electrolysis, electromagnetic wave techniques, and mechanical techniques (e.g., waxing, tweezers). Such techniques fail to adequately provide permanent hair removal across a breadth of subjects. In particular, subjects having light to medium-pigmented hair are not adequately served by these techniques, which suffer from side-effects including pain and the lack of beneficial cosmetic affects including hair removal. Laser-based techniques are popular in a variety of applications, but a substantial limitation is the lack of selective absorptive properties among natural pigments (e.g. melanin) for specific wavelengths of light such that selective heating of one cell, structure, or component of tissue is achieved without heating of adjacent off-target tissues. The nanoparticles described herein provide significantly higher photothermal conversion than natural pigments enabling laser energy to be focused to specific cells, structures, or components of tissue for selective photothermal damage. The methods described herein are useful for hair removal of all types and pigmentations. For example, melanin, the predominant hair pigment, is an aggregation of chemical moieties including eumelanin and phaeomelanin. Eumelanin colors hair grey, black, yellow, and brown. A small amount of black eumelanin in the absence of other pigments causes grey hair. Types of eumelanin include black eumelanin and brown eumelanin, with black melanin being darker than brown. Generally, black eumelanin predominates in non-European subjects and aged Europeans, while brown eumelanin is in greater abundance in young European subjects. Phaeomelanin predominates in red hair. In another example, vellus hair ("peach fuzz") is a type of short, fine, light-colored, and usually barely noticeable hair that develops on much or most of a subject's body (excluding lips, palms of hand, sole of foot, navel and scar tissue). While the density of vellus hair is generally lower than that of other hair types, there is variation from person to person in the density, thickness, and pigmentation. Vellus hair is usually less than 2 mm long and the follicle containing the vellus hair is generally not connected to a sebaceous gland. Conditions associated with an overabundance of vellus hair include Cushing's syndrome and anorexia nervosa, such overgrowth being treatable using the methods and compositions described herein. Further, provided are methods of targeting hair growth at a given stage. Hair grows in cycles of various stages or phases. Growth phase is termed "anagen", while "catagen" includes the involuting or regressing phase, and "telogen" encompasses the resting or quiescent phase. Each phase has several morphologically and histologically distinguishable subphases. Generally, up to 90% of the hair follicles on a subject are in anagen phase (10-14% are in telogen and 1-2% in catagen). The cycle's length is governed by cytokines and hormones, and varies on different parts of the body. For eyebrows, the cycle is completed in around 4 months, while it takes the scalp 3-4 years to finish. The methods and compositions described herein are sufficient to treat hair of all growth stages or phases.

More permanent reduction or removal of all hair types is provided herein, relative to hair removal treatments known in the art. In certain embodiments, tuned selective ablation of the hair shaft and destruction of stem cells in the bulge region is provided, as described herein. In particular, plasmonic nanoparticles are specifically localized to regions of hair follicles in or proximate to the bulge region, a stem cell-rich domain of the hair follicle. Moreover, the plasmonic nanoparticles are localized in close approximation of ~50-75% of the hair shaft structure.

Plasmonic nanoparticles exhibit strong absorption at wavelengths emitted by standard laser hair removal devices (e.g., 755 nm, 810 nm, 1064 nm) relative to surrounding epidermal tissue. Thus, irradiation of targeted plasmonic nanoparticles with laser light induces heat radiation from the particles to the adjacent stem cells (or in some cases, the architecture of the hair shaft itself), resulting in cell death and a disruption of the normal regenerative pathway.

Non-Malignant and Malignant Skin Tumors.

Laser therapies for the prevention and treatment of non-malignant, malignant, melanoma and non-melanoma skin cancers have been focused largely on photodynamic therapy approaches, whereby photosensitive porphyrins are applied to skin and used to localize laser light, produce reactive oxygen species and destroy cancer cells via toxic radicals. For example, 5-ALA combined with laser treatment has been FDA-approved for the treatment of non-melanoma skin cancer actinic keratoses, and it is used off-label for the treatment of widely disseminated, surgically untreatable, or recurrent basal cell carcinomas (BCC). However, this procedure causes patients to experiences photosensitivity, burning, peeling, scarring, hypo- and hyper-pigmentation and other side effects due to non-specific transdermal uptake of porphyrin molecules. The nanoparticles described herein provide significantly higher photothermal conversion than natural pigments and dyes, enabling laser energy to be focused to specific cells, structures, or components of tissue for selective thermomodulation Using the materials and techniques described herein may provide cancer treatments of greater degree and duration than existing methodologies. In certain embodiments, tuned selective ablation of specific target cells, such as Merkel cells or Langerhans cells, as described herein. In particular, plasmonic nanoparticles are specifically localized to regions of hair follicles where follicular bulge stem cells arise to form nodular basal cell carcinomas and other carcinomas. Plasmonic nanoparticles may also be delivered to other target cells that cause tumors, for example, the interfollicular epithelium, which include the cell of origin for superficial basal cell carcinomas.

Plasmonic nanoparticles exhibit strong absorption at wavelengths emitted by standard laser hair removal devices (e.g., 755 nm, 810 nm, 1064 nm) relative to surrounding epidermal tissue. Thus, irradiation of targeted plasmonic nanoparticles with laser light induces heat radiation from the particles to the adjacent keratinocyte, melanocyte, follicular bulge stem cell, cancer cell, or cancer cell precursor, resulting in cell death or inhibited cell growth for cancer prevention and treatment.

Subdermal Applications.

Target tissues for subdermal applications include the adipose tissue and connective tissue below the integumentary system. Diseases or conditions suitable for treatment with subdermatological applications include wrinkles and tattoos. Other applications include skin rejuvenation and/or resurfacing, the removal or reduction of stretch marks and fat ablation.

Vascular Applications.

Target tissues for vascular applications include arteries, arterioles, capillaries, vascular endothelial cells, vascular smooth muscle cells, veins, and venules. Diseases or conditions suitable for treatment with vascular applications include spider veins, leaky valves, and vascular stenosis. In particular, vein abnormalities account for a substantial proportion of cosmetic diseases or conditions affecting the vasculature. Individuals with vein abnormalities such as spider veins or faulty venous valves suffer from pain, itchiness, or undesirable aesthetics.

Additionally, there are several indication for which ablation of other vessels including arteries, arterioles, or capillaries could provide therapeutic or cosmetic benefit including: 1) ablation of vasculature supplying fat pads and/or fat cells, 2) ablation of vasculature supporting tumors/cancer cells, 3) ablation of vascular birth marks (port-wine stains, hemangiomas, macular stains), and 4) any other indication whereby ablation of vessels mediates the destruction of tissue and apoptosis or necrosis of cells supported by those vessels with therapeutic or cosmetic benefit. Provided herein are methods for using the compositions described herein for the selective destruction of component(s) of veins from plasmonic nanoparticles focally or diffusely distributed in the blood. Plasmonic nanoparticles are combined with a pharmaceutically acceptable carrier as described above and are introduced into the body via intravenous injection. Nanoparticles diffuse into the blood and, in some embodiments, localize to specific vascular tissues. Subsequently, the nanoparticles are activated with laser or light-based systems as known in the art for treating skin conditions such as hair removal or spider vein ablation. Alternatively, image or non-image guided fiber optic waveguide-based laser or light systems may be used to ablate vessel or blood components in larger veins. In one embodiment, a device with dual functions for both injecting nanoparticles and administering light through on optical waveguide may be used. Activated nanoparticles heat blood and adjacent tissue (vessels, vessel walls, endothelial cells, components on or in endothelial cells, components comprising endothelial basement membrane, supporting mesenchymal tissues, cells, or cell components around the vessel, blood cells, blood cell components, other blood components) to ablative temperatures (38-50 degrees C. or higher).

Provided herein is a composition comprising a pharmaceutically acceptable carrier and a plurality of plasmonic nanoparticles in an amount effective to induce thermomodulation of a vascular or intravascular target tissue region with which the composition is intravenously contacted. Furthermore, the composition of plasmonic nanoparticle may comprise a microvascular targeting means selected from the group consisting of anti-microvascular endothelial cell antibodies and ligands for microvascular endothelial cell surface receptors. Also provided is a method for performing thermoablation of a target vascular tissue in a mammalian subject, comprising the steps of contacting a region of the target vascular tissue with a composition comprising a plurality of plasmonic nanoparticles and a pharmaceutically acceptable carrier under conditions such that an effective amount of the plasmonic nanoparticles localize to a domain of the target vascular region; and exposing the target tissue region to energy delivered from a nonlinear excitation surface plasmon resonance source in an amount effective to induce thermoablation of the domain of the target vascular region.

Oral and Nasal Applications.

Target tissues for oral applications include the mouth, nose, pharynx, larynx, and trachea. Diseases or conditions suitable for treatment with vascular applications include oral cancer, polyps, throat cancer, nasal cancer, and Mounier-Kuhn syndrome.

Endoscopic Applications. Target tissues for endoscopic applications include the stomach, small intestine, large intestine, rectum and anus. Diseases or conditions suitable for treatment with vascular applications include gastrointestinal cancer, ulcerative colitis, Crohn's disease, Irritable Bowel Syndrome, Celiac Disease, Short Bowel Syndrome, or an infectious disease such as giardiasis, tropical sprue, tapeworm infection, ascariasis, enteritis, ulcers, Whipple's disease, and megacolon.

Methods of Thermomodulation.

Provided are methods for performing thermomodulation of a target tissue region. A nanoparticle composition comprising a plurality of plasmonic nanoparticles under conditions such that an effective amount of the plasmonic nanoparticles localize to a domain of the target tissue region; and exposing the target tissue region to energy delivered from a nonlinear excitation surface plasmon resonance source in an amount effective to induce thermomodulation of the domain of the target tissue region.

Removal of Non-Specifically Bound Nanoparticles.

Removing nanoparticles localized on the surface of the skin may be performed by contacting the skin with acetone, alcohol, water, air, a debriding agent, or wax. Alternatively, physical debridement may be performed. Alternatively, one can perform a reduction of the plasmonic compound.

Amount of Energy Provided.

Skin is irradiated at a fluence of 1-60 Joules per $cm^2$ with laser wavelengths of about, e.g., 750 nm, 810 nm, 1064 nm, or other wavelengths, particularly in the range of infrared light. Various repetition rates are used from continuous to pulsed, e.g., at 1-10 Hz, 10-100 Hz, 100-1000 Hz. While some energy is reflected, it is an advantage of the subject matter described herein is that a substantial amount of energy is absorbed by particles, with a lesser amount absorbed by skin. Nanoparticles are delivered to the hair follicle, infundibulum, or sebaceous gland at concentration sufficient to absorb, e.g., 1.1-100× more energy than other components of the skin of similar volume. This is achieved in some embodiments by having a concentration of particles in the hair follicle with absorbance at the laser peak of 1.1-100× relative to other skin components of similar volume.

To enable tunable destruction of target skin structures (e.g., sebaceous glands, infundibulum, hair follicles), light-absorbing nanoparticles are utilized in conjunction with a laser or other excitation source of the appropriate wavelength. The laser light may be applied continuously or in pulses with a single or multiple pulses of light. The intensity of heating and distance over which photothermal damage will occur are controlled by the intensity and duration of light exposure. In some embodiments, pulsed lasers are utilized in order to provide localized thermal destruction. In some such embodiments, pulses of varying durations are provided to localize thermal damage regions to within 0.05, 0.1, 0.5, 1, 2, 5, 10, 20, 30, 50, 75, 100, 200, 300, 500, 1000 microns of the particles. Pulses are at least femtoseconds, picoseconds, microseconds, or milliseconds in duration. In some embodiments, the peak temperature realized in tissue from nanoparticle heating is at least 5, 10, 15, 20, 25, 30, 40, 50, 60, 70, 80, 90, 100, 200, 300, or 500 degrees Celsius. In some embodiments that utilize pulsed heating, high peak temperatures are realized locally within the hair shaft without raising the macroscopic tissue temperature more than 0.1, 0.5, 1, 2, 3, 4, 5, 7, 9, 12, 15, or 20 degrees Celsius. In some embodiments short pulses (100 nanoseconds-1000 microseconds) are used to drive very high transient heat gradients in and around the target skin structure (e.g., sebaceous gland and/or hair follicle) from embedded particles to localize damage in close proximity to particle location. In other embodiments, longer pulse lengths (1-10 ms, or 1-500 ms) are used to drive heat gradients further from the target structure to localize thermal energy to stem cells in the bulge region or other components greater than 100 µm away from the localized particles. Fluences of 1-10 Joules per $cm^2$ or 1-30 Joules per $cm^2$ are generally sufficient to thermally ablate follicles that have high particle concentrations and thus higher absorbance than skin (e.g., 1.1-100 times per volume absorbance of skin). These fluences are often lower than what is currently employed (e.g., Diode: 25-40 J/$cm^2$, Alexandrite: 20 J/cm2, Nd:YAG: 30-60 J/$cm^2$) and lead to less damage to non-follicular regions, and potentially less pain.

Plasmon Resonance Systems.

Provided are plasmon resonance systems containing a surface that includes a plurality of plasmonic nanoparticles, and a nonlinear excitation source. Optionally, the system contains a means to generate thermal heating of the surface. Preferably, the surface is a component of skin that is targeted for cosmetic or therapeutic treatment (e.g., bulge region for hair removal, infundibulum or sebaceous gland for acne prevention). Also provided as a component of the system is a means for delivering plasmonic nanoparticles to the skin surface, such as an applicator, a spray, an aerosol, vacuum suction, high pressure air flow, or high pressure liquid flow. Further provided are means of localizing plasmonic nanoparticles to a component of the skin (e.g., hair follicle, bulge region, sebaceous gland, infundibulum). Useful surface delivery means include a device that generates high frequency ultrasound, low frequency ultrasound, heat, massage, contact pressure, or a combination thereof.

Further provided are systems that contain a removal means for removing nanoparticles on a non-follicular portion of the skin. The removal means includes at least one of acetone, alcohol, water, air, chemical peeling, wax, or a compound that reduces the plasmonic compound.

In addition, the systems of the present disclosure provide nonlinear excitation source that generates a continuous wave optical source or a pulsed optical source. Alternatively, the nonlinear excitation source is capable of generating electromagnetic radiation, ultrasound, thermal energy, electrical energy, magnetic energy, or electrostatic energy. Provided are systems wherein the nonlinear excitation source is capable of irradiating the nanoparticles with an intensity from about 0.00005 mW/$cm^2$ to about 1000 TW/$cm^2$. Further, the nonlinear excitation source is capable of functioning in a one-photon mode, two-photon mode, multi-photon mode, step-wise mode, or up-conversion mode. A fiber, a waveguide, a contact tip, or a combination thereof may be used in the instant systems.

In some embodiments, the system contains a monitoring device such as a temperature sensor or a thermal energy detector. In other embodiments, the systems also contain a controller means for modulating the nonlinear excitation source (e.g., a "feedback loop controller"). In a related embodiment, the system contains a means for detecting a temperature of the surface or a target tissue adjacent to the surface, wherein the controller means modulates the intensity of the nonlinear excitation source and/or the duration of the excitation. In such embodiments, the controller means preferably modulates the intensity of the nonlinear excitation source such that a first component of the hair follicle is selectively thermoablated relative to a second component of the hair follicle. In further embodiments, a cooling device is directly contacted with the skin during irradiation to minimize the heating of nanoparticles or skin at the surface, while nanoparticles that have penetrate more deeply into the follicle, skin, or sebaceous gland heat to temperatures that selectively ablate the adjacent tissues.

Skin is an exemplary target tissue. The skin preferably contains a hair follicle and/or a sebaceous gland, where the nonlinear excitation source generates energy that results in heating the skin in an amount effective to induce thermomodulation of a hair follicle, a infundibulum, a sebaceous gland, or a component thereof, such as by heating sufficient to cause the temperature of the skin to exceed 37° C., such as 38° C., 39° C., 40° C., 41° C., 42° C., 43° C., 44° C., 45° C., 46° C., 47° C., 48° C., 49° C., to about 50° C. or greater.

Methods of Formulation.

Also provided are methods for formulating the nanoparticles of the present disclosure into a form suitable for use as described herein. In particular, the nanoparticle compositions are generated by:
a) forming a first mixture containing a plurality of nanoparticles and a first solvent;
b) exchanging the first solvent for a second solvent to form a second mixture; and
c) combining the second mixture and a cosmetically or pharmaceutically acceptable carrier; thereby forming a nanoparticle composition.

The exchanging step is optionally performed using liquid chromatography, a solvent exchange system, a centrifuge, precipitation, or dialysis. Preferably, the nanoparticles are surface modified through a controlled reduction step or an oxidation step. Such surface modification may involve a coating step, such as the adsorbance of a monomer, polymer, or biological entity to a surface of the nanoparticle. Typically, the coating step involves contacting the nanoparticles with an oxidative environment. Further, the coating step may include monomer polymerization to create polymer coat.

The methods described herein may also include the steps of dissolving the nanoparticles in a non-polar solvent and subsequently mixing the dissolved nanoparticles with a polar solvent so as to encapsulate the nanoparticles in an emulsion. Further, the addition of surfactants (e.g. sodium dodecyl sulfate, sodium laureth 2-sulfate, ammonium lauryl sulfate, sodium octech-1/deceth-1 sulfate) at concentrations of 0.1-10% may be used to disrupt the epidermal skin barrier, emulsify the sebum and enable improved mixing of hydrophilic nanoparticles in aqueous solutions. Further, a concentration of the nanoparticles such as centrifugation or lyophilization may be employed. Further, the nanoparticles may be pretreated with heat or radiation. Also provided is the optional step of conjugating a biological entity or plurality of biological entities to the nanoparticles. Such a conjugating step may involve a thiol, amine, or carboxyl linkage of the biological entities to the nanoparticles.

Diseases and Disorders.

The present disclosure can be used on human (or other animal) skin for the treatment of wrinkles and other changes related to photo-aging or chronologic aging (generally termed skin rejuvenation), for the treatment of diseases including skin diseases, for the reduction of acne and related disorders such as rosacea, folliculitis, pseudofolliculitis barbae or proliferative or papulosquamous disorders such as psoriasis, for the stimulation or reduction of hair growth, and for reduction of cellulite, warts, hypopigmentation such as port-wine stain (PWS; nevus flammeus), birthmarks, hyperhidrosis, varicose veins, pigment problems, tattoos, vitiligo, melasma, scars, stretch marks, fungal infections, bacterial infections, dermatological inflammatory disorders, musculoskeletal problems (for example, tendonitis or arthritis), to improve healing of surgical wounds, burn therapy to improve healing and/or reduce and minimize scarring, improving circulation within the skin, and the like.

The present disclosure can also be useful in improving wound healing, including but not limited to chronic skin ulcers, diabetic ulcers, thermal burn injuries, viral ulcers or disorders, periodontal disease and other dental disease. The present disclosure can be useful in treating the pancreas in diabetes. The present disclosure can be useful for in vitro fertilization enhancement, and the like. The present disclosure, in certain embodiments, is also useful in enhancing the effects of devices that create an injury or wound in the process of performing cosmetic surgery including non-ablative thermal wounding techniques for treating skin wrinkles, scars, stretch marks and other skin disorders. Under such circumstances, it may be preferable to use conventional non-ablative thermal treatments in combination with the methods of the present disclosure. The instant application, in certain embodiments, are used in conjunction with micro- or surface abrasion, dermabrasion, or enzymatic or chemical peeling of the skin or topical cosmeceutical applications, with or without nanoparticle application to enhance treatment, as the removal of the stratum corneum (and possibly additional epithelial layers) can prove beneficial for some treatment regimen. The methods of the present disclosure are particularly applicable to, but are not limited to, acne treatment, hair removal, hair growth/hair follicle stimulation, reduction/prevention of malignant and non-malignant skin tumors, and skin rejuvenation, as described herein.

The dermatologically therapeutic methods described herein may be formed using nanoparticle irradiation alone, nanoparticle irradiation in combination with nano- or microparticles, or nanoparticle irradiation with a composition comprising nano- or microparticles and one or more therapeutic agents. Such nanoparticle irradiation may be produced by any known nanoparticle generator, and is preferably a focused nanoparticle generator capable of generating and irradiating focused nanoparticle waves. Additionally, nanoparticle waves can be focused in tissues to provide damage to local areas with a desirable size and shape.

EXAMPLES

Example 1

Generation of Plasmonic Nanoparticles for Thermomodulation

Plasmonic nanoparticles, including nanorods, hollow nanoshells, silicon nanoshells, nanoplates, nanorice, nanowires, nanopyramids, nanoprisms, nanoplates and other configurations described herein and known to those skilled in the art, are generated in size ranges from 1-1000 nm under conditions such that surface properties that facilitate deep follicular penetration. Surface properties can be varied on one or multiple (2, 3, or 4) different dimensions to increase nanoparticle concentration in a target tissue domain. Penetration into follicular openings of 10-200 um can be maximized using the nanoparticles described herein. Here, nanoparticles sized in the range of about 10 to about 100 nm are generated, and are preferably assembled or formulated into multiparticular structures having a size in the range of 100-300 nm. Alternatively, a coating (e.g., silica) is grown on uniparticular structures to increase the particle size to the range of 100-300 nm or more.

Surface-modified plasmonic nanoparticles. An exemplary preparation of surface-modified plasmonic nanoparticles is provided as follows. Plasmonic nanoparticles are synthesized with stable cetyltrimethylammonium bromide (CTAB) coating and concentrated from an optical density of 1 O.D. to 100, 200, 300, 400, or 500 O.D. through one to three cycles of centrifugation at 16,000 rcf, with supernatant decanting. Alternatively, CTAB-coated nanoparticles are concentrated and resuspended in 250 Amol/L 5-kDa methyl-polyethylene glycol (PEG)-thiol to make PEG-coated nanoparticles. Verification that PEG polymer stocks are fully reduced is performed using spectrophotometry to measure the thiol activity of polymer-thiols with 5,5-dithiobis(2-nitrobenzoic acid) against a DTT gradient. The solution of methyl PEG-thiol and CTAB-coated nanoparticles is mixed at room temperature for 1 h then dialyzed against 5 kDa MWCO in 4 L distilled water for 24 h. Dialyzed samples are processed through 100-kDa filters to remove excess polymer. Quantification of the number of PEG polymers per particle is performed by surface-modifying nanoparticles with amino-PEG-thiol polymer and quantifying the number of amines with an SPDP assay. For test formulations, 100 O.D. solutions of CTAB-coated plasmonic nanoparticles are made in distilled water, and 100 O.D. PEG-coated plasmonic nanoparticles are made in distilled water, ethanol, DMSO, or mineral oil. Plasmonic nanoparticles with silica shells are created by reacting nanoparticles with silicates such as tetra-ethyl-ortho-silicate (TEOS), sodium silicate, aminopropyltriethoxysilane (APTS), etc. to thicknesses of 5-50 nm or more. Control, vehicle-only formulations contain no nanoparticles.

Embedded Nanoparticles.

Nanoparticles are embedded (or encapsulated) in materials, which allows for the generation of a diverse range of sizes to tune their size. Particle sizes in the range of 100-2000 nm or 200-2000 nm have been shown to enter the hair follicle without penetrating the dermis. Nanoparticles are encapsulated in silica, a synthetic polylactide/co-glycolide co-polymer, porous lauryllactame/caprolactam nylon co-polymer, hydroxyethylcellulose, polyelectrolyte monolayers, or alternatively, in natural hydrogels such as hyaluronic acid, without significantly altering plasmon resonance properties. Nanoparticles are embedded within 100-2000 nm materials or 200-2000 nm materials without covalent attachment or by cross-linking of amines, carboxyls or other moieties on the nanoparticle surface to the polymer structure. The surface of the 100-2000 nm material or 200-2000 nm material may be modified for an optimal zeta potential, hydrophilicity/hydrophobicity, and/or adsorption layer through techniques described herein. Furthermore, the shape of the aspect ratio of the polymer can be modified from low to high to increase concentrations and depths of penetration of the embedded plasmonic nanoparticles. The nanoparticles advantageously have an aspect ratio greater than about 1.

Example 2

Formulation of Thermoablative Plasmonic Nanoparticles for Topical Delivery

Nanoparticles are generated as in Example 1 using an appropriate solvent (e.g., water, ethanol, dimethyl sulfoxide). The mixture comprising a plurality of nanoparticles in water is concentrated to about 100-500 O.D. and exchanged for a new solvent by liquid chromatography, a solvent exchange system, a centrifuge, precipitation, or dialysis. The solvent may include an alcohol (e.g., n-Butanol, isopropanol, n-Propanol, Ethanol, Methanol), a hydrocarbon (e.g., pentane, cyclopentane, hexane, cyclohexane, benzene, toluene, 1,4-Dioxane), chloroform, Diethyl-ether, water, an acid (e.g., acetic acid, formic acid), a base, acetone, dimethyl sulfoxide (DMSO), dimethylformamide (DMF), acetonitrile (MeCN), tetrahydrofuran (THF), dichloromethane (DCM) or ethylacetate. The new solvent is combined with a cosmetically or pharmaceutically acceptable carrier, thereby forming a nanoparticle composition. Generally, the particles and carrier will form an emulsion.

Plasmonic nanoparticle formulations are provided that amplify or expedite the penetration of nanoparticles into hair follicles. In some embodiments, nano- and micro-emulsions facilitate partitioning within lipid-rich skin compartments such as the hair follicle. In some embodiments, nanoparticles are formulated in compositions containing 0.5-2% v/v surfactants to enable disruption of the epidermal skin barrier, emulsification of sebum, and improved mixing of hydrophilic nanoparticles in hydrophobic solutions or targeting to hydrophobic space in the skin (e.g. between the hair shaft and surrounding follicle). Formulations of nanoparticles are also provided at various concentrations (1-20% w/v) in aqueous solutions, silicone/oil solvents, polypropylene gel, propylene glycol or creams (e.g. containing alcohols, oils, paraffins, colloidal silicas). In some embodiments, light-absorbing nanoparticles are utilized in solutions having tailored pH, temperature, osmolyte concentration, viscosity, volatility, and other characteristics to improve light-absorbing nanoparticle entry into hair follicles.

Formulations are prepared to maximize nanoparticle stability (degree of aggregation in solution), nanoparticle concentration, and nanoparticle absorbance (degree of laser-induced heating at different concentrations).

Figure 2:
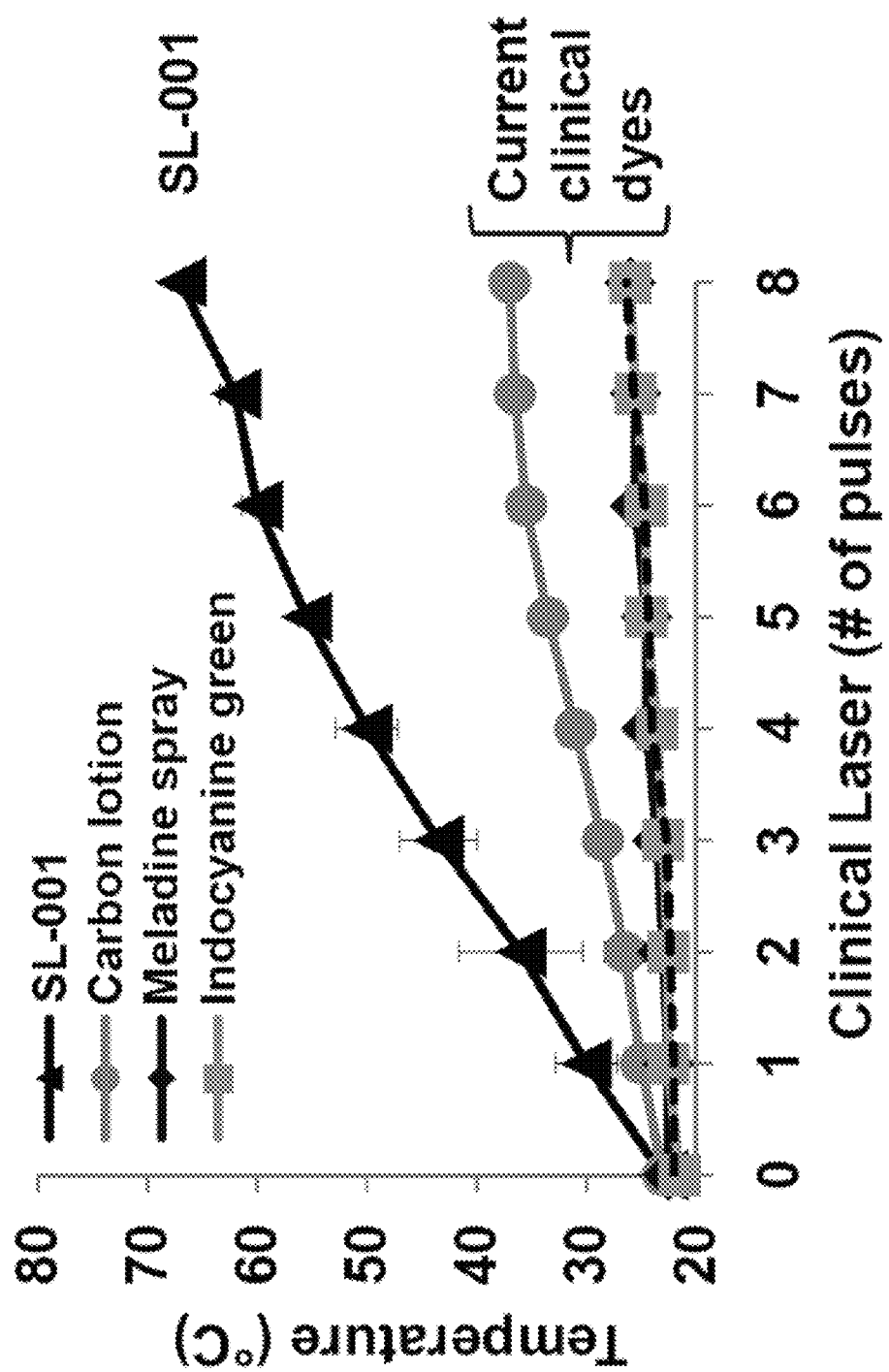
FIG. 2 is illustrative of a temperature profile of certain embodiments of the formulations of plasmonic nanoparticles (SL-001, triangles) provided herein compared to exemplary current clinical dyes carbon lotion (circles), meladine spray (diamonds), and indocyanine green (squares), after exposure to 1064 nm, 20 J/cm$^2$, 55 ms laser pulses. SL-001 and dyes were equally diluted at 1:1000 from clinical concentration (SL-001 1000 O.D., carbon 20-200 mg/ml, meladine 1 mg/ml, ICG 5 mg/ml). n=3, error S.D. of mean.

When formulations of plasmonic nanoparticles are illuminated with a clinical laser with a wavelength coincident to the peak absorption wavelength of the particle, the formulation heats to thermoablative temperatures more rapidly and to a greater degree than conventional clinical absorptive dyes. FIG. 2 compares the temperature profile of plasmonic particles (1020 nm peak absorption wavelength) to conventional clinical dyes carbon lotion, meladine spray and indocyanine green after exposure to 1064 nm, 20 J/cm$^2$, 55 ms laser pulses. The temperature increase caused by pulsed 1064 nm laser light was more than 2.5 times greater for the plasmonic solution, compared to conventional clinical dyes used at the same dilution (1:1000 dilution from clinical concentration, where clinical concentrations are as follows: carbon 20-200 mg/ml, meladine 1 mg/ml, indocyanine green 5 mg/ml).

Example 3

Use of Plasmonic Nanoparticles for Thermomodulation of Hair

Individuals having blonde, red, gray, or lightly-colored hair are not adequately treated with existing light-based hair removal techniques. Provided herein are methods for using the compositions described herein for the selective removal or reduction of untreated blonde, red, gray, or lightly-colored hair. Plasmonic nanoparticles generated and formulated as described above are introduced into a target tissue region, generally a skin region, and activated with laser-based hair removal systems as known in the art in order to achieve effective hair removal.

To achieve maximal penetration depth and concentration of plasmonic nanoparticles in the hair follicle and/or near components of the sebaceous gland including the sebaceous duct, the sebum, the epithelial linking of the sebaceous gland, and/or near the bulge region including the stem cells, stem cell niche, epithelial lining of the bulge region, and/or near the follicular bulb, an optimal particle size of 30-800 nm (e.g., 100-800 nm) containing one or several plasmonic nanoparticles is constructed. Nanoparticles encapsulating plasmonic nanoparticles can be formulated from any number of polymers or matrices. In some embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Preferentially, a matrix component such as silica, polystyrene or polyethylene glycol is provided in the formulation to improve particle stability and enable facile removal from the skin surface after application and follicle targeting. Other formulations include component of surfactants (e.g. sodium dodecyl sulfate, sodium laureth 2-sulfate, ammonium lauryl sulfate, sodium octech-1/deceth-1 sulfate), a lipid bilayer, a liposome, or a microsome. Plasmonic nanoparticles including nanorods, nanoshells, nanospheres, nanoplates, or nanorice can be encapsulated within the polymer or lipid-based nanoparticle or matrix or deposited on the particle surface. Alternatively, nanoparticles in the size range of 100-250 nm, 250-500 nm, 800 nm-1500 nm, or greater than 1500 nm can be used.

Pre-treatment of skin with mechanical or chemical exfoliation is used in some embodiments to remove hair-plugs and "open" the follicle for particle delivery. Additionally, hairs can be shaven or waxed to create a void in the hair follicle for particles to fill. The use of physical or thermal force amplifies or expedites the penetration of light absorbing nanoparticles and conjugates thereof into hair follicles, in part by causing dilation of the hair follicle prior to application of the nanoparticles. For example, ultrasound and other sonic forces, mechanical vibrations, hair shaft manipulation (including pulling), physical force, thermal manipulation, and other treatments are utilized to improve entry of light-absorbing nanoparticles into hair follicles. Nanoparticle formulation treatments are performed alone, in combination, sequentially or repeated 1-24 times.

An applicator is used to uniformly apply the composition of nanoparticles into follicles. The applicator can be a sponge, a cloth, direct contact from a finger, a tube, a syringe, a device that applies suction, an aerosol, a spray, or other means known in the art. In one example, a formulation of 1 ml of plasmonic nanoparticles at a concentration of 100 O O.D. with peak resonance of 810 nm is applied to approximately 200 cm$^2$ area of the skin of an adult human subject with a syringe. A cloth is used to evenly distribute solution across the skin area and into the hair follicles. Deep massage from a mechanical vibrator for 2 minutes with or without 1 MHz ultrasound for 5 minutes, is applied to drive particles deep into the follicle. Particles penetrate 50-75% down the full length of the hair shaft at concentrations sufficient to heat skin in a 100 μm radius at incremental temperatures of 5-20-fold greater than is generated in similar volumes of adjacent skin when irradiated by a Diode (810 nm) laser. Acetone, ethanol, or a debriding agent can be used to remove all particles from the surface of the skin that have not deposited in the follicle, in order to reduced or prevent non-follicular heating of the skin.

Nanoparticle formulations are tested in ex vivo animal samples, ex vivo human skin samples, and in vivo human skin including the assessment of: 1) depth of nanoparticle penetration into hair follicles; 2) particle concentration achieved; 3) degree of heating achieved at delivered nanoparticle concentrations; and 4) efficacy of photothermal destruction including temporary and permanent hair removal, 5) clearance of nanoparticles after treatment. To assess nanoparticle penetration depths, plasmonic nanoparticles surface-functionalized with fluorescent molecules are visualized by fluorescence microscopy after histological sectioning or follicular biopsy (removal of hair shaft). Alternatively, plasmonic nanoparticles are directly visualized by dark field microscopy after histological sectioning or follicular biopsy. To assess nanoparticle concentrations at various depths along the follicle, excised skin samples are separated by tape stripping or heat-based techniques, samples are dissolved for bulk analysis of metal concentration by ICP-MS (inductively coupled plasma-mass spectrometry). The macroscopic degree of heating is validated by infrared thermography of skin samples, and by assessment of skin sections subject to laser exposure for thermal damage markers. Finally, one can measure efficacy of photothermal destruction at the nanoparticle accumulation site by analyzing histological cellular lesions at the target site, including the follicular hair shaft, inner root sheath, outer room sheath, and bulge region containing the stem cell niche, which contains the stem cells that contribute to new hair growth. As the bulge region is generally localized about midway (~50% down the length of) the hair shaft, permanent hair removal is sufficiently achieved by accumulation of plasmonic nanoparticles to this depth. In some situations, nanoparticle delivery may also generate a heat gradient emitting further down the hair shaft. Animal studies are useful to demonstrate the efficacy of unpigmented hair removal by comparing heat profiles, thermal ablation of hair shaft, and thermal damage of bulge stem cells in treated hairless rodents, albino rodents and dark-haired rodents. Efficacy on live human skin is measured by measuring hair counts at 3 and 12 month follow ups. Biopsies are taken from select patients at 2, 4, and 6 week follow ups to verify that nanoparticles are cleared from the skin without embedding in the dermis.

Hair Follicle Penetration of Fluorescently-Labeled Nanoparticles Determined Using Porcine Skin Explants and Confocal Imaging.

Figure 3:
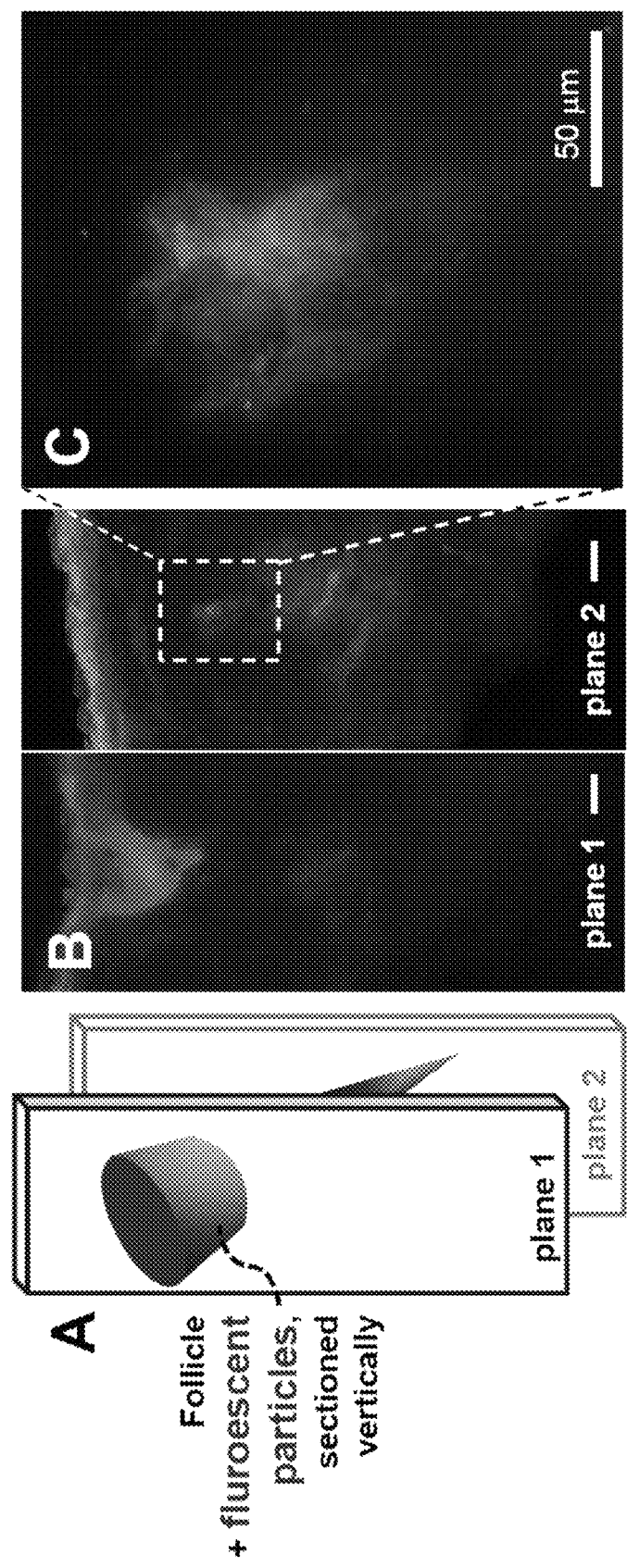
FIG. 3 is illustrative of hair follicle penetration of fluorescently-labeled nanoparticles determined using porcine skin explants and confocal imaging of certain embodiments of the subject matter described herein. Depicted is (A) schematic of treated porcine skin, sectioned and imaged at an angle to the follicle, in two serial 60 μm planes: 'plane 1' (showing follicle infundibulum) and 'plane 2' (showing deep follicle); (B) representative confocal images show red fluorescent nanoparticles (548 nm) within superficial and deep follicle, but not in underlying dermis; and (C) red fluorescent nanoparticles retained in the deep follicle (~400 μm) at high magnification. Green is tissue autofluorescence.

A 25 mg/ml aqueous solution silicon dioxide-coated nanoparticles (200 nm diameter) was contacted with freshly thawed porcine skin, after which excess nanoparticle suspension was removed and manual massage was performed for three minutes. The explant was sectioned and subjected to confocal imaging. As shown in FIG. 3A, explant sections were imaged at angles to the hair follicles in 60 μm planes; Plane 1 shows the follicle infundibulum, while Plane 2 shows the distal regions of the follicle. FIG. 3B demonstrates representative confocal images showing that red nanoparticles (548 nm absorbance) are visible within both the superficial and deep follicles, but are not detectable in dermal layers beneath the follicles. FIG. 3C shows high-magnification imaging of red nanoparticles localized to and retained within a deep follicle (~400 μm). Green color indicates tissue autofluorescence (488 nm).

Hair Follicle Penetration of Plasmonic Nanoparticles Determined Using Porcine Skin and Dark Field Imaging.

Figure 4:
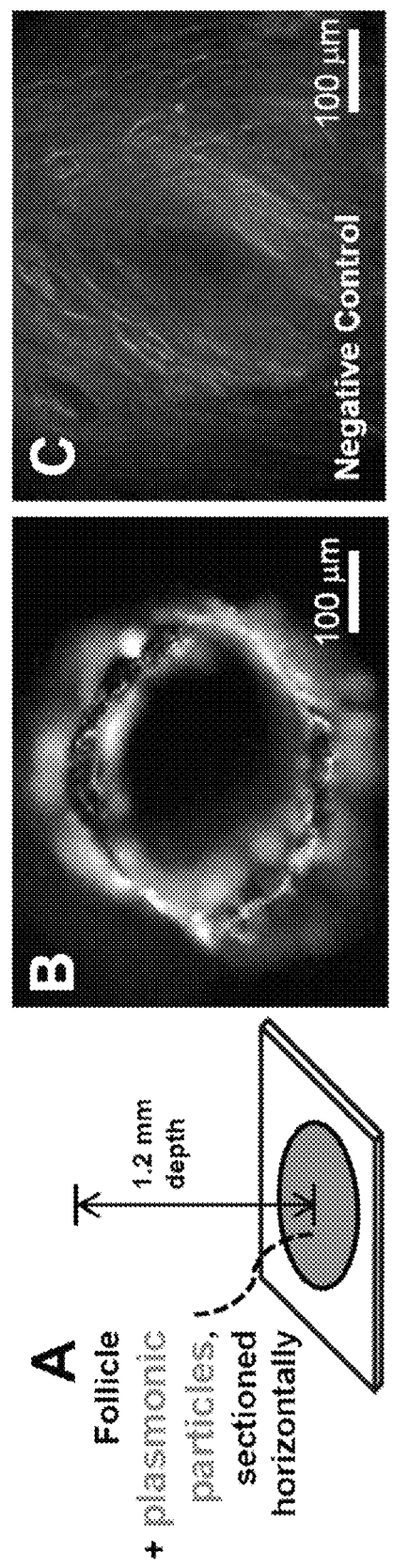
FIG. 4 is illustrative of a hair follicle penetration of plasmonic nanoparticles determined using porcine skin explants and dark field imaging. Shown is (A) schematic of treated porcine skin, sectioned and imaged horizontal to the follicle; (B) bright blue plasmonic particles are visible in a 1.2 mm deep section, and are differentiated from (C) untreated (negative control) porcine skin, where no pigments are visible.

A 100 O.D. suspension of plasmonic nanoparticles (200 nm diameter) was contacted with freshly thawed porcine skin, after which excess nanoparticle suspension was removed and manual massage performed for three minutes. The procedure was repeated for a total of 3 applications, and surface residue removed with several 3-5 applications of alternating water and ethanol. The skin sample was excised, fixed, sectioned along horizontal plane and subjected to dark field imaging. As shown in FIG. 4A, skin samples were sectioned and imaged horizontal to the hair follicle at various depths. In skin section images, plasmonic nanoparticles were observed as bright blue color point sources at depths up to 1.2 mm deep in porcine follicle spaces (FIG. 4B). Control samples with no plasmonic nanoparticles were clearly differentiated (FIG. 4C). ICP-MS is also performed on skin sections to assess nanoparticle concentrations at various depths along the follicle.

Hair Follicle Penetration of Nanoparticles in Hairless Rodents, Albino Rodents and Dark-Haired Rodents.

White-haired Swiss Webster mice (n=3) at 8 weeks old are anesthetized with injectable ketamine/xylazine anesthetic solution and dorsal back skin and hair washed and dried. Prior to formulation administration, three 10 cm×10 cm areas are demarcated by permanent marker on each mouse and subjected to hair removal by 1) electric razor, 2) Nair depilation reagent, or 3) warm wax/rosin mixture application and stripping. Each mouse is treated by pipette with up to 3 nanoparticle formulations, in quadruplicate 5-μl spot sizes per demarcated skin area (up to 12 spots per area or 36 spots per mouse). Precise spot locations are demarcated with pen prior to pipetting. Duplicate treatment spots on the dorsal left side are massaged into skin for 5 minutes, while duplicate treatment spots on the dorsal right side are applied without massage. Thirty minutes after application, mice are sacrificed by carbon dioxide asphyxiation and cervical dislocation, and skin is carefully excised and punched into sections along spot size demarcations. Skin biopsies are fixed in 10% paraformaldehyde, paraffin-embedded, and cut into 5-um sections on a microtome in transverse directions. Slides with mounted paraffin sections are deparaffinized and stained with hematoxylin and eosin (H&E) or kept unstained for dark field microscopy. Using H&E staining, light microscopy and/or dark field microscopy, greater than 50 follicles per formulation are imaged, and scoring is performed for skin sections for visible macroscopic nanoparticle accumulation in the follicle, along the hair shaft, at the site of the putative bulge stem cell niche, and at the depth of the follicle bulb. On serial histological sections, a silver enhancement staining kit based on sodium thiosulfate may be used to enlarge the plasmonic nanoparticle signal via the precipitation of metallic silver. Phase and dark field micrographs are captured and used to record the depths of follicular penetration for each nanoparticle formulation and method of application. ICP-MS is also performed on skin sections to assess nanoparticle concentrations at various depths along the follicle.

Assessment of Photothermal Destruction at the Nanoparticle Accumulation Site.

Treated areas of pig, human or mouse skin are irradiated with a laser coincident with the peak absorption wavelength of nanoparticles (e.g. 1064 nm YAG laser for 1020 nm plasmonic particles) using clinical parameters (1 s exposure of 30-50 $J/cm^2$ and a pulse width of 10-50 ms). To determine microscopic photothermal damage of target skin structures such as the hair follicle and hair follicle bulge stem cells, at ten days after application and irradiation, human subjects receive lidocaine injections to numb treatment areas and skin is carefully excised and punched into sections along spot size demarcations. Fresh human skin biopsies or explanted human and animal skin samples are fixed in 10% paraformaldehyde, paraffin-embedded, and cut into 5-um sections on a microtome in transverse directions, or they are fixed in Zamboni's solution with 2% picric acid and cryo-sectioned by freezing sliding microtome. Slides with mounted paraffin sections are deparaffinized and stained with hematoxylin and eosin (H&E). Histological sections are examined at various depths for markers of thermal damage and inflammation. Hematoxylin and eosin (H&E) is used to image skin and follicle microanatomy and indicate degeneration of hair shafts, atrophy of sebaceous glands, and cell vacuolization (indicating cellular damage). Nitro blue tetrazolium chloride (NBTC), a lactate dehydrogenase stain that is lost upon thermal injury to cells, is used to assess damage to keratinocytes. Cellular damage in follicles of skin samples receiving plasmonic nanoparticle plus laser treatment is scored and compared to those receiving laser treatment alone. Live treated human skin areas are also followed clinically for 2 weeks to 3 months following plasmonic nanoparticle+laser treatment, or during repeated plasmonic nanoparticle+laser treatments, and compared to baseline digital photograph taken prior to first treatment, and to negative control laser only treatments. Clinical observations of hair removal, as well as erythema, edema, discomfort, irritation or scarring, are noted to determine degree of non-specific thermal damage.

Effect of Plasmonic Particle Coating on Specificity of Delivery and Photothermal Heating.

Figure 5:
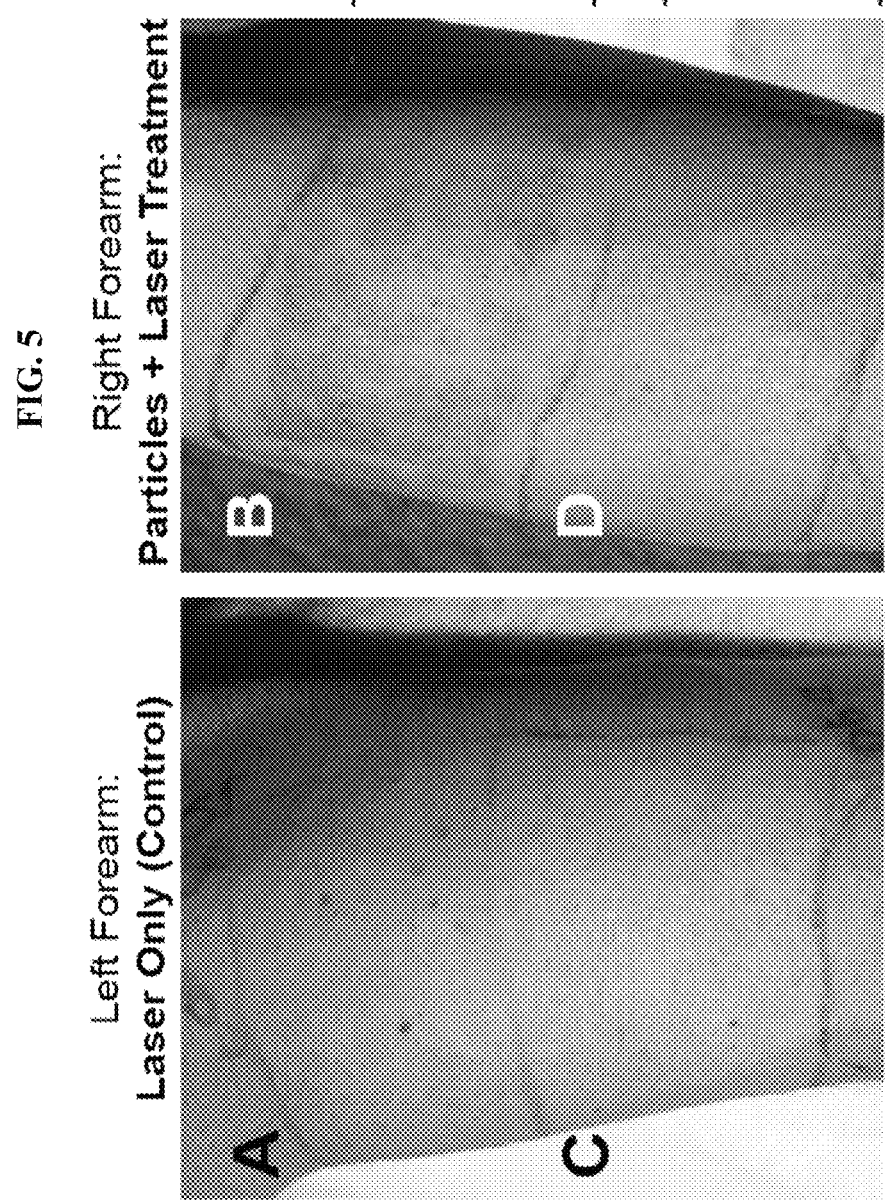
FIG. 5 depicts clinical observations in live human skin treated with Laser Only (left forearm) or Plasmonic Particles+Laser (right forearm) demonstrates non-specific and specific photothermal damage. (A,B) In the top panel, human skin was irradiated with 810 nm laser pulses (30 J/cm2, 30 ms, 2 passes) alone (A), or after treatment with a formulation of 830 nm resonant, Uncoated plasmonic nanoparticles in 20% propylene glycol (B). The plasmonic nanoparticle formulation was applied with 3 minute massage, and the skin surface wiped with 3 applications of alternative water and ethanol before laser irradiation. At 30 minutes following laser irradiation, non-specific clinical burns were observed in B compared to A, due to significant photothermal heating of residual, Uncoated particles on the skin surface. (C,D) In the bottom panel, human skin was irradiated with 1064 nm laser pulses (40 J/cm2, 55 ms, 3 passes) alone (C), or after treatment with a formulation of 1020 nm resonant, Silica-coated plasmonic nanoparticles in 20% propylene glycol (D). The plasmonic nanoparticle formulation was applied with 3 minute massage, and the skin surface wiped with 3 applications of alternative water and ethanol before laser irradiation. At 30 minutes following laser irradiation, no evidence of burning of the skin or erythema was observed in D or C, as Silica-coated particles could be sufficiently wiped from the skin surface. Magnified photography of D showed specific photothermal damage (perifollicular erythema and edema) in the nanoparticle-targeted site.
Figure 6:
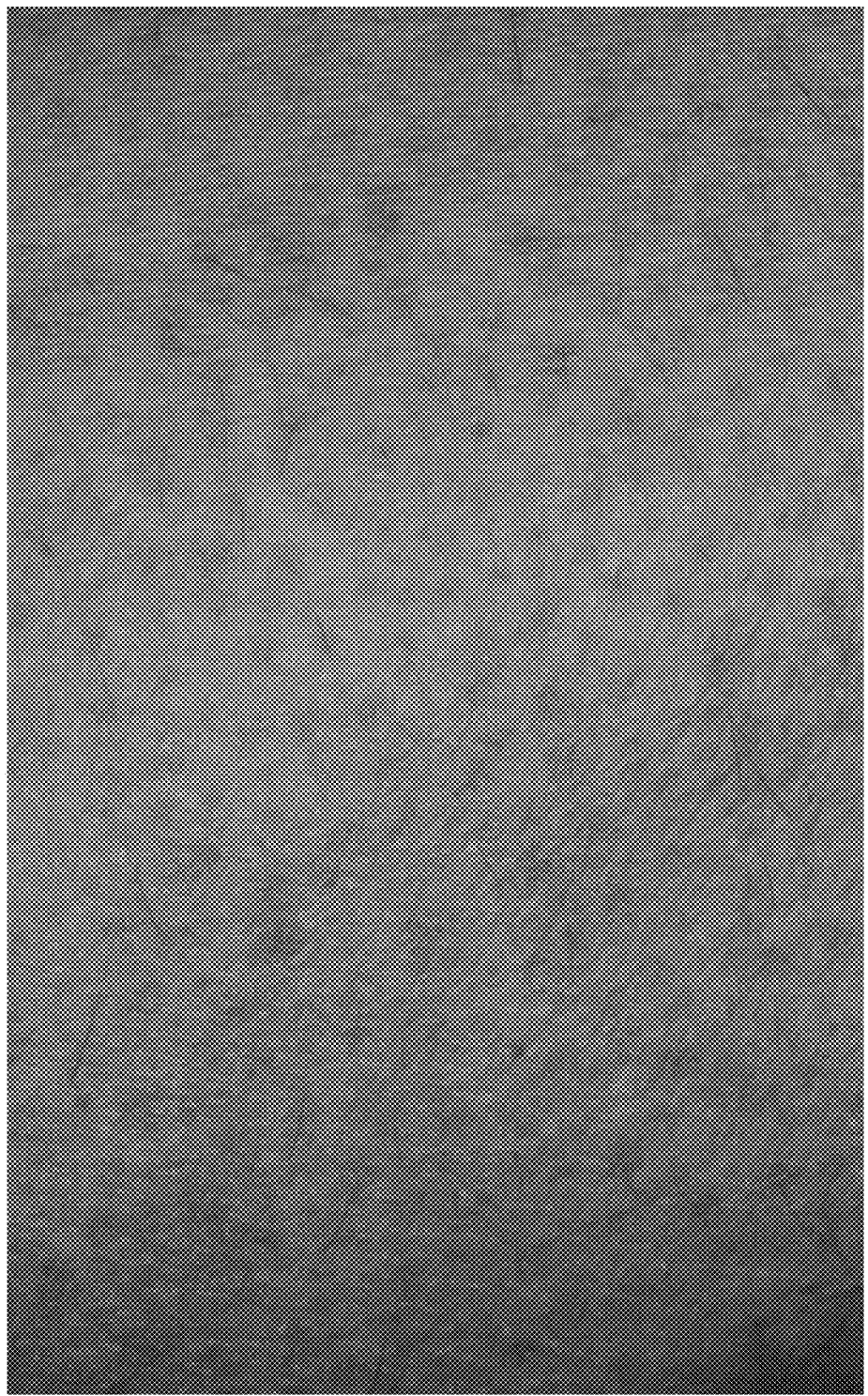
FIG. 6 is a photograph showing nanoparticle-targeted photothermal damage in live human skin treated with a plasmonic nanoparticle formulation and clinical laser. A formulation of 1020 nm resonant, silica-coated (200 nm-diameter) plasmonic nanoparticles in 20% propylene glycol and 3 minute massage was contacted with live human skin. The procedure was repeated 3 times, and skin surface wiped with 3 applications of alternating water and ethanol to remove residual particles. The treated skin was irradiated with 1064 nm laser pulses (40 J/cm$^2$, 55 ms, 3 passes). Following laser irradiation, clinical observation of perifollicular erythema and edema was visible at hair follicles where nanoparticles were targeted, but not visible in surrounding or non-particle-treated tissues.

Preferentially, a matrix component such as silica, polystyrene or polyethylene glycol is provided in the formulation to improve particle stability and enable facile removal from the skin surface after application and follicle targeting. Acetone, ethanol, or a debriding agent can be used to remove all particles from the surface of the skin that have not deposited in the follicle, in order to reduced or prevent non-follicular heating of the skin. In FIG. 5, live human skin was treated with Uncoated plasmonic particles compared to Silica-coated plasmonic particles, prior to laser-irradiation and comparison to no particle treatment (laser only) controls. Pre-treatment of skin, including shaving with razor and microdermabrasion (15 sec, medium setting) to remove hair-plugs and "open" the follicle for particle delivery, was performed on both forearms. Human forearm skin was irradiated with 810 nm laser pulses (30 $J/cm^2$, 30 ms, 2 passes) alone (FIG. 5A), or after treatment with a formulation of 830 nm resonant, Uncoated plasmonic nanoparticles in 20% propylene glycol (FIG. 5B). The plasmonic nanoparticle formulation was applied with 3 minute massage and repeated 3 times, and the skin surface wiped with 3 applications of alternative water and ethanol before laser irradiation. At 30 minutes following laser irradiation, non-specific clinical burns were observed due to significant photothermal heating of residual, Uncoated particles on the skin surface (FIG. 5B). Live human skin was also irradiated with 1064 nm laser pulses (40 $J/cm^2$, 55 ms, 3 passes) alone (FIG. 5C), or after treatment with a formulation of 1020 nm resonant, Silica-coated plasmonic nanoparticles in 20% propylene glycol (FIG. 5D). The plasmonic nanoparticle formulation was applied with 3 minute massage and repeated 3 times, and the skin surface wiped with 3 applications of alternative water and ethanol before laser irradiation. At 30 minutes following laser irradiation, no evidence of burning of the skin or erythema was observed, as Silica-coated particles could be sufficiently wiped from the skin surface (FIG. 5D). Magnified photography of the skin area treated with Silica-coated particles+Laser shows specific photothermal damage (perifollicular erythema and edema) in the nanoparticle-targeted site, without damage to surrounding or non-particle-treated tissues (FIG. 6).

Example 4

Use of Plasmonic Nanoparticles for Acne Treatment

Provided herein are methods for using the compositions described herein for the treatment of acne *vulgaris* and other *acnes* and acne-like skin conditions, but the selective targeting of sebaceous follicles, particularly the sebaceous glands and/or hair follicles. Plasmonic nanoparticles generated and formulated as described above are introduced into a target tissue region, generally a skin region, and activated with laser-based systems as known in the art in order to achieve effective hair removal.

To achieve maximal penetration depth and concentration of plasmonic nanoparticles in the hair follicle and/or near components of the sebaceous gland including the sebaceous duct, the sebum, the epithelial linking of the sebaceous gland, and/or near the bulge region including the stem cells, stem cell niche, epithelial lining of the bulge region, and/or near the follicular bulb, an optimal particle size of 100-800 nm containing one or several plasmonic nanoparticles is constructed. Nanoparticles encapsulating plasmonic nanoparticles can be formulated from any number of polymers or matrices. In some embodiments, the formulation contains a degradable or non-degradable polymer, e.g., synthetic polylactide/co-glycolide co-polymer, porous lauryllactame/caprolactame nylon co-polymer, hydroxyethylcellulose, polyelectrolyte monolayers, or alternatively, in natural hydrogels such as hyaluronic acid, gelatin and others. In further embodiments, a hydrogel PLGA, PEG-acrylate is included in the formulation. Preferentially, a matrix component such as silica, polystyrene or polyethylene glycol is provided in the formulation to improve particle stability and enable facile removal from the skin surface after application and follicle targeting. Preferentially, formulations include surfactants (e.g. sodium dodecyl sulfate, sodium laureth 2-sulfate, ammonium lauryl sulfate, sodium octech-1/deceth-1 sulfate), components of a lipid bilayer, a liposome, or a microsome. Surfactants disrupt the epidermal skin barrier, emulsify sebum, improve mixing of hydrophilic nanoparticles with hydrophobic solutions, and reduce entropic barriers to delivering hydrophilic particles to hydrophobic regions of the skin (e.g. between the hair shaft and surrounding sheath or follicle). Plasmonic nanoparticles including nanorods, nanoshells, nanospheres, or nanorice can be encapsulated within the polymer nanoparticle or matrix or deposited on the particle surface. Alternatively, nanoparticles in the size range of 100-250 nm, 250-500 nm, 800 nm-1500 nm, or greater than 1500 nm can be used.

The use of physical or thermal force amplifies or expedites the penetration of light absorbing nanoparticles and conjugates thereof into hair follicles and/or sebaceous glands, in part by causing dilation of the hair follicle prior to application of the nanoparticles. For example, ultrasound and other sonic forces, mechanical vibrations, hair shaft manipulation (including pulling), physical force, thermal manipulation, and other treatments are utilized to improve entry of light-absorbing nanoparticles into hair follicles and/or sebaceous glands. Nanoparticle formulation treatments are performed alone, in combination, sequentially or repeated 1-24 times.

Prior to application of the plasmonic nanoparticles, a pre-treatment step of removing excess sebum from the surface of the skin may be performed using chemical and/or mechanical means. Pre-treatment of skin with mechanical or chemical exfoliation is used in some embodiments to remove hair-plugs and "open" the follicle for particle delivery. Additionally, hairs can be shaven or waxed to create a void in the hair follicle for particles to fill.

An applicator is used to uniformly apply the composition of nanoparticles into follicles. The applicator can be a sponge, a cloth, direct contact from a finger, a tube, a syringe, a device that applies suction, an aerosol, a spray, or other means known in the art. In one example, a formulation of 1 ml of plasmonic nanoparticles at a concentration of 100 O.D. with peak resonance of 810 nm is applied to approximately 200 $cm^2$ area of the skin of an adult human subject with a syringe. A cloth is used to evenly distribute solution across the skin area and into the hair follicles. Massage from a mechanical vibrator for 2 minutes with or without ultrasound at 1 MHz for 5 minutes is applied to drive particles deep into the follicle. Particles penetrate ~50% down the full length of the hair shaft at concentrations sufficient to heat skin in a 100 um radius at incremental temperatures of 5-20-fold greater than is generated in similar volumes of adjacent skin when irradiated by a Diode (810 nm) laser. Acetone, ethanol, or a debriding agent can be used to remove all particles from the surface of the skin that have not deposited in the follicle, in order to reduced or prevent non-follicular heating of the skin.

Delivery of Plasmonic Nanoparticles to the Sebaceous Gland Determined Using Human Abdominoplasty Skin and Dark Field Imaging.

Figure 7:
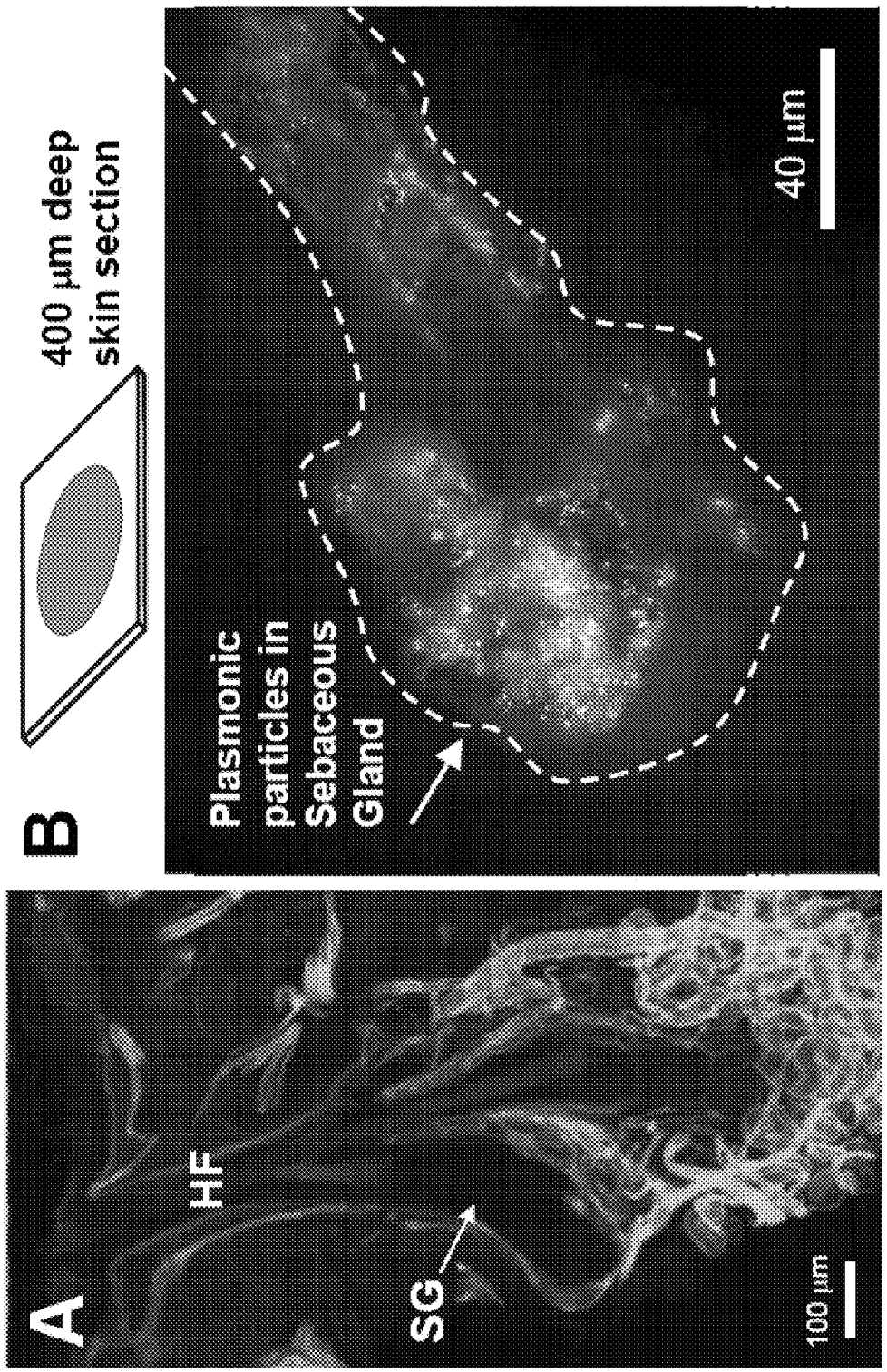
FIG. 7 is illustrative of a plasmonic nanoparticle formulation delivery to human skin sebaceous gland. (A) Confocal microscope image of a human skin biopsy and section, immunostained for Collagen IV basement membrane (blue) and PGP 9.5 nerve marker (green), shows hair follicle (HF) and sebaceous gland (SG) microanatomy. Red is silica nanoparticles (200 nm). (B) Schematic and dark field microscope image of excised human skin treated with plasmonic nanoparticle formulation, then sectioned and imaged horizontal to the follicle. Bright blue plasmonic particles are visible up to 400 μm deep and within the human sebaceous gland.

The human sebaceous gland exists within the pilosebaceous unit consisting of the hair, hair follicle, arrector pili muscle and sebaceous gland. In FIG. 7A, a human skin biopsy is immunostained with antibodies against Collagen IV (basement membrane marker, blue) and PGP 9.5 (nerve marker, green) to visualize representative pilosebaceous unit microanatomy, including the hair follicle (HF), sebaceous gland (SG) and arrector pili muscle. To deliver nanoparticles to the hair follicle and sebaceous gland, skin was first pre-treated with shaving to remove extruding hair, microdermabrasion (15 sec, medium setting) to remove hair-plugs and corneocytes, and chemical depilation to "open" follicle microwells for particle delivery. A 100 O.D. suspension of plasmonic nanoparticles (200 nm diameter), formulated in 1% sodium dodecyl sulfate (SDS) and 20% propylene glycol (PG) was contacted with excised human abdominoplasty skin, after which excess nanoparticle suspension was removed and manual massage performed for three minutes, followed by ultrasound (1 MHz) for 5 minutes. The procedure was repeated for a total of 3 applications, and surface residue removed with 3-5 applications of alternating water and ethanol. The skin sample was excised, fixed, sectioned along horizontal planes and subjected to dark field imaging. As assessed by dark field imaging of horizontal skin sections, compositions of plasmonic nanoparticles with a cosmetically acceptable carrier of 1% SDS/20% PG administered with massage and ultrasound can be delivered 400-600 μm deep into the human follicle and specifically into the sebaceous gland (FIG. 7B).

Cosmetic Formulations for Follicle and Sebaceous Gland Delivery in Human Skin.

Figure 8:
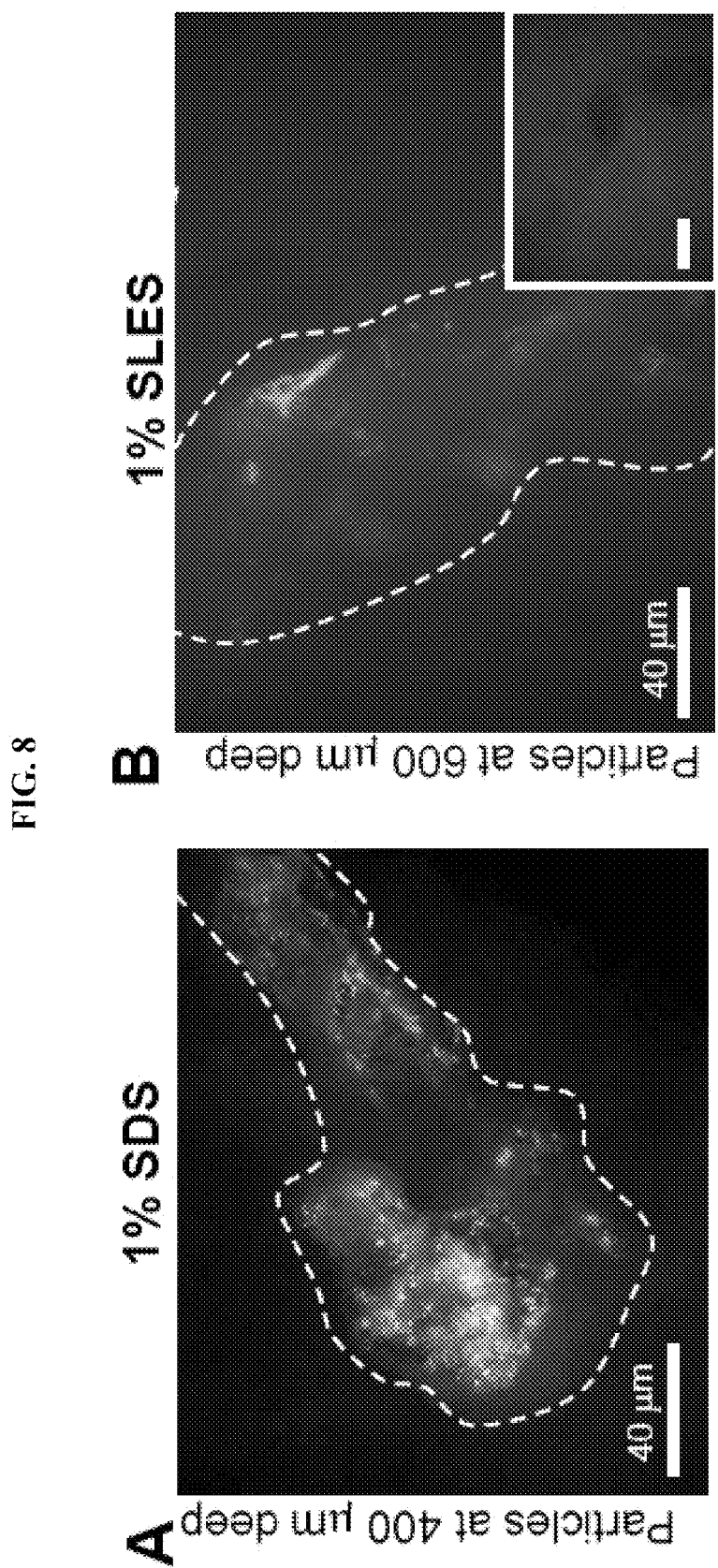
FIG. 8 is illustrative of cosmetic formulations of plasmonic nanoparticles for sebaceous gland targeting that include surfactants. Silica-coated nanoparticles (200 nm diameter, 100 O.D.) were formulated in 20% propylene glycol with the addition of surfactants sodium dodecyl sulfate (SDS) or sodium laureth-2 sulfate (SLES), applied to human skin with massage+ultrasound, and skin was sectioned in horizontal planes for dark field microscopy. (A) Formulations of plasmonic particles in 1% SDS/20% PG penetrated sebaceous gland down to 400 um as in FIG. 7. (B) Formulations of plasmonic particles in 1% SLES/20% PG penetrated sebaceous gland down to 600 um. Inset shows a skin section without visible particles (scale bar 40 um). Sebaceous gland is pseudo-outlined.

Preferentially, formulations include surfactants (e.g. sodium dodecyl sulfate, sodium laureth 2-sulfate, ammonium lauryl sulfate, sodium octech-1/deceth-1 sulfate), components of a lipid bilayer, a liposome, or a microsome. Surfactants disrupt the epidermal skin barrier and emulsify the sebum to enable improved mixing of hydrophilic nanoparticles in hydrophobic solutions. Humectants such as propylene glycol are used to help improve topical viscosity and maintain physiological pH. To demonstrate the efficacy and mechanism of exemplary cosmetic formulations for human sebaceous gland delivery, skin was first pre-treated with shaving to remove extruding hair, micro dermabrasion (15 sec, medium setting) to remove hair-plugs and corneocytes, and chemical depilation to "open" follicle microwells for particle delivery. Two separate 100 O.D. suspensions of plasmonic nanoparticles (200 nm diameter) were formulated in 1% sodium dodecyl sulfate and 20% propylene glycol (SDS/PG) or in 1% sodium laureth-2-sulfate and 20% propylene glycol (SLES/PG). Formulations were contacted with two separate excised human abdominoplasty skin samples, and massage for 3 minutes followed by ultrasound (1 MHz) for 5 min was performed to drive particles deep into the follicles. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of plasmonic nanoparticles with a cosmetically acceptable carrier of 1% SLES/20% administered with massage and ultrasound can be delivered 400-600 µm deep into the human follicle and specifically into the sebaceous gland (FIG. 8B).

Impact of Massage Vs. Ultrasound on Nanoparticle Delivery to Human Follicles and Sebaceous Grid.

Figure 9:
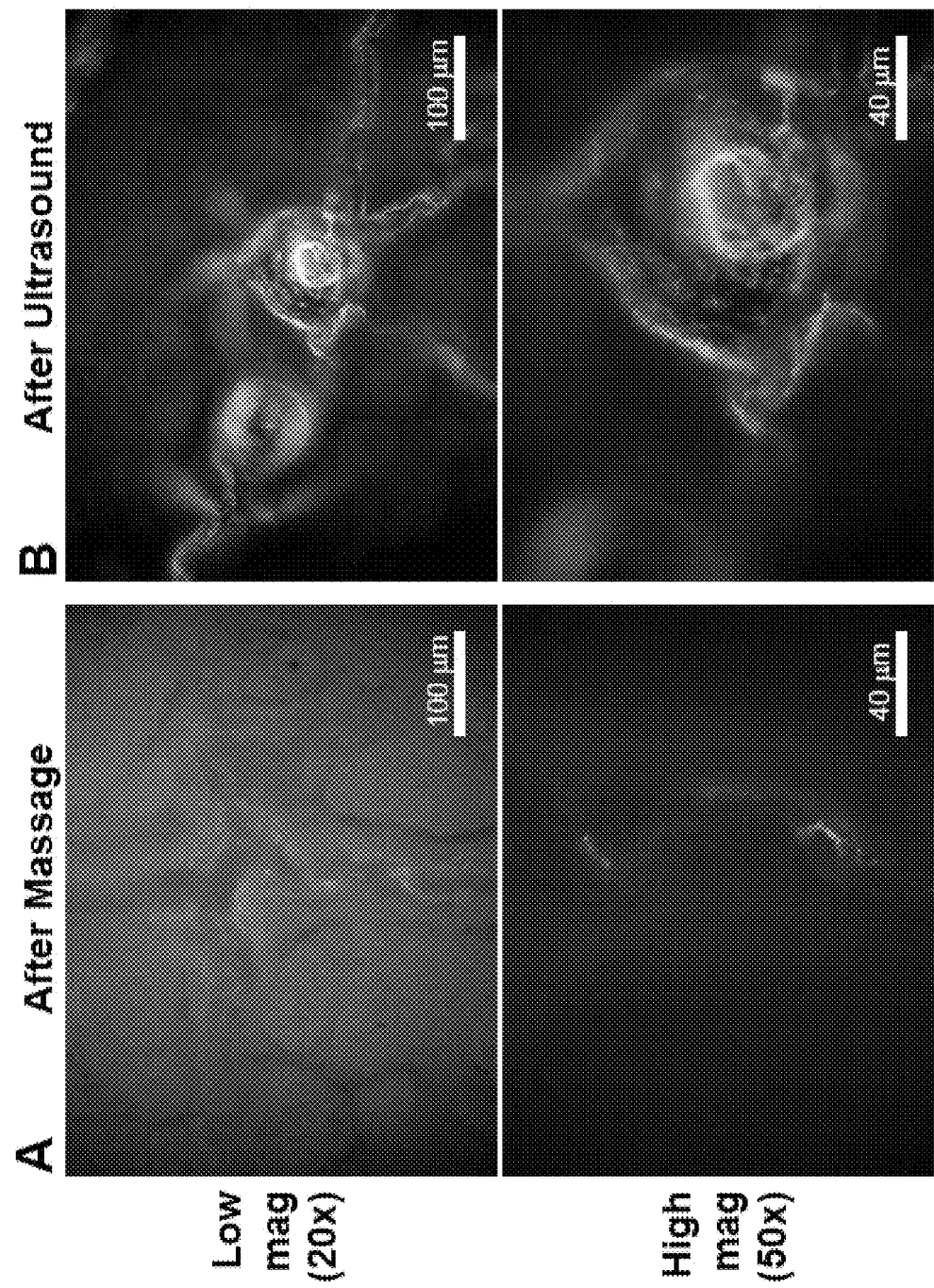
FIG. 9 is an image depicting impact of massage vs. ultrasound on nanoparticle targeting to the human follicle and sebaceous gland. Silica-coated nanoparticles (200 nm diameter, 100 O.D.) were formulated in 1% SDS/20% propylene glycol and applied to human skin with massage or ultrasound. Dark field images of horizontal planar sections taken at low (20×) and high (50×) magnification show (A) little to no accumulation of plasmonic particles into follicle infundibulum after massage alone, compared to (B) follicle infundibulum expansion and significant plasmonic particle accumulation after ultrasound alone.

Ultrasound and other sonic forces, mechanical vibrations, hair shaft manipulation (including pulling), physical force, thermal manipulation, and other treatments are utilized to improve entry of light-absorbing nanoparticles into hair follicles and/or sebaceous glands. Mechanical massage improves follicular penetration through hair shaft 'pumping' mechanisms, while ultrasound enhances transdermal drug delivery through temporary disruption of the skin's lipid bilayer, bubble formation, and liquid microstreaming. To characterize the effects of massage decoupled from ultrasound, skin was first pre-treated with shaving to remove extruding hair, micro dermabrasion (15 sec, medium setting) to remove hair-plugs and corneocytes, and chemical depilation to "open" follicle microwells for particle delivery. A 100 O.D. suspension of plasmonic nanoparticles (200 nm diameter), formulated in 1% sodium dodecyl sulfate (SDS) and 20% propylene glycol (PG), was contacted with three separate excised human abdominoplasty skin samples. In the three treated human skin samples, massage only was performed for 3 minutes, ultrasound only (1 MHz) was performed for 5 minutes, or massage followed by ultrasound was performed to drive particles deep into the follicles. In a fourth sample, no particles were applied to skin. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of plasmonic nanoparticles with a cosmetically acceptable carrier of 1% SLES/ 20% administered via ultrasound deliver more plasmonic nanoparticles to the infundibulum versus massage, albeit both mechanisms facilitate delivery (FIG. 9).

Additional Plasmonic Nanoparticle Formulations for Follicle and Sebaceous Land Delivery in Human Skin.

Figure 10:
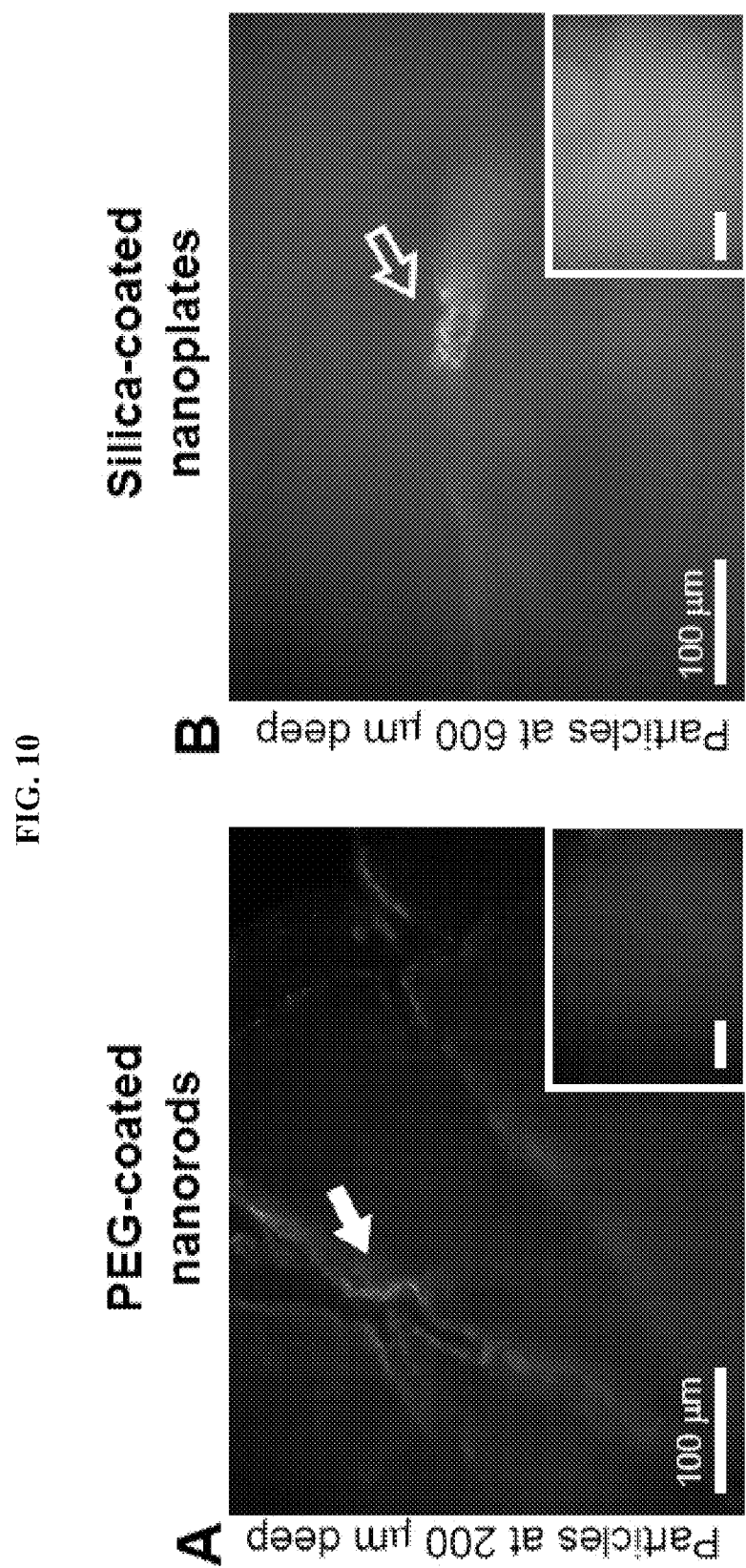
FIG. 10 depicts an embodiment of the plasmonic nanoparticle cosmetic formulations for sebaceous gland targeting. Plasmonic nanoparticles comprising different shapes and coatings were formulated in 1% SDS/20% propylene glycol and applied to human skin with massage+ultrasound, and skin was sectioned in horizontal planes for dark field microscopy. (A) Polyethylene glycol (PEG)-coated nanorods (gold, 15×30 nm dimension) were observed within the follicle infundibulum up to 200 um deep (white arrow). (B) Lower concentration (10 O.D.) Silica-coated nanoplates (silver, 200 nm diameter) were observed up to 600 um deep in the follicle and in the sebaceous gland (open arrow). Inset shows skin sections without visible particles (scale bar 100 um).

In some embodiments, plasmonic nanoparticles include nanorods, nanoshells, nanospheres, or nanorice, or plasmonic nanoparticles encapsulated within the polymer nanoparticle or matrix or deposited on the particle surface. Preferentially, a matrix component such as silica, polystyrene or polyethylene glycol is provided in the formulation to improve particle stability and enable facile removal from the skin surface after application and follicle targeting. To demonstrate the formulation of additional plasmonic nanoparticle shapes and concentrations for follicle, infundibulum, and sebaceous gland delivery, skin was first pre-treated with shaving to remove extruding hair, microdermabrasion (15 sec, medium setting) to remove hair-plugs and corneocytes, and chemical depilation to "open" follicle microwells for particle delivery. Separately, 10 O.D. suspensions of Silica-coated nanoplates, 30 O.D. suspensions of polyethylene-glycol coated plasmonic nanorods, and fluorescent silica particles were formulated in 1% sodium dodecyl sulfate and 20% propylene glycol. Formulations were contacted with three separate excised human abdominoplasty skin samples, and massage for 3 minutes followed by ultrasound (1 MHz) for 5 min was performed to drive particles deep into the follicles. The procedure was repeated for a total of 3 applications, and surface residue removed with 3-5 applications of alternating water and ethanol. The skin sample was excised, fixed, sectioned along horizontal planes and subjected to dark field imaging to assess particle delivery. As assessed by dark field imaging of horizontal skin sections, compositions of Polyethylene glycol (PEG)-coated nanorods (gold, 15×30 nm dimension) in cosmetically acceptable carrier, administered via ultrasound and massage, were observed within the follicle infundibulum at 200 um deep (FIG. 10A). Compositions of plasmonic nanoparticles (Silica-coated nanoplates) at lower concentration (10 O.D.), were apparent at 400-600 um deep in the follicle and in the sebaceous gland (open arrow), albeit at lower concentration than comparable particles in a similar cosmetic carrier at 100 O.D (FIG. 10B).

Assessment of photothermal destruction of sebaceous gland and targeted skin structures. Nanoparticle formulations are tested in ex vivo animal skin samples, ex vivo human skin samples, and in vivo human skin as described in Example 3. One can measure efficacy of photothermal destruction at the nanoparticle accumulation site by measuring thermal damage to sebocytes and reduction in sebum production in the treated sebaceous follicles. To assess photothermal destruction, human skin is first pre-treated with shaving to remove extruding hair, microdermabrasion (15 sec, medium setting) to remove hair-plugs and corneocytes, and chemical depilation to "open" follicle microwells for particle delivery. Skin is contacted with a 100 O.D. suspension of 810 nm resonant plasmonic nanoparticles (200 nm diameter), and is massaged for 3 minutes followed by ultrasound (1 MHz) for 5 min to drive particles deep into the follicles. The procedure is repeated for a total of 3 applications, and surface residue removed with 3-5 applications of alternating water and ethanol. Treated human skin samples are laser irradiated with 810 nm laser (40 J/cm$^2$, 30 ms, 5 pulses), and compared to laser only treated human skin. Human skin is biopsied, fixed in Zamboni's solution with 2% picric acid, and cryosectioned by freezing sliding microtome. Slides with mounted paraffin sections are deparaffinized and stained with hematoxylin and eosin (H&E). Histological sections are examined at various depths for markers of thermal damage and inflammation. Hematoxylin and eosin (H&E) is used to image skin and follicle microanatomy and indicate degeneration of hair shafts, atrophy of sebaceous glands, and cell vacuolization (indicating cellular damage). Nitro blue tetrazolium chloride (NBTC), a lactate dehydrogenase stain that is lost upon thermal injury to cells, may also be used to assess damage to keratinocytes vs. sebocytes. An intracellular stain, Oil-Red-O, may be used to determine lipid and sebum oil content in treated samples. Sebum excretion rates are measured on in vivo skin at 1-3 months follow up using sebum-absorbent tapes to demonstrate functional change in sebum flow. Clearance and prevention of acne lesions is measured by patient reported outcomes and counting acne lesions at 1-3 months follow up.

Example 5

Formulation of Thermoablative Plasmonic Nanoparticles for Vascular Ablation

Formulations are prepared to maximize nanoparticle stability (degree of aggregation in solution), nanoparticle concentration, and nanoparticle absorbance (degree of laser-induced heating at different concentrations) once injected into the blood stream. Nanoparticles are generated as in Example 1 using an appropriate solvent. The mixture comprising a plurality of nanoparticles in water is concentrated to about 100-500 OD at peak absorbance and exchanged for a new solvent by liquid chromatography, a solvent exchange system, a centrifuge, precipitation, or dialysis. Typical exchange solvent is 0.15 mol/L NaCl, 0.1 mol/L Na phosphate buffer (pH 7.2).

Example 6

Use of Plasmonic Nanoparticles for Thermoablation of Component(s) of Vessels and Microvessels Nanoparticle-containing compositions are administered, typically intravascularly. Subsequent to such administration of plasmonic nanoparticles, a laser matched to the peak plasmonic resonance of the particles (e.g., 755 nm, 810 nm, or 1064 nm) is applied to heat nanoparticles and surrounding tissue. Pulse widths of 10-100 ns, 100 ns-1 ms, 1-10 ms, 10-100 ms, 100-1000 ms or continuous wave irradiation is used to achieve thermal heat gradients and localized heating in the vicinity of particle or particles of 20-200 nm. 200 nm-2 µm, 2-20 µm, 20-200 µm, 200 µm-2 mm. Thermal gradients of 20-200 nm are achieved from individual particles. Supra millimeter thermal gradients are achieved by the collective heat deposition of many particles in veins with diameters of several hundred microns or more. Irradiation is applied from 1 pulse to many pulses over seconds to minutes. A cooling device for epidermal layers is used concomitant to irradiation to reduce pain and prevent thermal damage elsewhere. Laser position, fluence, wavelength, angle of incidence, pattern of irradiation is modified to achieve irradiation of vessels at specific depths between 0-10 mm, while avoiding heating of non-target vasculature. Alternatively, laser or light is administered through fiber optic waveguide administered via a catheter to heat the particles in larger veins.

In one embodiment a flank of the tissue is irradiated with 2 W/cm$^2$, 810 nm, 1 cm beam diameter after injection of PEG-nanorods with peak plasmon resonance at 810 nm. Thermographic imaging is used to assess surface temperature of tissue immediately after irradiation.

Assessment of thermal damage to component(s) of vessels, microvessels, or capillaries. Thirty minutes after application, target vessels and the surrounding supporting tissue (e.g. skin) are removed. Biopsies are fixed in 10% paraformaldehyde, paraffin-embedded, and cut into 5-um sections on a microtome in transverse directions. Slides with mounted paraffin sections are deparaffinized and stained with hematoxylin and eosin (H&E) or silver enhancement staining. Using H&E staining and light microscopy, one or several vessels, microvessels, and capillaries can be imaged. Scoring is performed for visible thermal damage of the vessel structures. Additionally, vessel staining (e.g. CD31 stain) is performed to clearly identify vascular structures within tissue samples.

Example 7

Determination of Efficiency of Conversion of Light to Thermal Energy

Figure 11A:
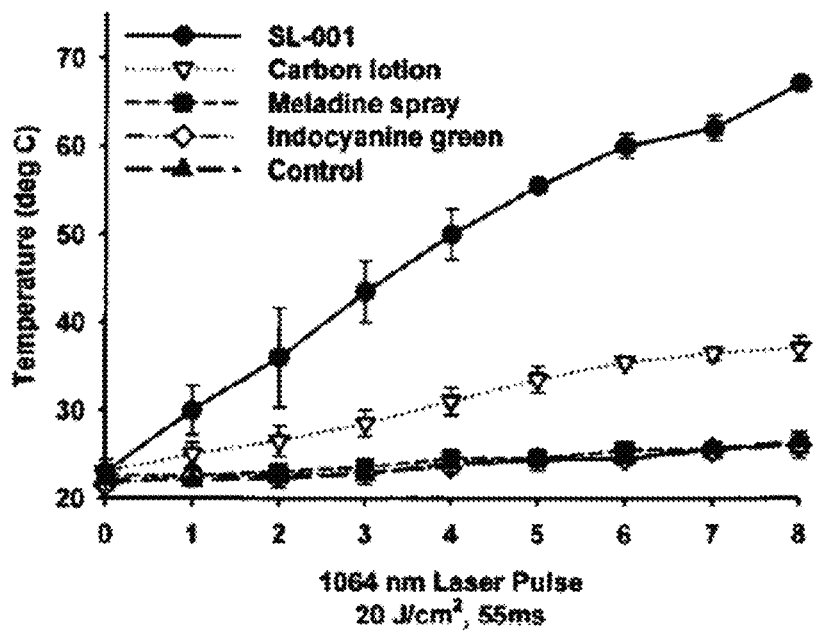
FIG. 11A is illustrative of temperature profiles of certain embodiments of plasmonic nanoparticle formulations compared to other commercial and research chromophores.
Figure 11B:
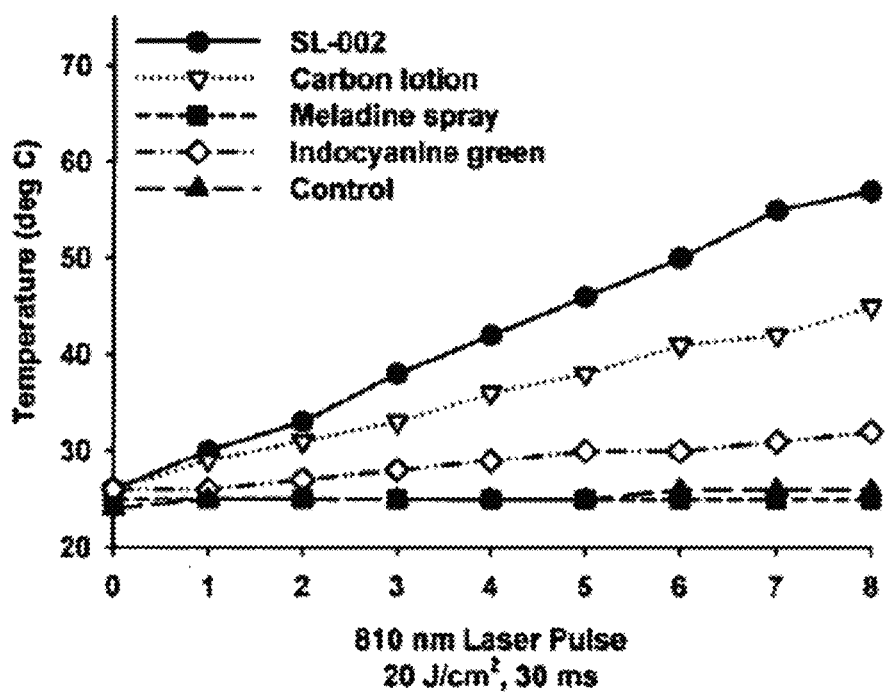
FIG. 11B is illustrative of temperature profiles of certain embodiments of plasmonic nanoparticle formulations compared to other commercial and research chromophores.

A suspension of plasmonic nanoparticles (silica-coated nanoplates having a diameter of about 100-200 nm, as described here) was prepared by formulating the plasmonic nanoparticles in 20% propylene glycol in water to a concentration of about 1000 O.D., and the ability of this suspension to convert laser light to thermal energy was determined. Available commercial and research products, e.g., stock solutions of carbon lotion (20-200 mg/ml carbon, TelsarSoftLight), Meladine spray (1 mg/ml melanin, Creative Technologies), Indocyanine green (5 mg/ml in water, Sigma Aldrich), and vehicle control (20% propylene glycol in water) were also tested. All solutions were diluted 1:1 000 from their indicated stock solution concentration, loaded at 90 µl per well into a 96-well plate, and baseline temperatures were measured by K thermocouple with micrometer (Ex-Tech Instruments, Waltham Mass.) and recorded. Solutions were then irradiated with repeated laser pulses at various wavelengths (e.g., 1064 nm, 810 nm, and 755 nm), fluence (e.g., 10, 20, and 30 J/cm2) and pulse sequence parameters (e.g., 30 ms and 55 ms). Following each sequential laser pulse, up to a total of 8 pulses, solution temperatures were measured and recorded. As shown in FIGS. 11A-11B, a series of plasmonic nanoparticle (PNP) formulations (labeled SL-001 and SL-002) exhibited ultra-high absorption compared to existing commercial and research chromophores. (FIGS. 11A, B) Rate of temperature increase over sequential laser pulses for PNP formulation SL-001 (FIG. 11A, closed circle), resonant at 1064 nm laser wavelength, upon irradiation with 1064 nm laser (A), and SL-002 (FIG. 11B closed circle), resonant at 810 nm laser wavelength, upon irradiation with 810 nm laser (B). Control solutions are as follows: Carbon lotion (open triangle), Meladine spray (closed square), Indocyanine green (open diamond), and 20% propylene glycol (closed triangle). All solutions were diluted 1:1000 from stock clinical concentration for laser irradiation and temperature measurements. For A, n=2 and error bars are s.d. of the mean.

Example 8

Figure 12A:
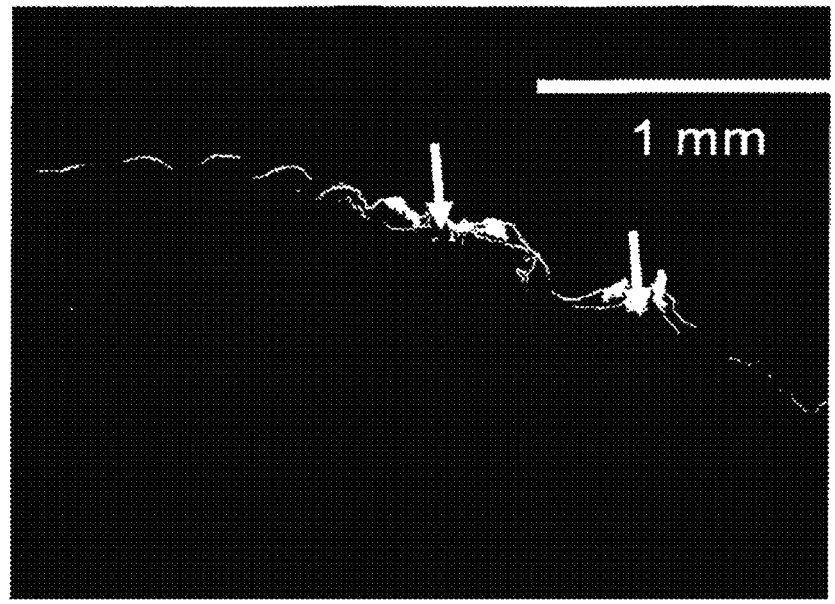
FIGS. 12A and 12B are images of embodiments of nanoparticle formulations in porcine skin.
Figure 12B:
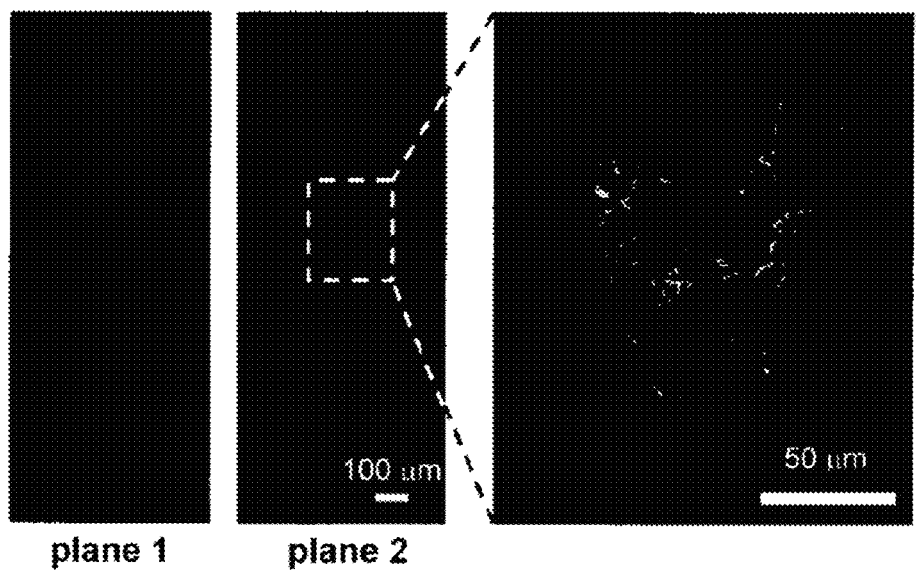

Quantitation of nanoparticle delivery into target tissues. Red fluorescent nanoparticles (Corpuscular Inc., Cold Spring, N.Y.) were contacted with isolated porcine skin explants as follows. A 2.5 mg/ml solution of SiO$_2$, 200 nm diameter, 548 nm emission particles in 20% propylene glycol was pipetted onto the skin surface and mechanically massaged into the tissue explant. An ethanol wipe was used to remove non-penetrating particles. As shown in FIGS. 12A-12B, the provided formulations of nanoparticles (NPs) deeply and specifically penetrate ex vivo porcine skin. FIG. 12A demonstrates representative survey fluorescence image of porcine skin, treated with red fluorescent NPs and histologically sectioned. Red (light contrast) NPs are imaged after penetrating the hair follicle infundibulum (arrows) and deep follicle, but not in the underlying dermis. FIG. 12B shows representative confocal images show red NPs within superficial and deep follicle (−870/−tm) at high and low magnification. Green (dark contrast) is tissue autofluorescence (488 nm emission). Scale bars as labeled 1 mm (A), 10 μm (B, left), 50 μm (B, right).

Figure 13A:
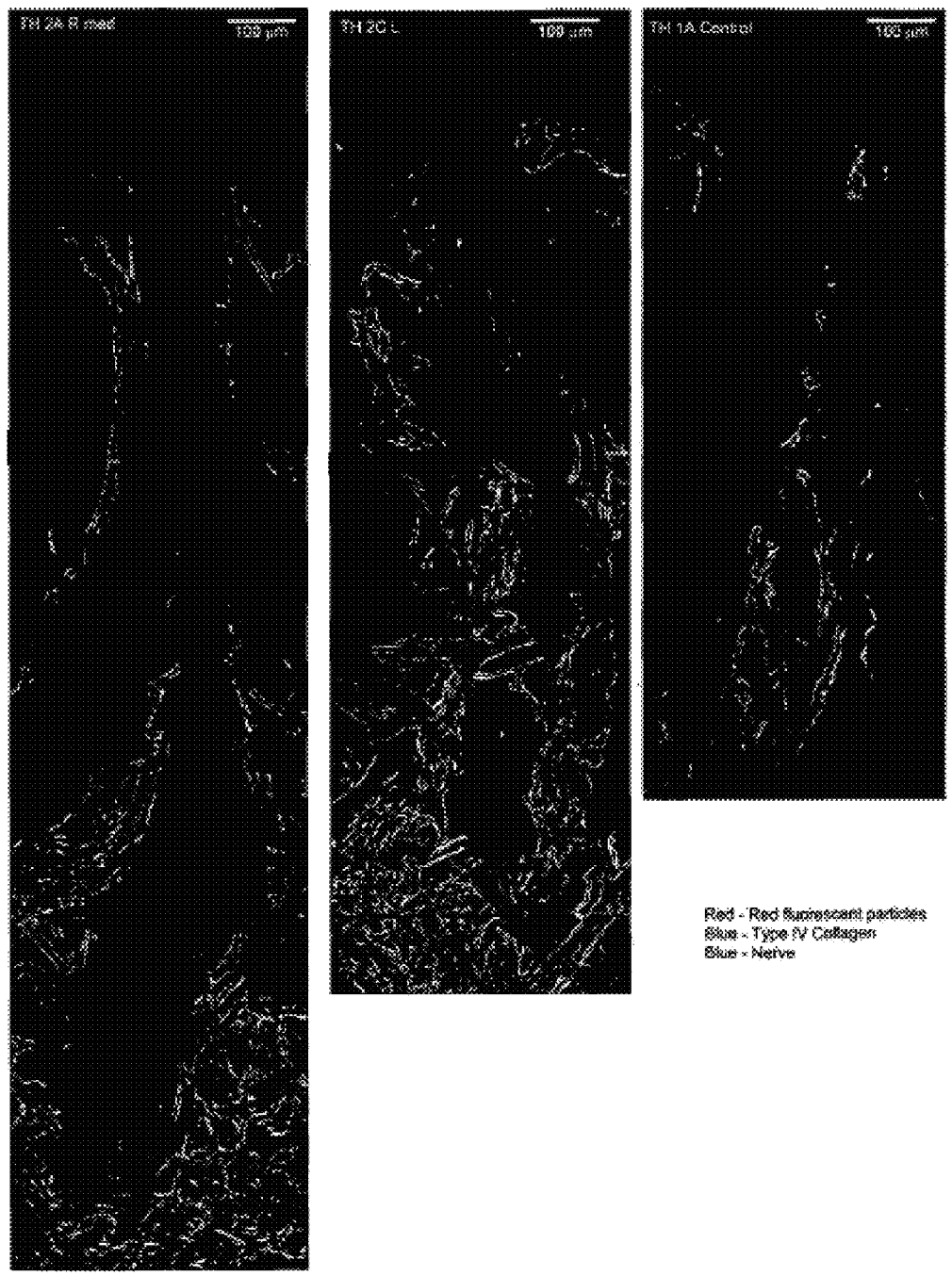
FIGS. 13A and 13B are images of biopsies taken from in vivo-treated human skin, which were sectioned and immunostained for skin markers, with various embodiments of nanoparticles.
Figure 13B:
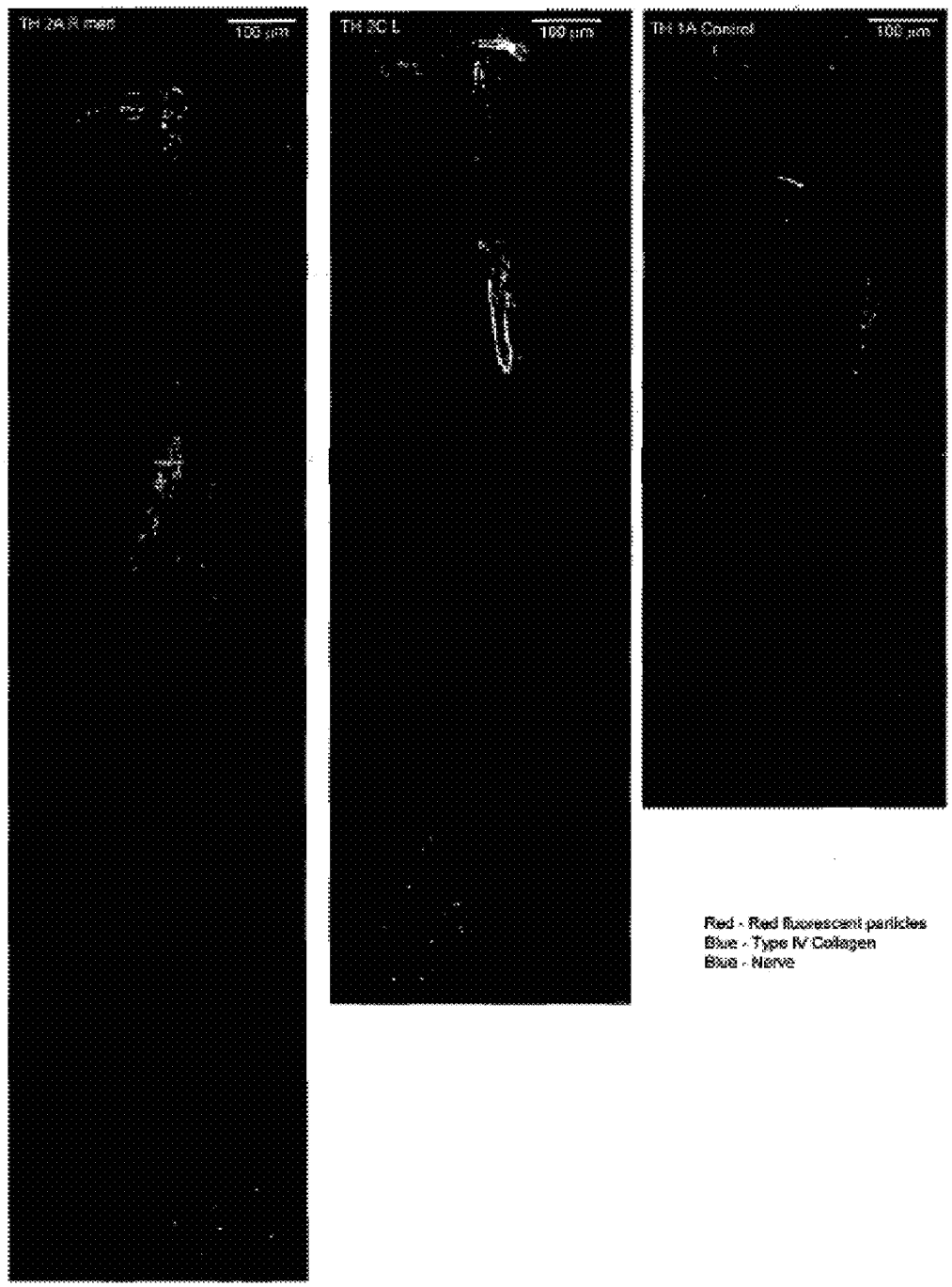

Further, formulations of nanoparticles (NPs) with silica coating deeply and specifically penetrate in vivo human skin. A region of an upper arm of a male human subject having skin Type 3 was treated with the red nanoparticles essentially as described above. Shown in FIGS. 13A and 13B are representative confocal images of biopsies taken from the in vivo-treated human skin, which were sectioned and immunostained for skin markers. Left-'TH 2A R med' sample shows red hair follicle fluorescence after red NP application with massage, ultrasound, and no pre-depilation with waxing; Middle 'TH 2C L' sample shows red hair follicle fluorescence after red NP application with massage, ultration, and pre-depilation with waxing; Right—'TH 1A Control' shows background red autofluorescence of hair follicle. FIG. 13A is 3 color image where red is NPs, blue is collagen IV (staining basement membrane) and green is PGP 9.5 (staining nerve fiber). FIG. 13B shows red channel only in black and white. Scale bars as labeled 100 μm.

As will be understood by the skilled artisan, the subject matter described herein may be embodied in other specific forms without departing from the spirit or essential characteristics thereof. The foregoing embodiments are therefore to be considered in all respects illustrative rather than limiting on the invention described herein.

What is claimed is:

1. A method of localizing thermal damage to a targeted component of a skin tissue, comprising:
    topically applying a composition of nanoparticles to a skin surface of a skin tissue,
    wherein the skin tissue comprises a targeted component of the skin tissue and a non-targeted component of the skin tissue,
    wherein the nanoparticles comprise a conductive metal portion,
    wherein the conductive metal portion comprises at least one of gold, silver, and platinum,
    wherein the nanoparticles comprise a coating that coats the conductive metal portion, wherein said coating is selected from the group consisting of a hydrophilic coating and a hydrophobic coating;
    wherein the nanoparticles are unassembled,
    wherein the nanoparticles have a concentration selected from the group consisting of: $10^9$, $10^{10}$, $10^{11}$, $10^{12}$, and $10^{13}$ particles per ml of the composition;
    distributing a portion of the composition from the non-targeted component of the skin tissue to the targeted component of a skin tissue while a remaining portion of the composition is left on the on-targeted component of the skin tissue;
    removing the remaining portion of the composition from the non-targeted component of the skin tissue; and
    irradiating the composition with an energy wavelength selected from the group consisting of: 755 nm, 800-810 nm, and 1064 nm, thereby inducing a surface plasmon in said nanoparticles, thereby localizing thermal damage to said targeted component of the skin tissue.

2. The method of claim 1,
    wherein the coating is a non-metal coating,
    wherein the conductive metal portion comprises at least one of gold and silver, and
    wherein the nanoparticles have a concentration wherein the nanoparticles have a concentration selected from the group consisting of: $10^9$, $10^{10}$, $10^{11}$, and $10^{12}$ particles per ml of the composition.

3. The method of claim 1, wherein the nanoparticles are plasmonic and comprise an optical density of 10 O.D. to 5,000 O.D. at an infrared peak absorption wavelength selected from the group consisting of: 755 nm, 800-810 nm, and 1064 nm.

4. The method of claim 1,
    wherein the conductive metal portion is a nanoplate,
    wherein the coating is less conductive than the conductive metal portion,
    wherein the coating is a non-metal coating, and
    wherein the nanoparticles comprise an optical density of 10 O.D. to 5,000 O.D. at an infrared peak absorption wavelength selected from the group consisting of: 755 nm, 800-810 nm, and 1064 nm.

5. The method of claim 1, further comprising:
    pre-treating the non-targeted component of the skin tissue, prior to irradiating, to increase distribution from the non-targeted component of the skin tissue to the targeted component of the skin tissue, wherein pre-treating the skin surface comprises at least one of the group consisting of: hair removal, fractionated photothermolysis laser treatment, heating, mechanical exfoliation, and chemical exfoliation.

6. The method of claim 1, wherein distributing the composition of nanoparticles comprises distribution with at least one of the group consisting of an ultrasound device and a massage device, wherein the composition comprises a cream or a gel.

7. The method of claim 1, wherein the conductive metal portion is a nanoplate, wherein the nanoplate has a size in at least one dimension in a range of 10 to 100 nm, and wherein the nanoplate has a peak absorption wavelength selected from the group consisting of: 755 nm, 800-810 nm, and 1064 nm.

8. The method of claim 1, wherein the conductive metal portion is a nanoplate, wherein the coating comprises any one or more of silica and polyethylene glycol (PEG), wherein the nanoplate has a dimension in a range of 1-1,000 nm.

9. The method of claim 1, wherein the composition comprises a cream or a gel, and wherein the targeted component of the skin tissue comprises one or more structures consisting of: a scar, a hair shaft, a hair follicle, a sebaceous gland, and a hair follicle infundibulum.

10. A method of localizing thermal damage to a targeted component of a skin tissue, comprising:
    topically applying a composition of nanoparticles to a skin surface of a skin tissue;
    wherein the skin tissue comprises a targeted component of the skin tissue, wherein the composition of nanoparticles has at least one peak absorption wavelength selected from the group consisting of: 755 nm, 800-810 nm, and 1064 nm, wherein the nanoparticles have a concentration selected from the group consisting of: $10^9$, $10^{10}$, $10^{11}$, $10^{12}$, and $10^{13}$ particles per ml of the composition, wherein the nanoparticles comprise a conductive metal portion, wherein the conductive metal portion comprises at least one of gold, silver, and platinum, wherein the nanoparticles comprise a coating that coats the conductive metal portion, wherein said coating is selected from the group consisting of a hydrophilic coating and a hydrophobic coating;

wherein the nanoparticles are unassembled, targeting the targeted component of the skin tissue by redistributing a portion of the composition of nanoparticles from the skin surface to the targeted component of the skin tissue while a remaining portion of the composition is left on the skin surface, wherein redistributing the composition of nanoparticles comprises distribution with at least one of the group consisting of an ultrasound device and a massage device;

removing the remaining portion of the composition from the skin surface while leaving the composition localized within the targeted component of the skin tissue; and exposing the composition of nanoparticles to an energy source to induce a surface plasmon in said nanoparticles, thereby localizing thermal damage to said targeted component of the skin tissue.

11. The method of claim 10, wherein the concentration of the selected from the group consisting of: $10^{11}$, $10^{12}$, and $10^{13}$ particles per ml of the composition, and wherein the composition comprises a cream or a gel.

12. The method of claim 10,
wherein the coating is semiconductive,
wherein the conductive metal portion is inside the coating, and
wherein the coating is less conductive than the conductive metal portion.

13. The method of claim 10,
wherein the at least one of the massage device and the ultrasound device is configured for bubble formation or liquid micro streaming.

14. The method of claim 10,
wherein the conductive metal portion is a nanoplate comprising silver,
wherein the coating comprises any one of silica and polyethylene glycol (PEG), and
wherein the coating is less conductive than the conductive metal portion,
wherein the nanoplate has a dimension in a range of 100-250 nm.

15. The method of claim 10,
wherein the nanoparticles are plasmonic and have an optical density of 10 O.D. to 5,000 O.D. within an infrared light range,
wherein the coating is less conductive than the conductive metal portion,
wherein the coating is a non-metal coating.

16. A method of treating a targeted component of a skin tissue, comprising:
pre-treating a skin surface of a skin tissue to increase delivery of a composition of nanoparticles to a targeted component of the skin tissue,
applying the composition of nanoparticles to the skin surface wherein the nanoparticles are unassembled,
wherein the nanoparticles comprise at least one of gold, silver, and platinum,
distributing a portion of the composition of from the skin surface to the targeted component of the skin tissue while a remaining portion of the composition is left on the skin surface;
wherein the nanoparticles have a concentration selected from the group consisting of: $10^9$, $10^{10}$, $10^{11}$, $10^{12}$, and $10^{13}$ particles per ml of the composition,
wherein the nanoparticles comprise a coating, wherein said coating is selected from the group consisting of a hydrophilic coating and a hydrophobic coating,
removing the remaining portion of the composition from the skin surface, and
exposing the composition of nanoparticles to an energy wavelength, thereby localizing thermal damage to said targeted component of the skin tissue.

17. The method of claim 16,
wherein pre-treating the skin surface to increase delivery of the nanoparticles to the targeted component of the skin tissue comprises at least one of the group consisting of hair removal, shaving, waxing, peeling, a fractionated photothermolysis laser treatment, cyanoacrylate surface peeling, a calcium thioglycolate treatment, a surface exfoliation, a mechanical exfoliation, a salt glow, a microdermabrasion, a chemical exfoliation, a chemical exfoliation with an enzyme, a chemical exfoliation with alphahydroxy acid, and a chemical exfoliation with betahydroxy acid;
wherein distributing the composition of nanoparticles in contact with the skin surface comprises distribution with at least one of the group consisting of an ultrasound device and a massage device; and
wherein exposing the composition of nanoparticles to the energy wavelength induces a surface plasmon in said nanoparticles.

18. The method of claim 16,
wherein distributing the composition of nanoparticles in contact with the skin surface comprises distribution with at least one of the group consisting of an ultrasound device and a massage device;
wherein the energy wavelength is between 500 nm and 1200 nm,
wherein the nanoparticles have an optical density of 10 O.D. to 5,000 O.D. within an infrared light range and the concentration is selected from the group consisting of: $10^9$, $10^{10}$, $10^{11}$, and $10^{12}$ particles per ml of the composition,
wherein exposing the composition of nanoparticles to the energy wavelength induces a plurality of surface plasmons in said nanoparticles.

19. The method of claim 16,
wherein the nanoparticles are nanoplates,
wherein the nanoparticles have an optical density of 10 O.D. to 5,000 O.D. within an infrared light range and the concentration is selected from the group consisting of: $10^{10}$, $10^{11}$, $10^{12}$, and $10^{13}$ particles per ml of the composition; and
wherein exposing the composition of nanoparticles to the energy wavelength induces a surface plasmon in said nanoparticles.

20. The method of claim 16,
wherein distributing the composition of nanoparticles comprises distribution with at least one of the group consisting of an ultrasound device, a sonic force device, a massage device, a high pressure air flow device, a high pressure liquid flow device, and a vacuum device, and a dermabrasion device, and wherein removing the composition from the skin surface comprises using water or alcohol to remove the composition from the skin surface while leaving the composition localized at the targeted component of the skin tissue.

* * * * *